United States Patent
Seki

(10) Patent No.: US 9,624,181 B2
(45) Date of Patent: Apr. 18, 2017

(54) METHOD FOR PRODUCING BIARYL COMPOUND

(71) Applicant: API CORPORATION, Tokyo (JP)

(72) Inventor: Masahiko Seki, Tokyo (JP)

(73) Assignee: API Corporation, Tokyo (JP)

( * ) Notice: Subject to any disclaimer, the term of this patent is extended or adjusted under 35 U.S.C. 154(b) by 0 days.

(21) Appl. No.: 14/424,912

(22) PCT Filed: Aug. 30, 2013

(86) PCT No.: PCT/JP2013/073365
§ 371 (c)(1),
(2) Date: Feb. 27, 2015

(87) PCT Pub. No.: WO2014/034868
PCT Pub. Date: Mar. 6, 2014

(65) Prior Publication Data
US 2015/0239853 A1    Aug. 27, 2015

(30) Foreign Application Priority Data
Aug. 31, 2012 (JP) ................... 2012-191767

(51) Int. Cl.
C07D 257/04 (2006.01)
C07D 405/14 (2006.01)
C07D 403/10 (2006.01)
C07B 37/04 (2006.01)

(52) U.S. Cl.
CPC ............ *C07D 257/04* (2013.01); *C07B 37/04* (2013.01); *C07D 403/10* (2013.01); *C07D 405/14* (2013.01)

(58) Field of Classification Search
CPC .................................................. C07D 257/04
See application file for complete search history.

(56) References Cited

U.S. PATENT DOCUMENTS

2010/0160643 A1   6/2010  Pathi et al.
2012/0232283 A1   9/2012  Seki
2015/0239854 A1   8/2015  Seki

FOREIGN PATENT DOCUMENTS

| EP | 2 902 385 A1 | 8/2015 |
|---|---|---|
| JP | H07-121918 B2 | 12/1995 |
| JP | 2010-505926 A | 2/2010 |
| WO | 2004/069394 A2 | 8/2004 |
| WO | 2004/085428 A1 | 10/2004 |
| WO | 2007/136672 A2 | 11/2007 |
| WO | 2008/043996 A2 | 4/2008 |
| WO | 2011/061996 A1 | 5/2011 |

OTHER PUBLICATIONS

Chinese Patent Office, First Notification of Office Action in Chinese Patent Application No. 201380044890.X (Nov. 12, 2015).
Japanese Patent Office, Written Opinion of the International Searching Authority in International Patent Application No. PCT/JP2013/073365 (Oct. 8, 2013).
Ackermann et al., *Angew Chem. Int. Ed.*, 48(52): 9792-9826 (2009).
Arockiam et al., *Angew Chem. Int. Ed.*, 49(37): 6629-6632 (2010).
Arockiam et al., *Green Chemistry*, 11(11): 1871-1875 (2009).
Bernhart et al., *J. Med. Chem.*, 36(22): 3371-3380 (1993).
Beutler et al., *Organic Process Research & Development*, 11(5): 892-898 (2007).
Larsen et al., *J. Org. Chem.*, 59(21): 6391-6394 (1994).
Oi et al., *Chemistry Letters*, 37(9): 994-995 (2008).
Oi et al., *Tetrahedron*, 64(26): 6051-6059 (2008).
Ozdemir et al., *Eur. J. Inorg. Chem.*, 13: 1942-1949 (2009).
Stefane et al., *Eur. J. Org. Chem.*, 19: 3474-3481 (2011).
Zhao et al., *Synthetic Communications*, 43(13-15): 2110-2118 (2013).
Japanese Patent Office, International Search Report in International Patent Application No. PCT/JP2013/073365 (Oct. 8, 2013).
Diers et al., *Tetrahedron*, 69(22): 4445-4453 (2013).
Ghosh et al., *Beilstein Journal of Organic Chemistry*, 6(27): doi:10.3762/bjoc.6.27 (2010).
Seki et al., *The Journal of Organic Chemistry*, 76(24): 10198-10206 (2011).
European Patent Office, Extended European Search Report in European Patent Application No. 13832547.7 (Dec. 16, 2015).

*Primary Examiner* — Robert Havlin
(74) *Attorney, Agent, or Firm* — Leydig, Voit & Mayer, Ltd.

(57) ABSTRACT

The invention provides a production method of a biaryl compound of the formula [3] or a salt thereof, including reacting a 2-phenylazole derivative of the formula [1] or a salt thereof, with a benzene derivative of the formula [2] or a salt thereof in the presence of a metal catalyst, a base, and one or more of (a) a monocarboxylic acid metal salt, (b) a dicarboxylic acid metal salt, (c) a sulfonic acid metal salt, and (d) a phosphate or phosphoric amide metal salt represented by $R^4{}_xP(O)(OM)_y$.

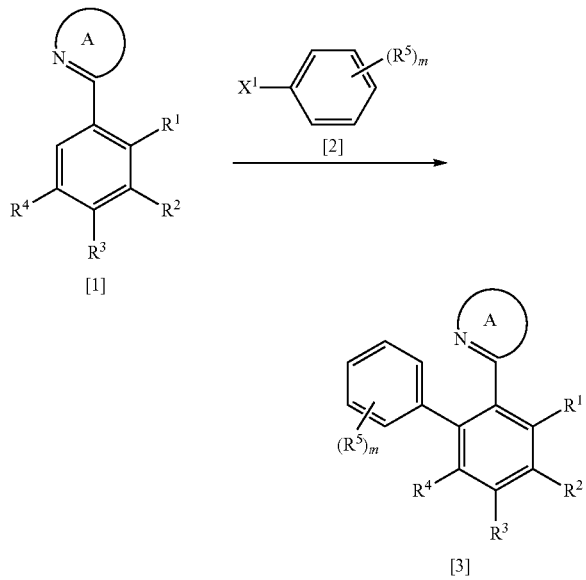

wherein each symbol is as defined herein.

14 Claims, No Drawings

METHOD FOR PRODUCING BIARYL COMPOUND

CROSS-REFERENCE TO RELATED APPLICATIONS

This patent application is the U.S. national phase of International Patent Application No. PCT/JP2013/073365, filed Aug. 30, 2013, which claims the benefit of Japanese Patent Application No. 2012-191767, filed on Aug. 31, 2012, which are incorporated by reference in their entireties herein.

TECHNICAL FIELD

The present invention relates to a production method of a biaryl compound or a salt thereof useful as an intermediate for angiotensin II receptor blockers.

BACKGROUND ART

Losartan potassium, valsartan, olmesartan medoxomil, candesartan cilexetil, telmisartan, irbesartan and the like are useful as angiotensin II receptor blockers.

As a production method of these compounds, for example, the production method described in J. Org. Chem., 1994, vol. 59, pages 6391-6394 (non-patent document 1) is known as a synthesis method of losartan, the production method described in Org. Process Res. Dev., 2007, vol. 11, pages 892-898 (non-patent document 2) is known as a synthesis method of valsartan, and the production method described in J. Med. Chem., 1993, vol. 36, pages 3371-3380 (non-patent document 3) is known as a synthesis method of irbesartan.

As a production method of olmesartan, the production methods described in JP-B-7-121918 (patent document 1), JP-A-2010-505926 (patent document 2), WO 2004/085428 (patent document 3) and the like are known.

Also, as a conventional method of biphenylation reaction, for example, the method described in Chem. Lett., 2008, vol. 37, NO. 9, pages 994-995 (non-patent document 4), and the methods described in Tetrahedron, 2008, vol. 64, pages 6051-6059 (non-patent document 5), Angewandte Chemie International Edition, 2009, vol. 48, pages 9792-9827 (non-patent document 6), and WO 2011/061996 (patent document 4) are known.

DOCUMENT LIST

Patent Documents patent document 1: JP-B-7-121918
patent document 2: JP-A-2010-505926
patent document 3: WO 2004/085428
patent document 4: WO 2011/061996

Non-Patent Documents non-patent document 1: J. Org. Chem., 1994, vol. 59, pages 6391-6394
non-patent document 2: Org. Process Res. Dev., 2007, vol. 11, pages 892-898
non-patent document 3: J. Med. Chem., 1993, vol. 36, pages 3371-3380
non-patent document 4: Chem. Lett., 2008, vol. 37, No. 9, pages 994-995
non-patent document 5: Tetrahedron, 2008, vol. 64, pages 6051-6059 non-patent document 6: Angewandte Chemie International Edition, 2009, vol. 48, pages 9792-9827

SUMMARY OF THE INVENTION

Problems to be Solved by the Invention

Since the aforementioned production methods of the Prior Art require expensive metal compounds and include plural reaction steps, the development of a more economical production method has been desired.

The present invention aims to provide a novel production method capable of producing a biaryl compound, which is useful as an intermediate for angiotensin II receptor blockers, under conditions suitable for economical and industrial production.

Means of Solving the Problems

The present inventors have conducted intensive studies in an attempt to solve the aforementioned problems and found that a biaryl compound useful as an intermediate for angiotensin II receptor blockers can be produced economically under conditions suitable for industrial production by using an inexpensive metal compound as a catalyst and further using a particular compound, which resulted in the completion of the present invention.

Accordingly, the present invention relates to;
[1] a method of producing a biaryl compound represented by the formula [3]:

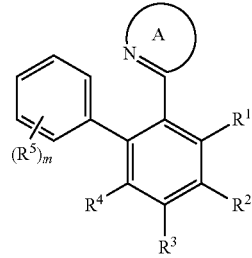

[3]

wherein $R^1$ to $R^4$ are each independently a hydrogen atom, or an alkyl group, an aralkyl group or an aryl group, each of which optionally has substituent(s), $R^5$ is an alkyl group, an aralkyl group or an aryl group, each of which optionally has substituent(s), m is an integer of 0 to 5, and ring A is an optionally substituted nitrogen-containing heterocycle, or a salt thereof (also referred to as biaryl compound [3]) (hereinafter also referred to as "production method 1"), comprising reacting a 2-phenylazole derivative represented by the formula [1]:

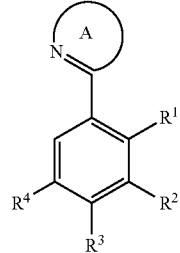

[1]

wherein each symbol is as defined above,
or a salt thereof (also referred to as 2-phenylazole derivative [1]) with a benzene derivative represented by the formula [2]:

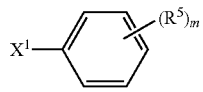

wherein $R^5$ and m are as defined above, and $X^1$ is a leaving group,
(also referred to as benzene derivative [2]), in the presence of a metal catalyst, a base and one or more kinds of compounds selected from the group consisting of the following (a)-(d);
(a) a monocarboxylic acid metal salt
(b) a dicarboxylic acid metal salt
(c) a sulfonic acid metal salt, and
(d) a phosphate or phosphoric amide metal salt represented by $R^4{}_xP(O)(OM)_y$, wherein $R^4$ is $R'''O$ or $R'''{}_2N$ (wherein $R'''$ is a hydrogen atom, or a straight chain or branched chain alkyl group having 1-20 carbon atoms, an aralkyl group having 7-14 carbon atoms or an aryl group having 6-18 carbon atoms, each of which optionally contains a nitrogen atom, an oxygen atom or a sulfur atom), M is a metal atom, x and y are each independently an integer of 1 or 2, and x+y is 3;
[2] a method of producing a biaryl compound represented by the formula [3]:

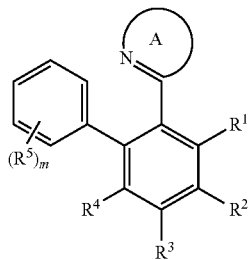

wherein $R^1$ to $R^4$ are each independently a hydrogen atom, or an alkyl group, an aralkyl group or an aryl group, each of which optionally has substituent(s), $R^5$ is an alkyl group, an aralkyl group or an aryl group, each of which optionally has substituent(s), m is an integer of 0 to 5, and ring A is an optionally substituted nitrogen-containing heterocycle, or a salt thereof (also referred to as biaryl compound [3]) (hereinafter also referred to as "production method 1'"), comprising reacting a 2-phenylazole derivative represented by the formula [1]:

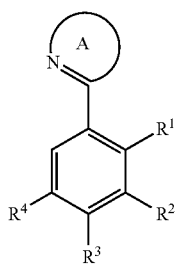

wherein each symbol is as defined above,
or a salt thereof (also referred to as 2-phenylazole derivative [1]) with a benzene derivative represented by the formula [2]:

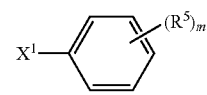

wherein $R^5$ and m are as defined above, and $X^1$ is a leaving group,
(also referred to as benzene derivative [2]), in the presence of a metal catalyst, a base and one or more kinds of compounds selected from the group consisting of the following (a)-(d);
(a) a monocarboxylic acid metal salt
(b) a dicarboxylic acid metal salt
(c) a sulfonic acid metal salt, and
(d) a phosphate metal salt represented by $(R'''O)_xP(O)(OM)_y$, wherein $R'''$ is a hydrogen atom, or a straight chain or branched chain alkyl group having 1-20 carbon atoms, an aralkyl group having 7-14 carbon atoms or an aryl group having 6-18 carbon atoms, each of which optionally contains a nitrogen atom, an oxygen atom or a sulfur atom, M is a metal atom, x and y are each independently an integer of 1 or 2, and x+y is 3;
[3] The production method of the above-mentioned [1] or [2], wherein the reaction is performed under conditions comprising further presence of a phosphine compound;
[4] The method of any one of the above-mentioned [1] to [3], wherein the formula [1] described in the above-mentioned [1] or [2] is a 2-phenyltetrazole derivative represented by the formula [1']:

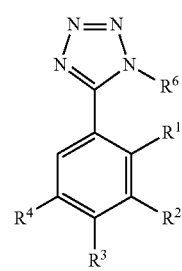

wherein $R^6$ is a tetrazolyl-protecting group, and $R^1$ to $R^4$ are as defined above,
or a salt thereof (also referred to as 2-phenyltetrazole derivative [1']), and the formula [2] described in the above-mentioned [1] or [2] is a benzene derivative represented by the formula [2']:

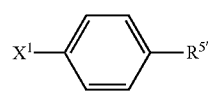

wherein $R^{5'}$ is a methyl group, a methyl group substituted by a protected hydroxyl group or a lower alkoxycarbonyl group, and $X^1$ is as defined above (also referred to as benzene derivative [2']);

[5] a method of producing a biaryltetrazole derivative represented by the formula [5]:

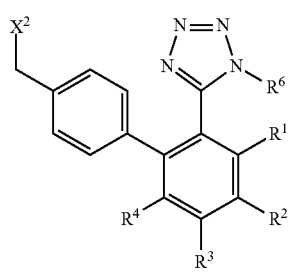

[5]

wherein $X^2$ is a halogen atom, and $R^1$ to $R^4$ and $R^6$ are as defined above,
or a salt thereof (also referred to as biaryltetrazole derivative [5]), comprising
1) in the biaryltetrazole compound represented by the formula [3']:

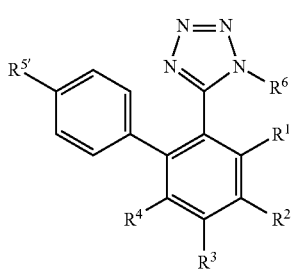

[3']

wherein each symbol is as defined above,
which is obtained by the method of the above-mentioned [4], or a salt thereof (also referred to as biaryltetrazole compound [3']),
1-A) (a) deprotecting the compound when $R^{5'}$ is a methyl group substituted by a protected hydroxyl group,
(b) reducing the compound when $R^{5'}$ is a lower alkoxycarbonyl group,
to give a compound represented by the formula [4]:

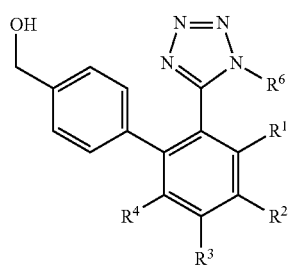

[4]

wherein each symbol is as defined above,
or a salt thereof (also referred to as compound [4]), and further halogenating the compound; or
1-B) halogenating a compound represented by the formula [3'] when $R^{5'}$ of the compound represented by the formula [3'] is a methyl group (hereinafter also referred to as "production method 2")

[6] a method of producing a compound represented by the formula [11]:

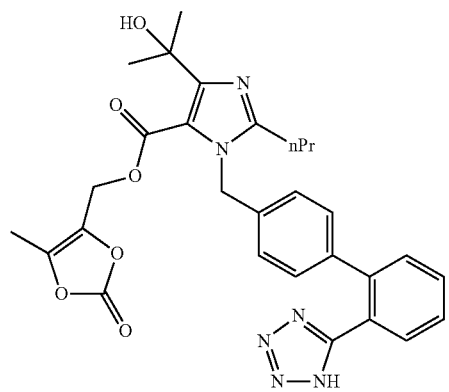

[11]

or a salt thereof (that is, olmesartan or a salt thereof, hereinafter also referred to as compound [11]), comprising
1) reacting a biaryltetrazole derivative represented by the formula [5']:

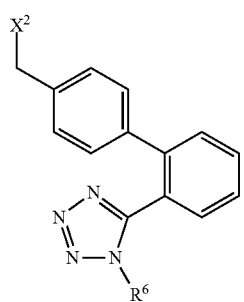

[5']

wherein each symbol is as defined above,
which is obtained by the method of the above-mentioned [5], or a salt thereof (also referred to as biaryltetrazole derivative [5']) with a compound represented by the formula [6]:

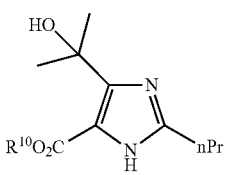

[6]

wherein $R^{10}$ is a carboxy-protecting group,
or a salt thereof (also referred to as compound [6]) to give a compound represented by the formula [7]:

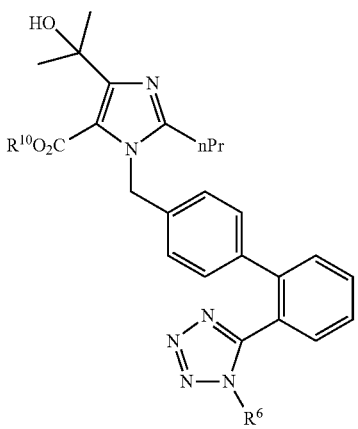

[7]

wherein each symbol is as defined above,
or a salt thereof (also referred to as compound [7]);

2) removing $R^6$ of compound [7] to give a compound represented by the formula [Y1]:

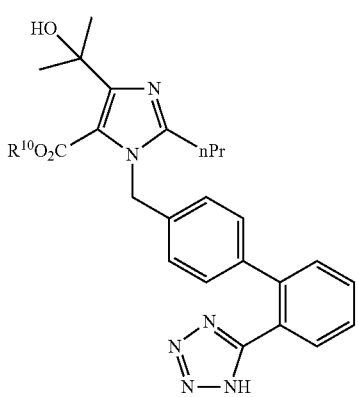

[Y1]

wherein each symbol is as defined above,
or a salt thereof (also referred to as compound [Y1]);

3) reacting compound [Y1] with a compound represented by the formula [Y3]: $R^{6'}$—$X^5$ (wherein $R^{6'}$ is a trityl group, and $X^5$ is a halogen atom) (also referred to as compound [Y3]) to give a compound represented by the formula [Y2]:

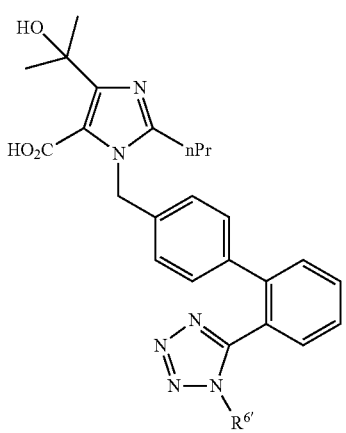

[Y2]

wherein each symbol is as defined above,
or a salt thereof (also referred to as compound [Y2]);

4) hydrolyzing compound [Y2] to give a compound represented by the formula [8']:

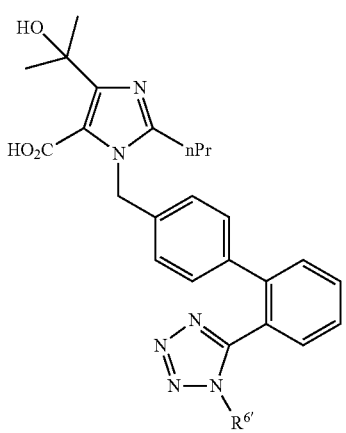

[8']

wherein each symbol is as defined above,
or a salt thereof (also referred to as compound [8']);

5) reacting compound [8'] with a compound represented by the formula [9]:

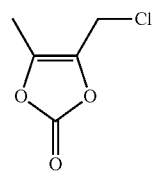

[9]

(also referred to as compound [9]) to give a compound represented by the formula [10']:

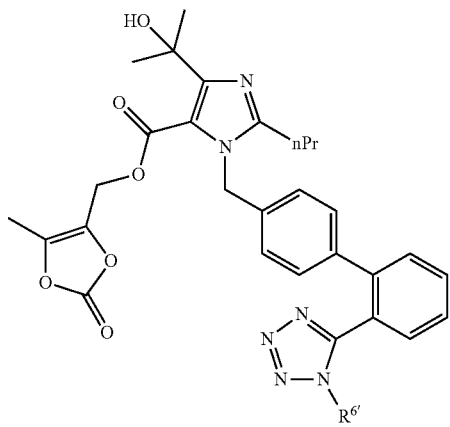

[10']

wherein each symbol is as defined above,
or a salt thereof (also referred to as compound [10']); and
6) removing $R^{6'}$ of compound [10'] (hereinafter also referred to as "production method 3'");
[7] a method of producing a compound represented by the formula [11]:

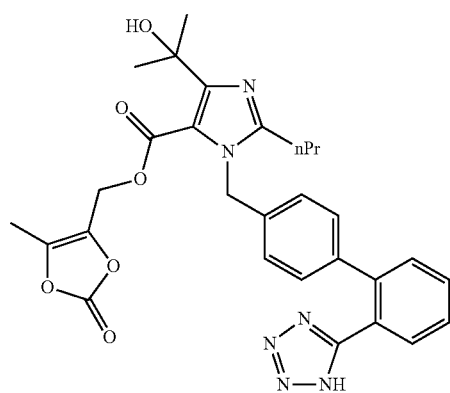

[11]

or a salt thereof (that is, olmesartan or a salt thereof), comprising
1) reacting a biaryltetrazole derivative represented by the formula [5']:

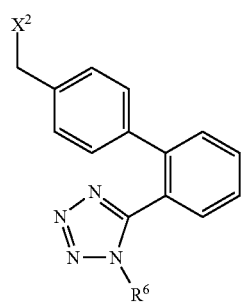

[5']

wherein each symbol is as defined above,
which is obtained by the method of the above-mentioned [5], or a salt thereof (also referred to as biaryltetrazole derivative [5']) with a compound represented by the formula [6']:

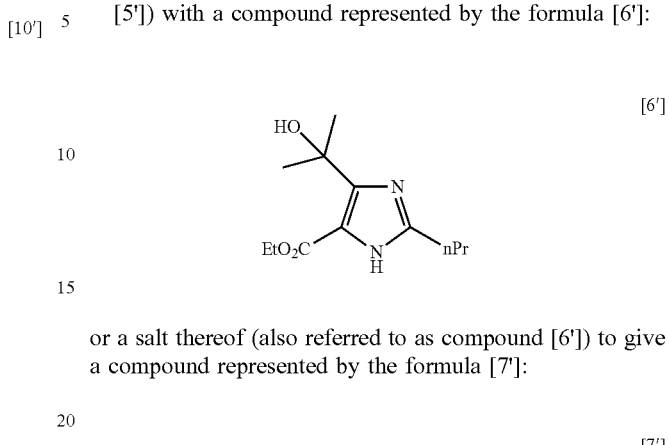

[6']

or a salt thereof (also referred to as compound [6']) to give a compound represented by the formula [7']:

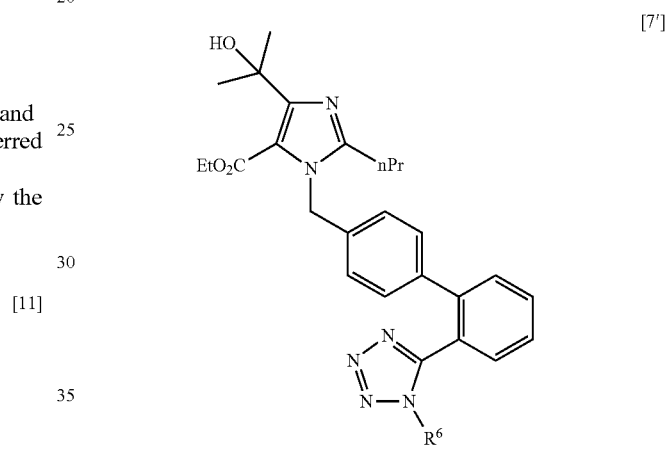

[7']

wherein each symbol is as defined above,
or a salt thereof (also referred to as compound [7']);
2) hydrolyzing compound [7'] to give a compound represented by the formula [8]:

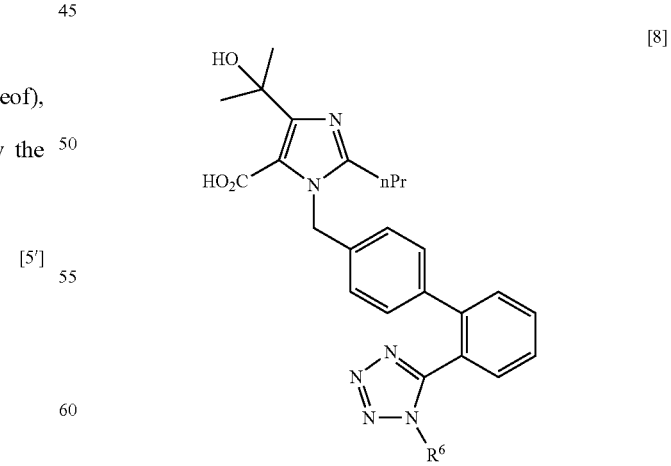

[8]

wherein each symbol is as defined above,
or a salt thereof (also referred to as compound [8]);

3) reacting compound [8] with a compound represented by the formula [9]:

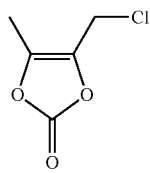

[9]

(also referred to as compound [9]) to give a compound represented by the formula [10]:

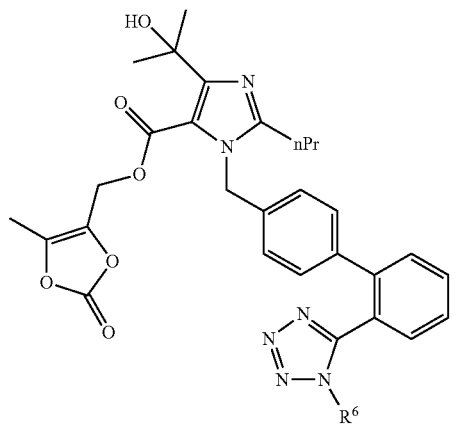

[10]

wherein each symbol is as defined above,
or a salt thereof (also referred to as compound [10]); and
4) removing $R^6$ of compound [10] (hereinafter also referred to as "production method 3");

[8] a method of producing a compound represented by the formula [16]:

[16]

or a salt thereof (that is, losartan or a salt thereof, hereinafter also referred to as compound [16]), comprising 1) reacting a biaryltetrazole derivative represented by the formula [5']:

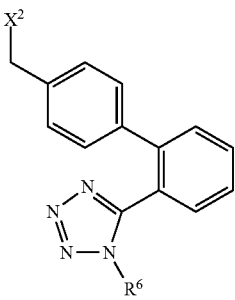

[5']

wherein each symbol is as defined above,
which is obtained by the method of the above-mentioned [5], or a salt thereof with a compound represented by the formula [12]:

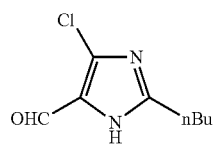

[12]

or a salt thereof (also referred to as compound [12]) to give a compound represented by the formula [13]:

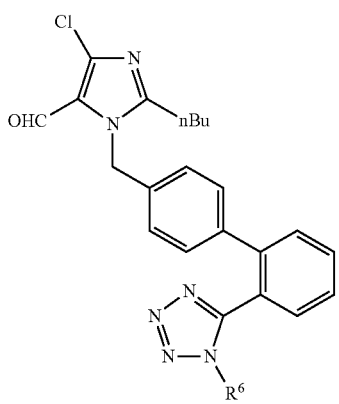

[13]

wherein each symbol is as defined above,
or a salt thereof (also referred to as compound [13]); and 2-A) reducing compound [13] to give a compound represented by the formula [14]:

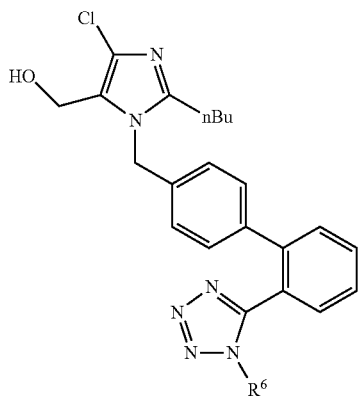

[14]

wherein each symbol is as defined above,
or a salt thereof (also referred to as compound [14]), and further removing $R^6$; or
2-B) removing $R^6$ of compound [13] to give a compound represented by the formula [15]:

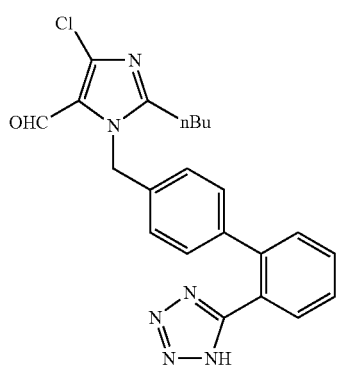

[15]

or a salt thereof (also referred to as compound [15]), and further reducing the compound (hereinafter also referred to as "production method 4");
[9] a method of producing a compound represented by the formula [23]

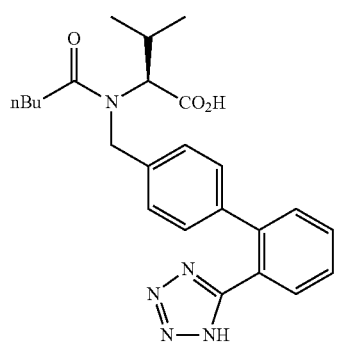

[23]

or a salt thereof (that is, valsartan or a salt thereof, hereinafter also referred to as compound [23]), comprising 1) reacting a biaryltetrazole derivative represented by the formula [5']:

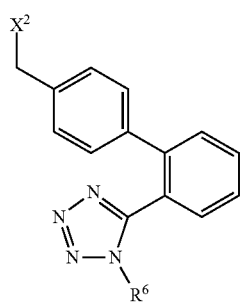

[5']

wherein each symbol is as defined above,
which is obtained by the method of the above-mentioned [5], or a salt thereof with a compound represented by the formula [17]:

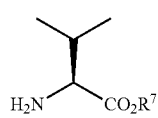

[17]

wherein $R^7$ is a carboxy-protecting group,
or a salt thereof (also referred to as compound [17]) to give a compound represented by the formula [18]:

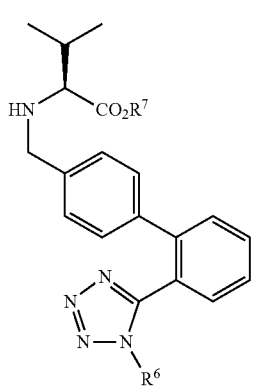

[18]

wherein each symbol is as defined above,
or a salt thereof (also referred to as compound [18]);

2-A) removing R[6] of compound [18] to give a compound represented by the formula [19]:

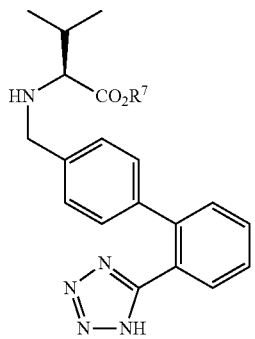

[19]

wherein each symbol is as defined above,
or a salt thereof (also referred to as compound [19]);

3-A) reacting compound [19] with a compound represented by the formula [20]: $CH_3CH_2CH_2CH_2CO-X^3$ (wherein $X^3$ is a leaving group) (also referred to as compound [20]) to give a compound represented by the formula [21]:

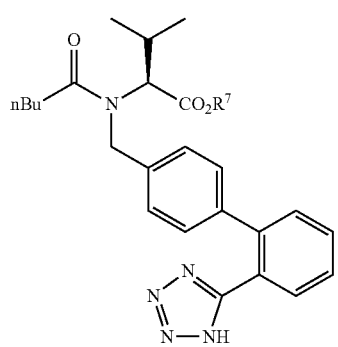

[21]

wherein each symbol is as defined above,
or a salt thereof (also referred to as compound [21]);

4-A) removing R[7] of compound [21]; or

2-B) reacting compound [18] with compound [20] to give a compound represented by the formula [22]:

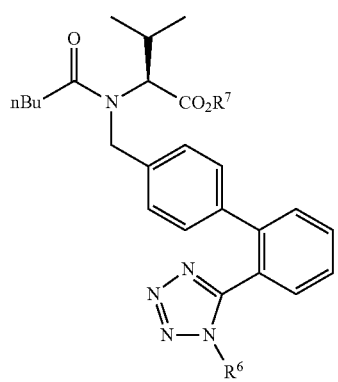

[22]

wherein each symbol is as defined above,
or a salt thereof (also referred to as compound [22]); and 3-B) removing R[6] and R[7] of compound [22] (hereinafter also referred to as "production method 5");

[10] a method of producing a compound represented by the formula [26]:

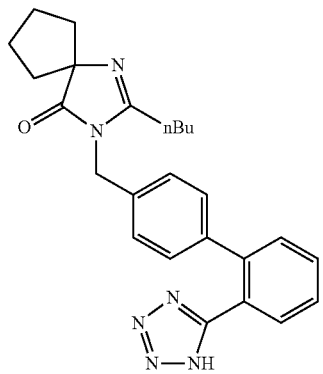

[26]

or a salt thereof (that is, irbesartan or a salt thereof, hereinafter to be also referred to as compound [26]),
comprising reacting a biaryltetrazole derivative represented by the formula [5']:

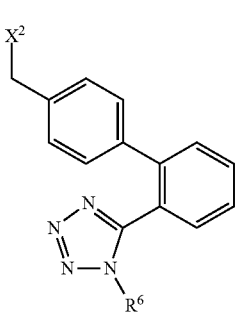

[5']

wherein each symbol is as defined above,
which is obtained by the method of the above-mentioned [5],
or a salt thereof with a compound represented by the formula [24]:

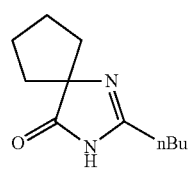

[24]

or a salt thereof (also referred to as compound [24]) to give a compound represented by the formula [25]:

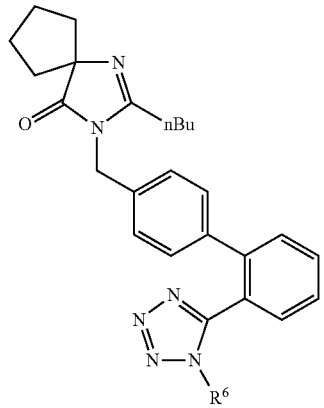
[25]

wherein each symbol is as defined above,
or a salt thereof (also referred to as compound [25]), and further removing $R^6$ (hereinafter also referred to as "production method 6");

[11] a method of producing a compound represented by the formula [35]

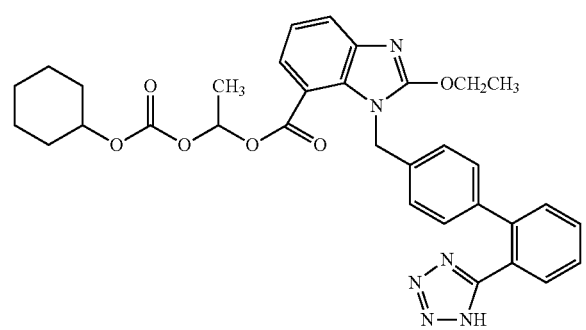
[35]

or a salt thereof (that is, candesartan cilexetil or a salt thereof, hereinafter to be also referred to as compound [35]), comprising 1) reacting a biaryltetrazole derivative represented by the formula [5']:

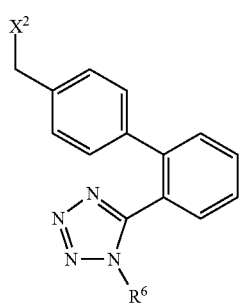
[5']

wherein each symbol is as defined above,
which is obtained by the method of the above-mentioned [5], or a salt thereof with a compound represented by the formula [X]:

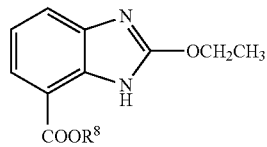
[X]

wherein $R^8$ is a carboxy-protecting group,
or a salt thereof (also referred to as compound [X]) to give a compound represented by the formula [31]:

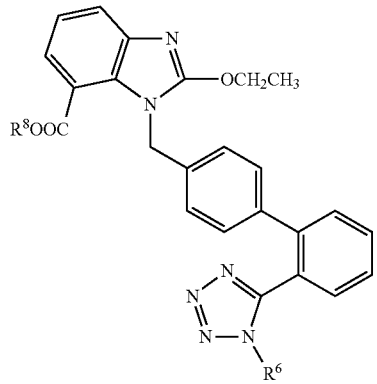
[31]

wherein each symbol is as defined above,
or a salt thereof (also referred to as compound [31]);

2) removing $R^8$ of compound [31] to give a compound represented by the formula [32]:

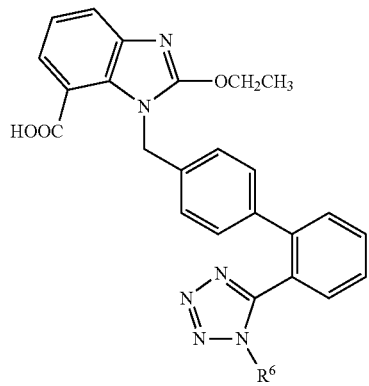
[32]

wherein each symbol is as defined above,
or a salt thereof (also referred to as compound [32]);

3) reacting compound [32] with a compound represented by the formula [33]:

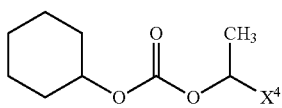
[33]

wherein $X^4$ is a leaving group or a hydroxyl group, or a salt thereof (also referred to as compound [33]) to give a compound represented by the formula [34]:

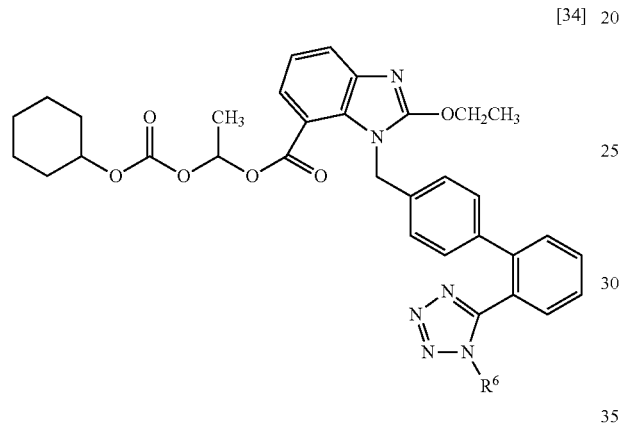
[34]

wherein each symbol is as defined above, or a salt thereof (compound [34]); and 4) removing $R^6$ of compound [34] (hereinafter also referred to as "production method 7"); and

[12] a method of producing a compound represented by the formula [35]

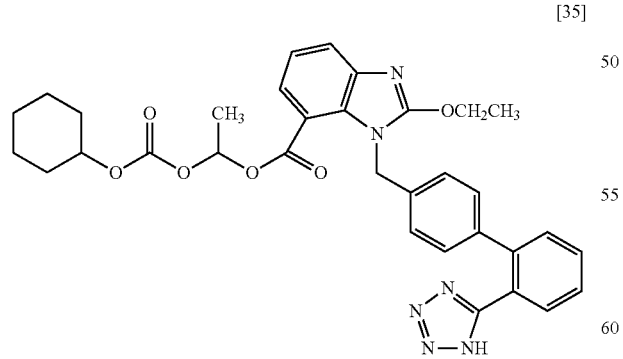
[35]

or a salt thereof (that is, candesartan cilexetil or a salt thereof), comprising 1) reacting a biaryltetrazole derivative represented by the formula [5']:

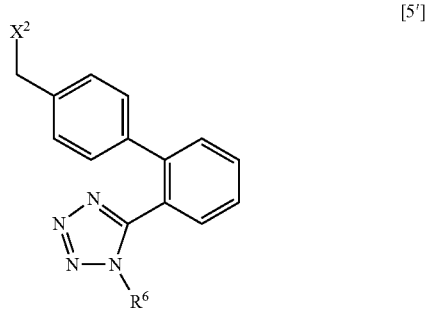
[5']

wherein each symbol is as defined above, which is obtained by the method of the above-mentioned [5], or a salt thereof with a compound represented by the formula [27]:

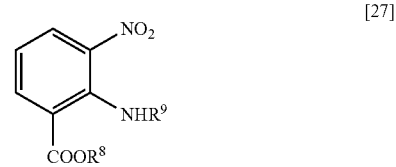
[27]

wherein $R^8$ is a carboxy-protecting group, and $R^9$ is an amino-protecting group, or a salt thereof (also referred to as compound [27]) to give a compound represented by the formula [28]:

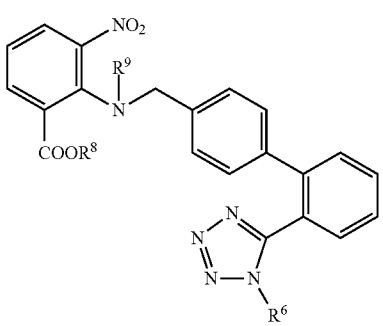
[28]

wherein each symbol is as defined above, or a salt thereof (also referred to as compound [28]);

2) removing $R^9$ of compound [28] to give a compound represented by the formula [29]:

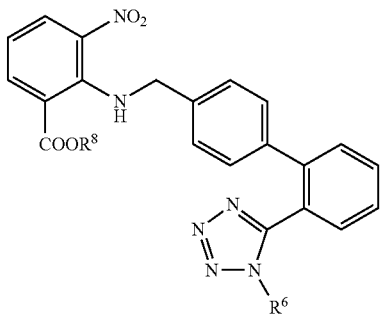

[29]

wherein each symbol is as defined above, or a salt thereof (also referred to as compound [29]);

3) reducing compound [29] to give a compound represented by the formula [30]:

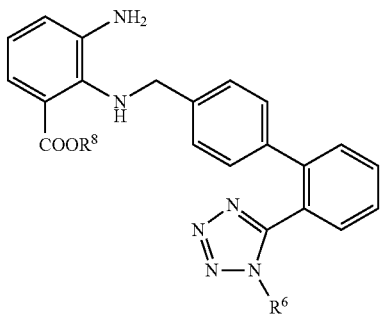

[30]

wherein each symbol is as defined above, or a salt thereof (also referred to as compound [30]);

4) reacting compound [30] with tetraethoxymethane to give a compound represented by the formula [31]:

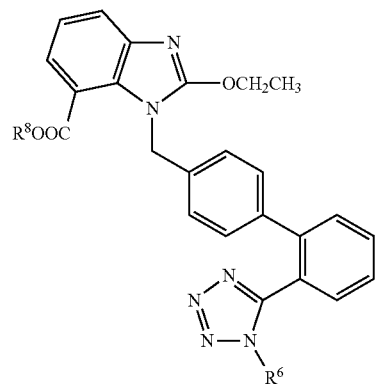

[31]

wherein each symbol is as defined above, or a salt thereof (also referred to as compound [31]);

4) removing $R^8$ of compound [31] to give a compound represented by the formula [32]:

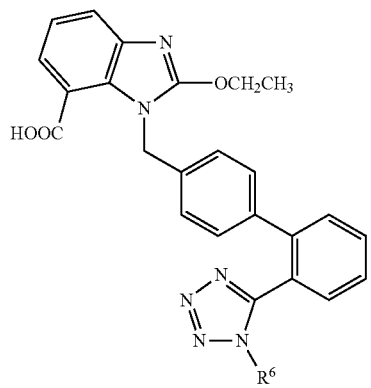

[32]

wherein each symbol is as defined above, or a salt thereof (also referred to as compound [32]);

5) reacting compound [32] with a compound represented by the formula [33]:

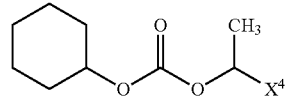

[33]

wherein $X^4$ is a leaving group or a hydroxyl group, or a salt thereof (also referred to as compound [33]) to give a compound represented by the formula [34]:

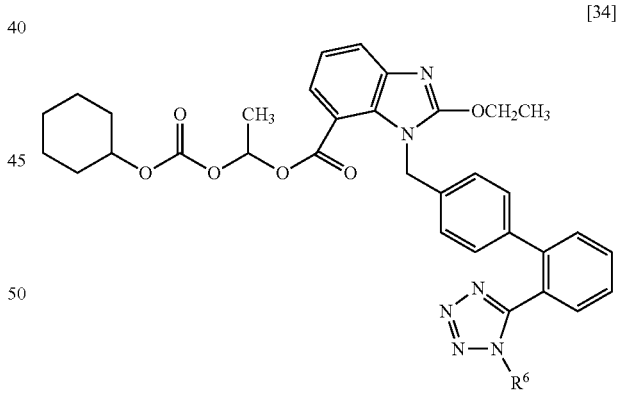

[34]

wherein each symbol is as defined above, or a salt thereof (also referred to as compound [34]); and 6) removing $R^6$ of compound [34] (hereinafter to be also referred to as "production method 7").

Effect of the Invention

According to the present invention, a biaryl compound useful as an intermediate for angiotensin II receptor blockers can be produced economically under conditions suitable for industrial production.

DETAILED DESCRIPTION OF THE INVENTION

The definitions of the symbols and terms used in the present invention are described in detail in the following.

In the present specification, the "tetrazolyl-protecting group" is not particularly limited as long as it can stably protect a tetrazolyl group during reactions. Specifically, those described in Protective Groups in Organic Synthesis 3$^{rd}$ Ed., T. W. Greene, P. G. M. Wuts, John Wiley and Sons, Inc., 1999 can be mentioned.

Examples of the tetrazolyl-protecting group include $C_{7-19}$ aralkyl group (e.g., benzyl, diphenylmethyl, trityl etc.); substituted $C_{7-19}$ aralkyl groups such as substituted benzyl, substituted diphenylmethyl and the like (preferably, $C_{7-19}$ aralkyl substituted by 1 to 3 substituents selected from the group consisting of $C_{1-6}$ alkyl, nitro, $C_{1-6}$ alkylenedioxy and $C_{1-6}$ alkoxy (when two or more substituents are present, they may be the same or different and the substituents may be bonded to each other to form a ring), for example, p-methylbenzyl, p-nitrobenzyl, 2,4-dimethoxybenzyl, 3,4-dimethoxybenzyl, 3,4-(methylenedioxy)benzyl, p-methoxybenzyl, o-methoxybenzyl, 3,4,5-trimethoxybenzyl etc.);
substituted $C_{1-6}$ alkyl group (preferably, $C_{1-6}$ alkyl substituted by 1 to 3 substituents selected from the group consisting of hydroxy, alkoxy (e.g., $C_{1-6}$ alkoxy), aryloxy (e.g., $C_{6-10}$ aryloxy) and dialkylamino (e.g., di($C_{1-6}$ alkyl)amino), for example, hydroxymethyl, alkoxymethyl, aryloxymethyl, dialkylaminomethyl etc.);
trialkylsilyl group (preferably, tri($C_{1-6}$ alkyl)silyl);
$C_{1-6}$ alkyl group (e.g., t-butyl etc.) and the like.

In the present specification, specific examples of the hydroxyl-protecting group of the "methyl group substituted by a protected hydroxyl group" include those described in Protective Groups in Organic Synthesis 3$^{rd}$ Ed., T. W. Greene, P. G. M. Wuts, John Wiley and Sons, Inc., 1999.

Examples of the hydroxyl-protecting group include acyl group (preferably, $C_{1-6}$ alkyl-carbonyl, $C_{3-8}$ cycloalkyl-carbonyl, $C_{6-10}$ aryl-carbonyl, for example, acetyl, propionyl, butyryl, isobutyryl, pivaloyl, cyclohexylcarbonyl, benzoyl etc.),
$C_{7-19}$ aralkyl group (e.g., benzyl etc.),
trialkylsilyl group (preferably, tri($C_{1-6}$ alkyl)silyl, for example, trimethylsilyl, triethylsilyl, triisopropylsilyl, t-butyldimethylsilyl etc.),
alkoxycarbonyl group (preferably, $C_{1-6}$ alkoxy-carbonyl) and the like.

In the present specification, the "carboxy-protecting group" is not particularly limited as long as it can stably protect a carboxy group during reaction, and specific examples thereof include those described in Protective Groups in Organic Synthesis 3$^{rd}$ Ed., T. W. Greene, P. G. M. Wuts, John Wiley and Sons, Inc., 1999.

Examples of the carboxy-protecting group include alkyl group (preferably, $C_{1-6}$ alkyl, for example, methyl, ethyl, propyl, isopropyl, butyl, pentyl, hexyl),
$C_{3-8}$ cycloalkyl group (e.g., cyclohexyl),
$C_{7-19}$ aralkyl group (e.g., benzyl, diphenylmethyl, trityl),
$C_{2-6}$ alkenyl group (e.g., allyl)
and the like.

In the present specification, the "amino-protecting group" is not particularly limited as long as it can stably protect an amino group during reaction, and specific examples thereof include those described in Protective Groups in Organic Synthesis 3$^{rd}$ Ed., T. W. Greene, P. G. M. Wuts, John Wiley and Sons, Inc., 1999.

Examples of the amino-protecting group include acyl group (preferably, $C_{1-6}$ alkyl-carbonyl, $C_{3-8}$ cycloalkyl-carbonyl, $C_{6-10}$ aryl-carbonyl, for example, acetyl, propionyl, butyryl, isobutyryl, pivaloyl, cyclohexylcarbonyl, benzoyl etc.), lower alkoxycarbonyl group and the like.

In the present specification, examples of the "lower alkoxycarbonyl group" include linear or branched chain $C_{1-12}$ alkoxy-carbonyl group, with preference given to methoxycarbonyl, ethoxycarbonyl, butoxycarbonyl (e.g., tert-butoxycarbonyl) and the like.

Examples of the "leaving group" for X' include halogen atom,
$C_{6-10}$ arylsulfonyloxy group optionally substituted by 1 to 3 $C_{1-6}$ alkyl group (e.g., toluenesulfonyloxy etc.),
$C_{1-6}$ alkylsulfonyloxy group optionally substituted by 1 to 3 halogen atoms (e.g., methanesulfonyloxy, trifluoromethanesulfonyloxy etc.)
and the like.

Examples of the "leaving group" for $X^3$ include halogen atom,
$C_{6-10}$ arylsulfonyloxy group optionally substituted by 1 to 3 $C_{1-6}$ alkyl groups (e.g., toluenesulfonyloxy etc.),
$C_{1-6}$ alkylsulfonyloxy group optionally substituted by 1 to 3 halogen atoms (e.g., methanesulfonyloxy etc.),
alkanoyloxy group (preferably, $C_{1-6}$ alkyl-carbonyloxy), aroyloxy group (preferably, $C_{6-10}$ aryl-carbonyloxy), dialkoxyphosphoryloxy group (preferably, di($C_{1-6}$ alkoxy)phosphoryloxy),
diaryloxyphosphoryloxy group (preferably, di($C_{6-10}$ aryloxy)phosphoryloxy)
and the like.

Examples of the "halogen atom" in the present specification include fluorine, chlorine, bromine and iodine.

Examples of the "alkyl group" in the present specification include, unless otherwise specified, linear or branched chain alkyl groups having 1-12 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the "aralkyl group" in the present specification include, unless otherwise specified, aralkyl groups having 7-14 carbon atoms, such as benzyl, phenethyl, 1-methyl-2-phenylethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Examples of the "aryl group" in the present specification include, unless otherwise specified, aryl groups having 6-14 carbon atoms, such as phenyl, 1-naphthyl, 2-naphthyl, 2-anthryl and the like. The aryl group may be fused with "$C_{3-8}$ cycloalkane" or "$C_{3-8}$ cycloalkene" described below and, for example, tetrahydronaphthyl and the like can be mentioned.

Examples of the "nitrogen-containing heterocycle" in the present specification include, unless otherwise specified, a 3- to 8-membered nitrogen-containing heterocycle (preferably, 5- or 6-membered nitrogen-containing aromatic heterocycle) containing, as a ring-constituting atom besides carbon atoms and one nitrogen atom, 1 to 3 heteroatoms of one or two kinds selected from a nitrogen atom, a sulfur atom and an oxygen atom. Specifically, for example, pyrrole ring, imidazole ring, oxazole ring, thiazole ring, oxadiazole ring, thiadiazole ring, triazole ring, tetrazole ring, pyridine ring, pyridazine ring, pyrimidine ring, pyrazine ring and the like can be mentioned.

Examples of the "alkyl group, aralkyl group or aryl group, each of which optionally has substituent(s)" and "optionally substituted nitrogen-containing heterocycle" in the present specification include "alkyl group", "aralkyl group", "aryl group", and "nitrogen-containing heterocycle", each of which optionally has, at substitutable position(s), 1 to 5 substituents selected from (1) halogen atom;
(2) hydroxy;
(3) amino;
(4) nitro;
(5) cyano;
(6) heterocyclic group optionally substituted by 1 to 3 substituents selected from halogen atom, hydroxy, amino, nitro, cyano, optionally halogenated $C_{1-6}$ alkyl, mono- or di-$C_{1-5}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N—$C_{1-6}$ alkyl-N—$C_{6-14}$ aryl-amino;
(11) N—$C_{1-6}$ alkyl-N—$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxy;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N—$C_{1-6}$ alkyl-N—$C_{6-14}$ aryl-carbamoyl;
(26) mono- or di-5- to 7-membered heterocyclyl-carbamoyl;
(27) $C_{1-6}$ alkyl-carbonylamino optionally substituted by carboxy;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{6-5}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl;
(37) tri-$C_{1-6}$ alkylsilyloxy;
and the like. When a plurality of substituents exist, the respective substituents may be the same or different.

The production method of the present invention is explained now.

[Production Method 1] and [Production Method 1']

2-Phenylazole derivative [1] and benzene derivative [2] may be commercially available products, and 2-phenylazole derivative [1] may be produced by the method described in WO 2009/49305, or a method analogous thereto.

(Step 1)

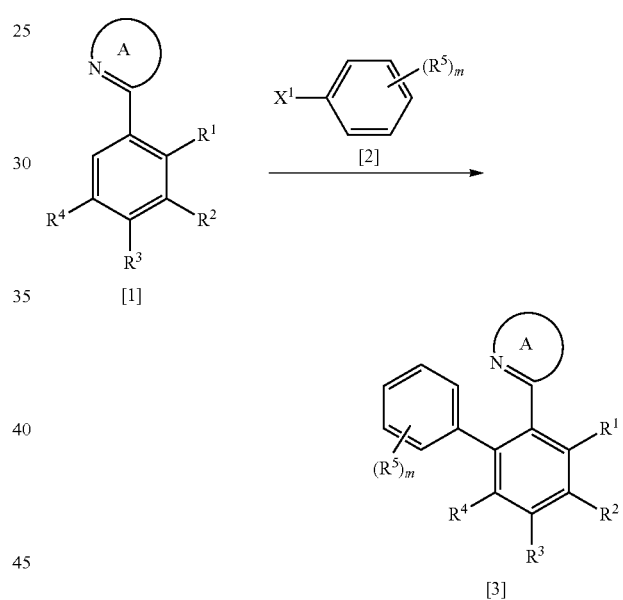

Biaryl compound [3] can be produced by reacting 2-phenylazole derivative [1] with benzene derivative [2] in the presence of a metal catalyst, a base and one or more kinds of compounds selected from the group consisting of the aforementioned (a)-(d). This reaction can also be performed in a solvent.

As the metal catalyst, ruthenium catalyst, iridium catalyst, rhodium catalyst or palladium catalyst can be used.

Examples of the ruthenium catalyst include dichlorotris(triphenylphosphine)ruthenium (II) ($RuCl_2(PPh_3)_3$), dichloro(1,5-cyclooctadiene)ruthenium (II) polymer (sometimes indicated as $[RuCl_2(\eta^4\text{-COD})]_n$ or poly $[(\eta^2,\eta^2\text{-cyclo}octa\text{-}1,5\text{-diene})ruthenium\text{-}di\text{-}\mu\text{-chloro}])$, $[RuCl_2(\eta^6\text{-}C_6H_6)]_2$, dichloro(p-cymene)ruthenium (II) dimer ($[Ru(p\text{-cymene})Cl_2]_2$), dichloro(mesitylene)ruthenium (II) dimer ($[Ru(mesitylene)Cl_2]_2$), ruthenium chloride (III) ($RuCl_3$), ruthenium chloride (III) hydrate ($RuCl_3.xH_2O$), ruthenium carbon, and dipivaloyloxy(p-cymene)ruthenium (II). Preferred are ruthenium catalysts (e.g., dichloro(p-cymene)

ruthenium (II) dimer ([Ru(p-cymene)Cl$_2$]$_2$), ruthenium chloride (III) hydrate(RuCl$_3$.xH$_2$O), dipivaloyloxy(p-cymene) ruthenium (II)).

The amount of the metal catalyst to be used is generally 0.00001 equivalents-10 equivalents, preferably, 0.001 equivalents-0.3 equivalents, more preferably, 0.003 equivalents-0.015 equivalents, relative to 2-phenylazole derivative [1].

Examples of the base include potassium carbonate (K$_2$CO$_3$), sodium carbonate (Na$_2$CO$_3$), sodium hydrogen carbonate (NaHCO$_3$), potassium hydrogen carbonate (KHCO$_3$), potassium phosphate (K$_3$PO$_4$), cesium carbonate (Cs$_2$CO$_3$), rubidium carbonate (Rb$_2$CO$_3$) and the like. Preferred is potassium carbonate.

The amount of the base to be used is generally 0.1 equivalents-10 equivalents, preferably, 0.1 equivalents-3 equivalents, more preferably, 0.3 equivalents-2 equivalents, relative to 2-phenylazole derivative [1].

While (a) monocarboxylic acid metal salt of the present invention is not particularly limited, for example, a carboxylic acid metal salt represented by RCO$_2$M and the like can be mentioned.

R is a hydrogen atom, or a straight chain or branched chain alkyl group having 1-20 carbon atoms, an aralkyl group having 7-14 carbon atoms, an aryl group having 6-18 carbon atoms or a cycloalkyl group having 3-7 carbon atoms, each of which optionally contains a nitrogen atom, an oxygen atom or a sulfur atom, and the alkyl group, aralkyl group, cycloalkyl group and aryl group optionally have substituent(s). R is preferably a straight chain or branched chain alkyl group having 1-12 carbon atoms (e.g., methyl, tert-butyl, 2-ethyl-hexyl, n-dodecyl), an aralkyl group having 7-10 carbon atoms, an aryl group having 6-12 carbon atoms optionally substituted by an alkyl group having 1-6 carbon atoms (e.g., mesityl), or a cycloalkyl group having 3-7 carbon atoms (e.g., cyclohexyl), particularly preferably, a methyl group or a tert-butyl group.

M is a metal atom, which is preferably Li (lithium), Na (sodium), K (potassium), Rb (rubidium), Cs (cesium), Mg (magnesium) or Zn (zinc), more preferably an alkali metal atom, particularly preferably K.

Preferable examples of the monocarboxylic acid metal salt include a potassium salt of carboxylic acid wherein R is a straight chain or branched chain alkyl group having 1-12 carbon atoms (e.g., methyl, tert-butyl, 2-ethyl-hexyl, n-dodecyl), a cycloalkyl group having a having 3-7 carbon atoms (e.g., cyclohexyl), or an aryl group having 6-12 carbon atoms (e.g., mesityl) optionally substituted by an alkyl group having 1-6 carbon atoms, and an acetic acid potassium salt or a pivalic acid potassium salt is particularly preferable.

While (b) dicarboxylic acid metal salt of the present invention is not particularly limited, for example, a metal salt of dicarboxylic acid represented by

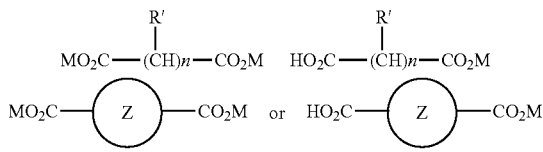

and the like can be mentioned.

R' is a hydrogen atom, or a straight chain or branched chain alkyl group having 1-10 carbon atoms, an aralkyl group having 7-14 carbon atoms or an aryl group having 6-18 carbon atoms, each of which optionally contains a nitrogen atom, an oxygen atom or a sulfur atom. The alkyl group, aralkyl group and aryl group optionally have substituent(s). R' is preferably a hydrogen atom, or a straight chain or branched chain alkyl group having 1-6 carbon atoms, an aralkyl group having 7-10 carbon atoms, or an aryl group having 6-12 carbon atoms, and particularly preferable a hydrogen atom.

n is an integer of 0-10, preferably, an integer of 0-5, particularly preferably, 0 or 3.

Ring Z is cycloalkylene having 3-8 carbon atoms, cycloalkenylene having 3-8 carbon atoms, arylene, or heterocyclylene, preferably, phenylene, naphthylene, anthrylene, phenanthrylene or the like.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of a dicarboxylic acid metal salt is a potassium salt of dicarboxylic acid wherein R' is a hydrogen atom and n is an integer of 0-5, and an oxalic acid potassium salt and a glutaracid potassium salt are particularly preferable.

While (c) sulfonic acid metal salt of the present invention is not particularly limited, for example, a sulfonic acid metal salt represented by R"SO$_3$M and the like can be mentioned.

R" is a hydrogen atom, or a straight chain or branched chain alkyl group having 1-10 carbon atoms, an aralkyl group having 7-14 carbon atoms or an aryl group having 6-18 carbon atoms, each of which optionally contains a nitrogen atom, an oxygen atom or a sulfur atom. The alkyl group, aralkyl group and aryl group optionally have substituent(s). Preferred are a straight chain or branched chain alkyl group having 1-6 carbon atoms, an aralkyl group having 7-10 carbon atoms, and an aryl group having 6-12 carbon atoms (e.g., 2,4,6-trimethylphenyl or 4-dodecylphenyl) which is optionally substituted by an alkyl group having 1-12 carbon atoms, and particularly preferred is a 4-dodecylphenyl group.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of (c) a sulfonic acid metal salt of the present invention is a potassium salt of sulfonic acid wherein R" is a phenyl group optionally substituted by an alkyl group having 1-12 carbon atoms, and potassium 4-dodecylbenzenesulfonate is particularly preferable.

R''' of (d) phosphate or phosphoric amide metal salt represented by R$^4$$_x$P(O) (OM)$_y$, wherein R$^4$ is R'''O or R'''$_2$N of the present invention is a hydrogen atom, or a straight chain or branched chain alkyl group having 1-20, preferably 1-12, carbon atoms, an aralkyl group having 7-14 carbon atoms or an aryl group having 6-18, preferably 6-12, carbon atoms, each of which optionally contains a nitrogen atom, an oxygen atom or a sulfur atom. The alkyl group, aralkyl group and aryl group optionally have substituent(s). Two R''' may form a ring in a molecule. Preferred are a straight chain or branched chain alkyl group having 1-12 carbon atoms (e.g., ethyl, n-butyl, t-butyl, dodecyl, 2-ethyl-n-hexyl), an aralkyl group having 7-10 carbon atoms and an aryl group having 6-12 carbon atoms (e.g., 2-naphthyl), and particularly preferred is a 2-ethyl-n-hexyl group.

x and y are each independently an integer of 1 or 2, and x+y is 3.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of (d) phosphate or phosphoric amide metal salt represented by $R^4{}_xP(O)(OM)_y$ wherein $R^4$ is R'''O or R'''$_2$N of the present invention is a potassium salt of phosphate or a potassium salt of phosphoric amide wherein R''' is a straight chain or branched chain alkyl group having 1-12 carbon atoms (e.g., ethyl, n-butyl, t-butyl, dodecyl, 2-ethyl-n-hexyl) or an aryl group having 6-12 carbon atoms (e.g., 2-naphthyl), and potassium bis(2-ethyl-n-hexyl)phosphate is particularly preferable.

In another embodiment, R''' of (d) phosphate metal salt represented by $(R'''O)_xP(O)(OM)_y$ of the present invention is a hydrogen atom, or a straight chain or branched chain alkyl group having 1-20, preferably 1-12, carbon atoms, an aralkyl group having 7-14 carbon atoms or an aryl group having 6-18, preferably 6-12, carbon atoms, each of which optionally contains a nitrogen atom, an oxygen atom or a sulfur atom. The alkyl group, aralkyl group and aryl group optionally have substituent(s). Two R''' may form a ring in a molecule. Preferred are a straight chain or branched chain alkyl group having 1-12 carbon atoms (e.g., ethyl, n-butyl, t-butyl, dodecyl, 2-ethyl-n-hexyl), an aralkyl group having 7-10 carbon atoms and an aryl group having 6-12 carbon atoms (e.g., 2-naphthyl), and particularly preferred is a 2-ethyl-n-hexyl group.

x and y are each independently an integer of 1 or 2, and x+y is 3.

M is a metal atom, preferably, Li (lithium), Na (sodium), K (potassium), Rb (rubidium), Cs (cesium), Mg (magnesium) or Zn (zinc), more preferably, an alkali metal atom, particularly preferably, K.

A preferable example of (d) phosphate metal salt represented by $(R'''O)_xP(O)(OM)_y$ of the present invention is a potassium salt of phosphate wherein R''' is a straight chain or branched chain alkyl group having 1-12 carbon atoms (e.g., ethyl, n-butyl, t-butyl, dodecyl, 2-ethyl-n-hexyl) or an aryl group having 6-12 carbon atoms (e.g., 2-naphthyl), and potassium bis(2-ethyl-n-hexyl)phosphate is particularly preferable.

Among the aforementioned (a)-(d), (d) $R^4{}_xP(O)(OM)_y$ is preferably used, and a phosphate metal salt represented by $(R'''O)_xP(O)(OM)_y$ is more preferably used, since the yield becomes higher.

The amount of one or more kinds of compounds selected from the group consisting of (a)-(d) to be used is generally 0.00001 equivalents-10 equivalents, preferably, 0.001 equivalents-8.0 equivalents, more preferably, 0.005 equivalents-5.0 equivalents, relative to 2-phenylazole derivative [1].

A method of adding a metal catalyst, a base and one or more kinds of compounds selected from the group consisting of (a)-(d) is not particularly limited, and a method including adding a base and one or more kinds of compounds selected from the group consisting of (a)-(d), and then adding a metal catalyst, a method including adding a base, and then adding a ruthenium catalyst prepared from a metal catalyst and one or more kinds of compounds selected from the group consisting of (a)-(d) and the like can be mentioned.

For preferable progress of the reaction, the reaction may be performed in the further presence of a phosphine compound. Examples of the phosphine compound include a compound represented by the formula [X2]: $PR_3$ wherein R is an alkyl group, an aralkyl group or an aryl group.

Specific examples thereof include triphenylphosphine (sometimes referred to as triphenylphosphane), tri(t-butyl) phosphine, triethylphosphine, tricyclohexylphosphine, tri(o-tolyl)phosphine, tri(p-tolyl)phosphane, tri(p-methoxyphenyl)phosphane, cyclohexyldiphenylphosphane and the like, with preference given to triphenylphosphine.

The amount of the phosphine compound to be used is generally 0.00001 equivalents-10 equivalents, preferably, 0.001 equivalents-1 equivalent, relative to 2-phenylazole derivative [1].

In addition, the reaction may be performed in the presence of a conjugate acid of a metal salt described in the above-mentioned (a)-(d).

The amount of the conjugate acid to be used is generally 0.00001 equivalents-3 equivalents, preferably, 0.05 equivalents-1.0 equivalents, more preferably, 0.1 equivalents-0.5 equivalents, relative to 2-phenylazole derivative [1].

While the solvent is not particularly limited as long as the reaction proceeds, polar solvents such as N-methyl-2-pyrrolidone (sometimes to be abbreviated as NMP), N,N-dimethylformamide (sometimes to be abbreviated as DMF), N,N-dimethylacetamide (sometimes to be abbreviated as DMA), dimethyl sulfoxide (sometimes to be abbreviated as DMSO) and the like, non-polar solvents such as toluene, xylene and the like, and a mixture of the polar solvent and the non-polar solvent are preferable.

The amount of the solvent to be used is generally 0 mL-100 mL, preferably, 0.1 mL-10 mL, per 1 mmol of 2-phenylazole derivative [1].

The reaction temperature is generally 20° C.-300° C., preferably, 100° C.-200° C.

The reaction time is generally 0.01 hr-200 hr, preferably, 0.5 hr-24 hr.

[Production Method 2]

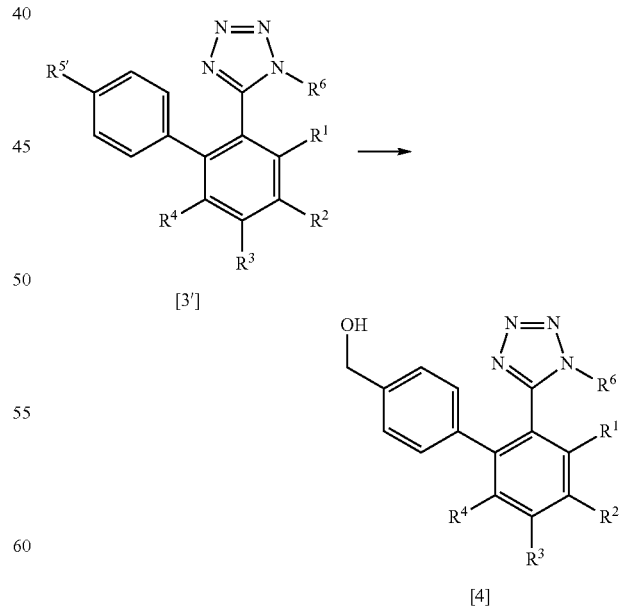

(Step 2a)

When $R^{5'}$ of biaryltetrazole compound [3'] is a methyl group substituted by a protected hydroxyl group, compound

[4] can be produced by deprotecting biaryltetrazole compound [3'] in the presence of a base or an acid. This reaction can also be performed in a solvent.

As the base, sodium hydroxide, potassium hydroxide, sodium methoxide, sodium ethoxide, dimethylamine, methylamine, ammonia, potassium carbonate, sodium carbonate and the like can be mentioned. The amount of the base to be used is generally 0.001 equivalents-10 equivalents, preferably, 0.01 equivalents-1 equivalent, relative to biaryltetrazole compound [3'].

As the acid, hydrobromic acid, hydrogen chloride and the like can be mentioned. The amount of the acid to be used is generally 1 equivalent-10000 equivalents, preferably, 1 equivalent-100 equivalents, relative to biaryltetrazole compound [3'].

The solvent is not particularly limited as long as the reaction proceeds, and methanol, ethanol, propanol, tetrahydrofuran (sometimes to be abbreviated as THF) and the like can be mentioned. For deprotection in the presence of an acid, acetic acid and the like can also be used. A mixed solvent of these solvents and water may also be used. The amount of the solvent to be used is generally 0.01 mL-100 mL, preferably, 0.1 mL-10 mL, per 1 mmol of biaryltetrazole compound [3'].

The reaction temperature is generally −50° C.-100° C., preferably, 10° C.-40° C.

The reaction time is generally 0.001 hr-50 hr, preferably, 0.1 hr-20 hr.

When the hydroxyl-protecting group is a group (e.g., benzoyl group) deprotected with an acid and hydrogen halide or hydrohalic acid is used, step 2a (deprotection step) and the below-mentioned step 3 (halogenation step) can also be performed simultaneously.

(Step 2b)

When $R^{5'}$ of biaryltetrazole compound [3'] is a lower alkoxycarbonyl group, compound [4] can be produced by reducing biaryltetrazole compound [3'] in the presence of a reducing agent. This reaction can also be performed in a solvent.

As the reducing agent, sodium borohydride (also called sodium tetrahydroborate), lithium aluminum hydride, diisobutylaluminum hydride and the like can be mentioned. The amount of the reducing agent to be used is generally 1 equivalent-5 equivalents, preferably, 1 equivalent-2 equivalents, relative to biaryltetrazole compound [3'].

For preferable progression of the reaction, a metal salt can be added. As the metal salt, calcium chloride, zinc chloride and the like can be mentioned. The amount of the metal salt to be used is generally 0.1 equivalents-2 equivalents, preferably, 0.5 equivalents-1 equivalent, relative to biaryltetrazole compound [3']. When lithium aluminum hydride or diisobutylaluminum hydride is used as a reducing agent, the reaction proceeds in the absence of a metal salt.

The solvent is not particularly limited as long as the reaction proceeds, and ethanol, 2-propanol, methanol and the like can be mentioned. The amount of the solvent to be used is generally 1 mL-50 mL, preferably, 1 mL-2 mL, per 1 mmol of biaryltetrazole compound [3'].

The reaction temperature is generally −50° C.-120° C., preferably, 0° C.-80° C.

The reaction time is generally 0.1 hr-24 hr, preferably, 3 hr-10 hr.

(Step 3)

1-A) when $R^{5'}$ is methyl group or lower alkoxycarbonyl group substituted by protected hydroxyl group

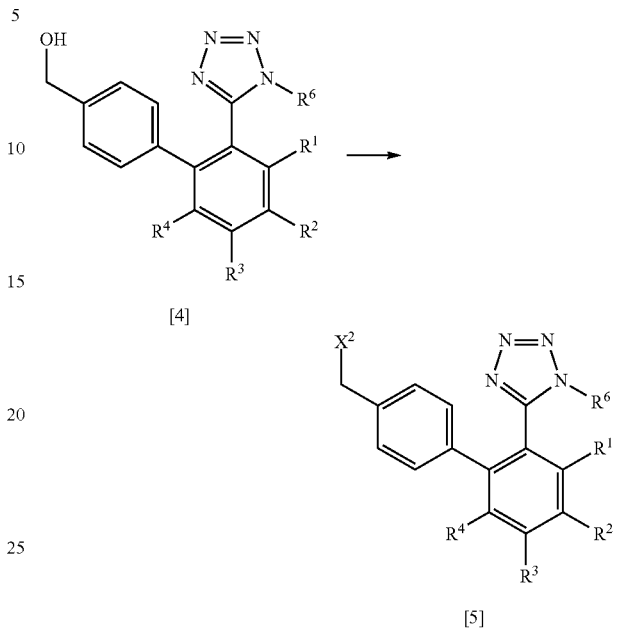

1-B) when $R^{5'}$ is methyl group

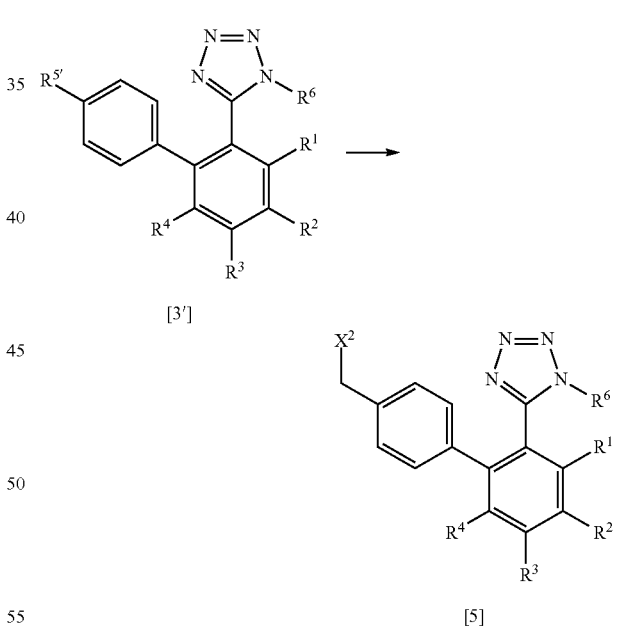

When $R^{5'}$ of biaryltetrazole compound [3'] is a methyl group, biaryltetrazole derivative [5] can be produced by reacting biaryltetrazole compound [3'] with a halogenating reagent in the presence of azobisisobutyronitrile (AIBN).

When $R^{5'}$ of biaryltetrazole compound [3'] is a methyl group or lower alkoxycarbonyl group substituted by protected hydroxyl group, biaryltetrazole derivative [5] can be produced by reacting compound [4] with a halogenating reagent.

These reactions can also be performed in a solvent.

While the halogenating reagent is not particularly limited, a halogenating reagent known per se can be applied. For example, phosphorus tribromide, thionyl bromide, hydrobromic acid, hydrogen chloride, thionyl chloride, carbon tetrachloride/triphenylphosphine, bromotrimethylsilane, N-bromosuccinimide (NBS) and the like can be mentioned. The amount of the halogenating reagent to be used is generally 1 equivalent-10 equivalents, preferably, 1 equivalent-3 equivalents, relative to biaryltetrazole compound [3'] or compound [4].

The solvent is not particularly limited as long as the reaction proceeds, and THF, toluene, ethyl acetate, dioxane, methyl t-butyl ether (MTBE), chloroform, methylene chloride, diisopropyl ether, acetonitrile, acetic acid and the like can be mentioned. The amount of the solvent to be used is generally 0.01 mL-100 mL, preferably, 0.1 mL-10 mL, per 1 mmol of biaryltetrazole compound [3'] or compound [4].

The reaction temperature is generally −50° C.-150° C., preferably, −20° C.-50° C.

The reaction time is generally 0.001 hr-24 hr, preferably, 0.1 hr-10 hr.

[Production Method 3] and [Production Method 3'] (Olmesartan Production Method)

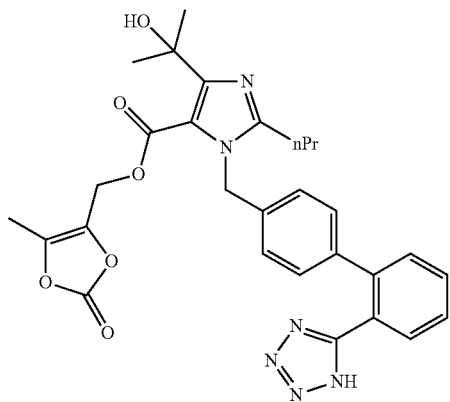

(Olmesartan)

Olmesartan or a salt thereof can be produced from biaryltetrazole derivative [5'] by a known method described in JP-B-7-121918, JP-A-2010-505926 and the like. In addition, it can also be produced by the following method.

(Step 1)

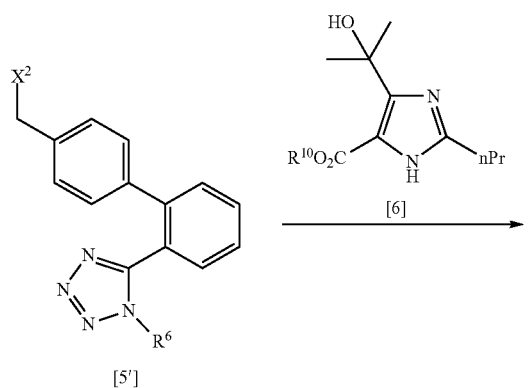

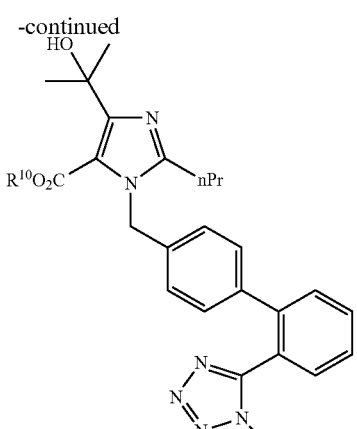

Compound [7] can be produced by reacting biaryltetrazole derivative [5'] obtained in the aforementioned Production method 2 with compound [6] in the presence of a base. This reaction can also be performed in a solvent.

The base is not particularly limited, and a base known per se can be applied. For example, potassium carbonate, cesium carbonate, sodium hydroxide, potassium hydroxide, triethylamine, diisopropylethylamine, 1,8-diazabicyclo[5.4.0]undec-7-ene (DBU) and the like can be mentioned. The amount of the base to be used is generally 1 equivalent-10 equivalents, preferably, 1 equivalent-3 equivalents, relative to biaryltetrazole derivative [5'].

The solvent is not particularly limited as long as the reaction proceeds, and DMA, DMF, DMSO, NMP, acetonitrile, toluene, THF, dioxane, acetone and the like can be mentioned. The amount of the solvent to be used is generally 0.001 mL-100 mL, preferably, 0.1 mL-10 mL, per 1 mmol of biaryltetrazole derivative [5'].

The reaction temperature is generally −50° C.-150° C., preferably, 20° C.-50° C.

The reaction time is generally 0.1 hr-48 hr, preferably, 0.5 hr-5 hr.

$R^{10}$ of compound [6] and compound [7] in this step is preferably a linear or branched chain alkyl group having 1-6 carbon atoms, more preferably an alkyl group having 1-3 carbon atoms, further preferably a methyl group or an ethyl group.

(Step 2)

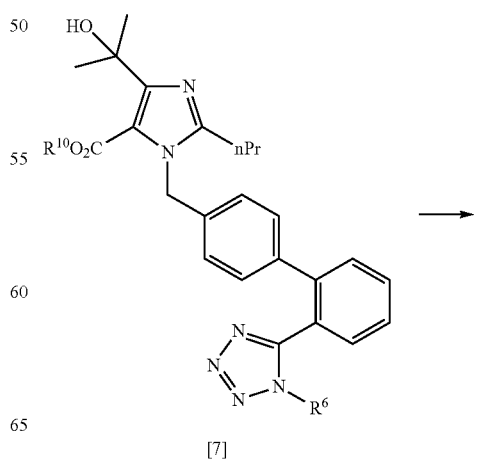

-continued

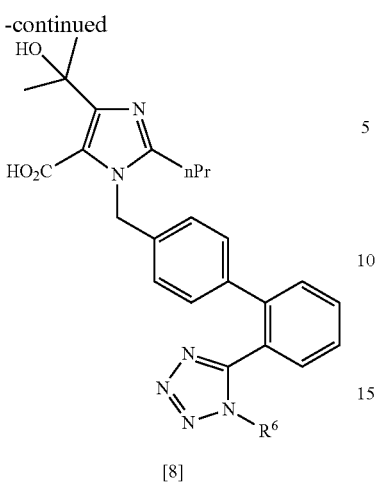

[8]

Compound [8] can be produced by hydrolyzing compound [7], in the presence of a base or an acid, and a water-soluble organic solvent.

The base is not particularly limited, and the bases known per se can be applied. For example, potassium hydroxide, potassium carbonate, sodium hydroxide, sodium hydride and the like can be mentioned. The acid is not particularly limited, and an acid known per se can be applied. For example, trifluoroacetic acid, trichloroacetic acid, trifluoromethanesulfonic acid, methanesulfonic acid, sulfuric acid, hydrochloric acid and the like can be mentioned. The amount of the base or acid to be used is generally 1 equivalent-10 equivalents, preferably, 1 equivalent-3 equivalents, relative to compound [7].

As the water-soluble organic solvent, methanol, ethanol, acetone and the like can be mentioned. The amount of the solvent to be used is generally 0.001 mL-100 mL, preferably, 0.1 mL-10 mL, per 1 mmol of compound [7].

The reaction temperature is generally 0° C.-120° C., preferably, 30° C.-100° C.

The reaction time is generally 0.1 hr-48 hr, preferably, 0.5 hr-10 hr.

$R^{10}$ of compound [7] in this step is preferably a linear or branched chain alkyl group having 1-6 carbon atoms, more preferably an alkyl group having 1-3 carbon atoms, further preferably a methyl group or an ethyl group.

(Step 2')

Another embodiment of (step 2) is the following step.

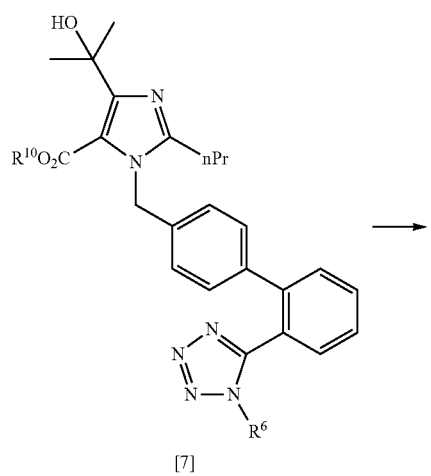

[7]

-continued

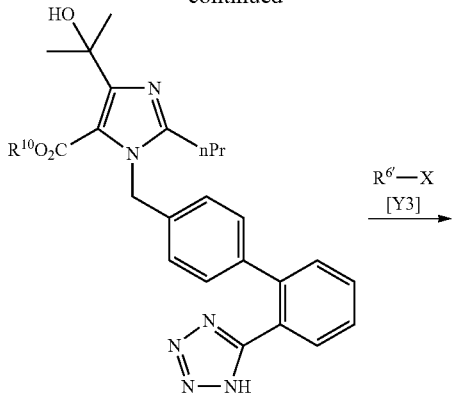

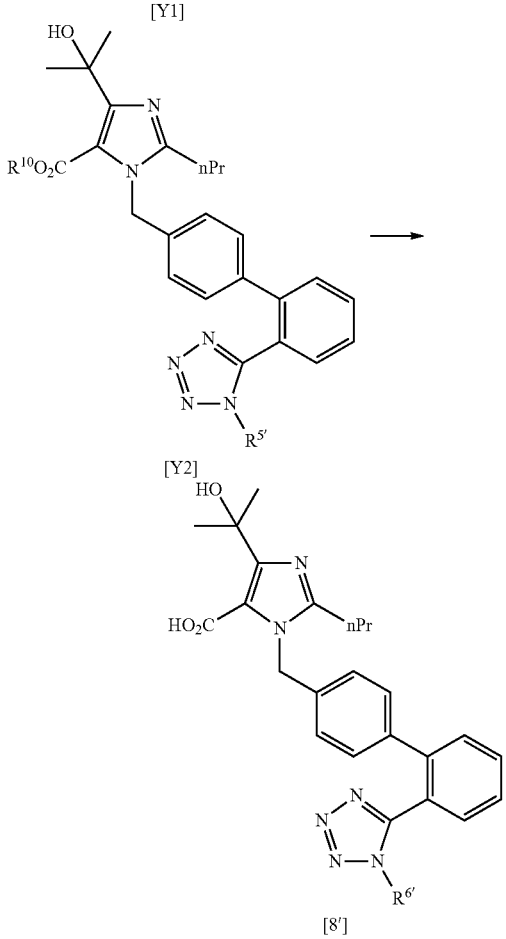

[8']

(Step 2'-1)

Compound [Y1] can be produced by removing $R^6$ of compound [7]. This reaction can also be performed in a solvent.

For removal of $R^6$, an acid can be used. The acid is not particularly limited, and an acid known per se can be applied. For example, trifluoroacetic acid, trichloroacetic acid, trifluoromethanesulfonic acid, methanesulfonic acid, sulfuric acid, hydrochloric acid, acetic acid and the like can be mentioned. The amount of the acid to be used is generally 0.1 equivalents-1000 equivalents, preferably, 1 equivalent-500 equivalents, relative to compound [7].

Removal of $R^6$ by an acid can be preferably performed in the presence of a scavenger. While the scavenger is not particularly limited as long as the reaction proceeds, mercaptans such as anisole, mesitylene, 1-octanethiol and the like, and the like can be mentioned. The amount of the scavenger to be used is generally 0.001 mL-10 mL, preferably, 0.1 mL-5 mL, per 1 mmol of compound [7].

The above-mentioned acid or scavenger may act as a solvent in this step.

The reaction temperature is generally −50° C.-150° C., preferably, 10° C.-100° C.

The reaction time is generally 0.1 hr-48 hr, preferably, 0.5 hr-20 hr.

For removal of $R^6$, a method including reduction (e.g., catalytic reduction, formic acid reduction etc.) can also be used. This reaction can also be performed in a solvent.

Reduction can be performed in the presence of a catalyst. The catalyst is not particularly limited as long as it can be used for catalytic reduction or formic acid reduction. For example, palladium catalysts such as palladium/barium sulfate, palladium carbon, palladium black, palladium oxide, palladium chloride, palladium acetate and the like can be mentioned. The amount of the catalyst to be used is generally 0.0001 equivalents-10 equivalents, preferably, 0.01 equivalents-0.1 equivalents, relative to compound [7].

This reaction can also be performed under basic condition of pH 7-14, or pH7.

In the case of catalytic reduction, the hydrogen pressure is 1 atm-100 atm, preferably, 1 atm-10 atm.

In the case of formic acid reduction, formic acid or formic acid salt (ammonium formate etc.) is added as an additive.

The solvent is not particularly limited as long as the reaction proceeds, and alcohols such as isopropyl alcohol, n-propyl alcohol, methanol, ethanol and the like, tetrahydrofuran, methylene chloride, ethyl acetate and the like, or a mixed solvent of the above-mentioned solvent and water can be mentioned. The amount of the solvent to be used is generally 0.1 mL-100 mL, preferably, 0.5 mL-10 mL, per 1 mmol of compound [7].

The reaction temperature is generally 0° C.-150° C., preferably, 10° C.-80° C.

The reaction time is generally 0.1 hr-72 hr, preferably, 0.5 hr-24 hr.

$R^6$ of compound [7] in this step is preferably a benzyl group, and $R^6$ is preferably removed by reaction in the presence of ammonium formate, a palladium catalyst and alcohol.

$R^{10}$ of compound [7], compound [Y1] and compound [Y2] in this step is preferably a linear or branched chain alkyl group having 1-6 carbon atoms, more preferably an alkyl group having 1-3 carbon atoms, further preferably a methyl group or an ethyl group.

(Step 2'-2)

Compound [Y2] can be produced by reacting compound [Y1] with compound [Y3] in the presence of a base. This reaction can also be performed in a solvent.

The base is not particularly limited, and the bases known per se can be applied. For example, triethylamine, N,N-diisopropylethylamine, pyridine, lutidine, sodium carbonate, potassium carbonate, cesium carbonate and the like can be mentioned. Preferred is triethylamine. The amount of the base to be used is generally 0.1 equivalents-10 equivalents, preferably, 1 equivalent-5 equivalents, relative to compound [Y1].

The solvent is not particularly limited as long as the reaction proceeds, and methylene chloride, chloroform, toluene, acetone, tetrahydrofuran, ethyl acetate, N,N-dimethylformamide and the like can be mentioned. The amount of the solvent to be used is generally 0.01 mL-50 mL, preferably, 0.5 mL-5 mL, per 1 mmol of compound [Y1].

The reaction temperature is generally −10° C.-50° C., preferably, −5° C.-40° C.

The reaction time is generally 0.1 hr-48 hr, preferably, 1 hr-24 hr.

(Step 2'-3)

Compound [8'] can be produced using compound [Y2] and in the same manner as in the method described in the above-mentioned step 2.

In this step, hydrolysis is preferably performed in the presence of a base.

(Step 3)

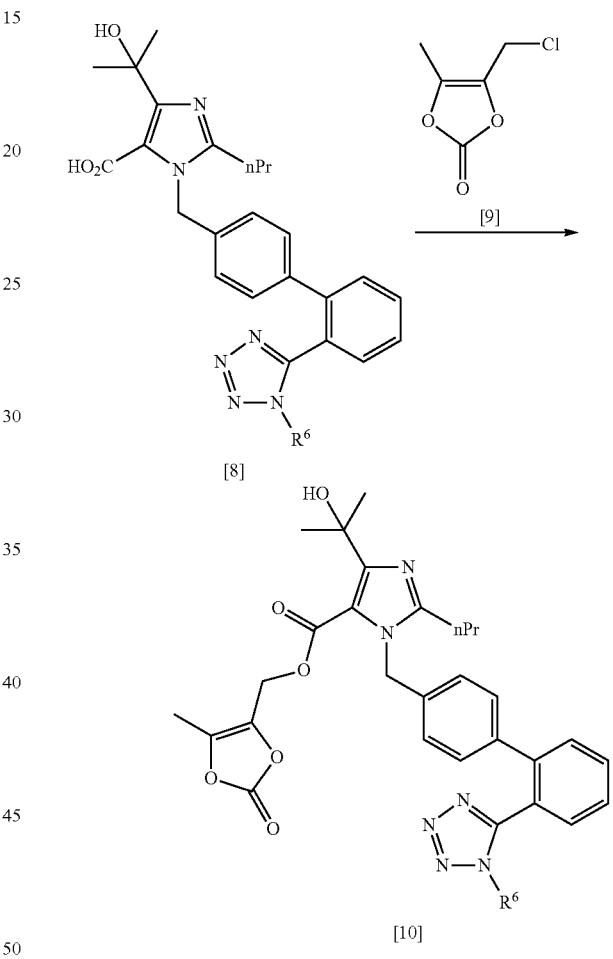

Compound [10] can be produced by reacting compound [8] with compound [9] in the presence of a base.

The base is not particularly limited, and the bases known per se can be applied. For example, potassium carbonate, cesium carbonate, sodium hydroxide, potassium hydroxide, triethylamine, diisopropylethylamine, 1,8-diazabicyclo[5.4.0]undec-7-ene (DBU) and the like can be mentioned. The amount of the base to be used is generally 1 equivalent-10 equivalents, preferably, 1 equivalent-3 equivalents, relative to compound [8].

The solvent is not particularly limited as long as the reaction proceeds, and DMA, DMF, DMSO, NMP, acetonitrile, toluene, THF, dioxane, acetone and the like can be mentioned. The amount of the solvent to be used is generally 0.001 mL-100 mL, preferably, 0.1 mL-10 mL, per 1 mmol of compound [8].

The reaction temperature is generally 0° C.-150° C., preferably, 30° C.-100° C.

The reaction time is generally 0.1 hr-48 hr, preferably, 0.5 hr-24 hr.
(Step 3')

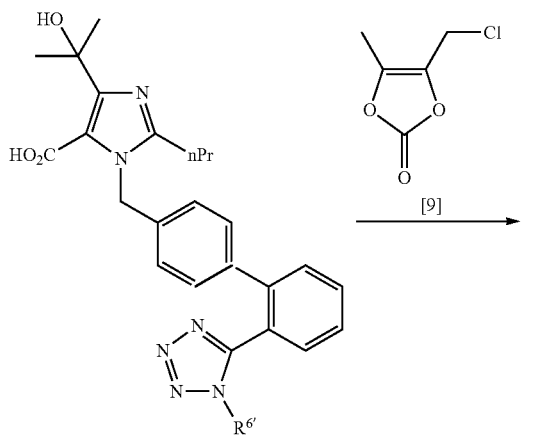

[8']

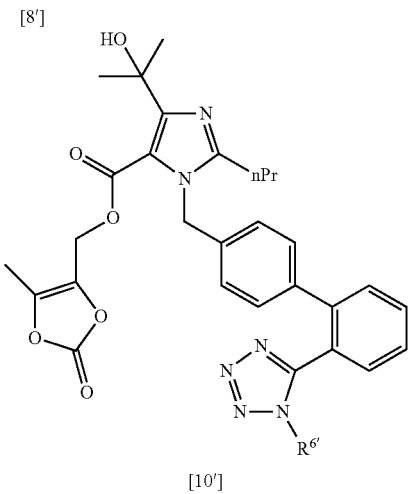

[10']

Compound [10'] can be produced using compound [8'] and in the same manner as in the method described in the above-mentioned step 3.
(Step 4)

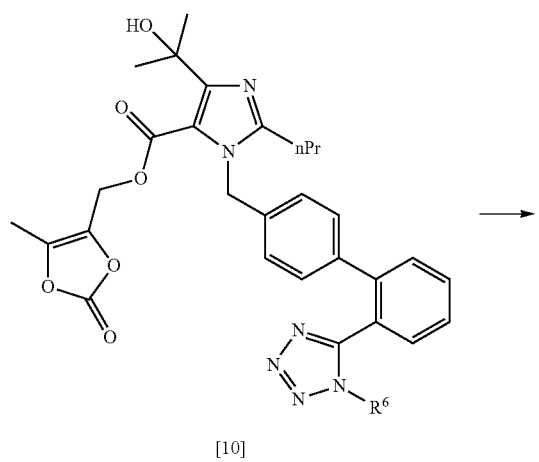

[10]

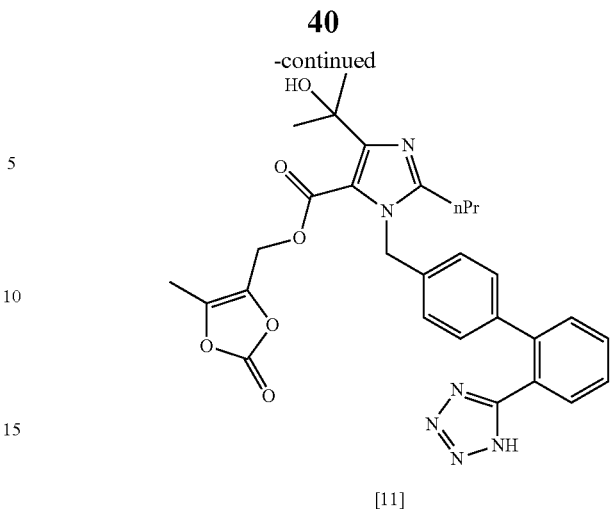

[11]

Compound [11] (olmesartan or a salt thereof) can be produced by removing $R^6$ of compound [10]. This reaction can also be performed in a solvent.

To remove $R^6$, an acid can be used. The acid is not particularly limited, acids known per se can be applied. For example, trifluoroacetic acid, trichloroacetic acid, trifluoromethanesulfonic acid, methanesulfonic acid, sulfuric acid, hydrochloric acid, acetic acid and the like can be mentioned. The amount of the acid to be used is generally 0.1 equivalents-1000 equivalents, preferably, 1 equivalent-500 equivalents, relative to compound [10].

Removal of $R^6$ by an acid can be preferably performed in the presence of a scavenger. While the scavenger is not particularly limited as long as the reaction proceeds, mercaptans such as anisole, mesitylene, 1-octanethiol and the like, and the like can be mentioned. The amount of the scavenger to be used is generally 0.001 mL-10 mL, preferably, 0.1 mL-5 mL, per 1 mmol of compound [10].

The above-mentioned acid or scavenger may act as a solvent in this step.

The reaction temperature is generally −50° C.-150° C., preferably, 10° C.-100° C.

The reaction time is generally 0.1 hr-48 hr, preferably, 0.5 hr-20 hr.

For removal of $R^6$, a method including reduction (e.g., catalytic reduction, formic acid reduction etc.) can also be used. This reaction can also be performed in a solvent.

Reduction can be performed in the presence of a catalyst. The catalyst is not particularly limited as long as it can be used for catalytic reduction or formic acid reduction. For example, palladium carbon, palladium black, palladium oxide, palladium chloride, palladium acetate and the like can be mentioned. The amount of the catalyst to be used is generally 0.0001 equivalents-10 equivalents, preferably, 0.01 equivalents-0.1 equivalents, relative to compound [10].

This reaction can also be performed under basic condition of pH 7-14, or pH7.

In the case of catalytic reduction, the hydrogen pressure is 1-100 atm, preferably, 1-10 atm.

In the case of formic acid reduction, formic acid or formic acid salt (ammonium formate etc.) is added as an additive.

While the solvent is not particularly limited as long as the reaction proceeds, isopropyl alcohol, n-propyl alcohol, methanol, ethanol, tetrahydrofuran, methylene chloride, ethyl acetate and the like, and a mixed solvent of the above-mentioned solvent and water can be mentioned. The amount of the solvent to be used is generally 0.1 mL-100 mL, preferably, 0.5 mL-10 mL, per 1 mmol of compound [10].

The reaction temperature is generally 0° C.-150° C., preferably, 10° C.-80° C.

The reaction time is generally 0.1 hr-72 hr, preferably, 0.5 hr-24 hr.

(Step 4')

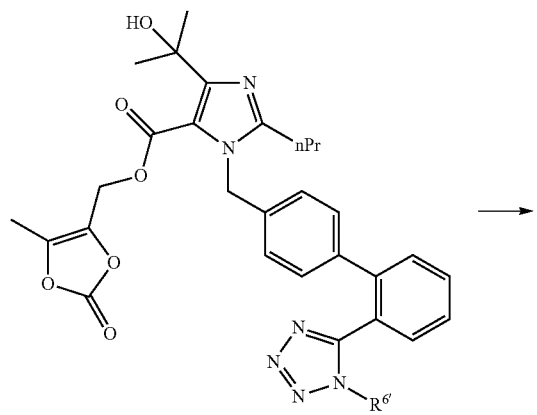

[10']

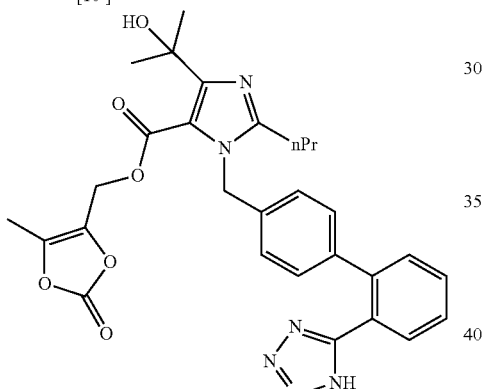

[11]

Compound [11] can be produced using compound [10'] and in the same manner as in the method using an acid, which is described in the above-mentioned step 4.

[Production Method 4] (Losartan Production Method)

(Step 1)

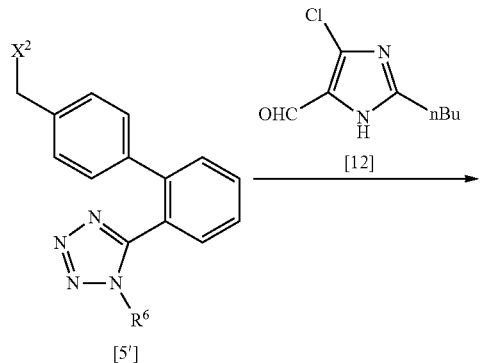

[5']

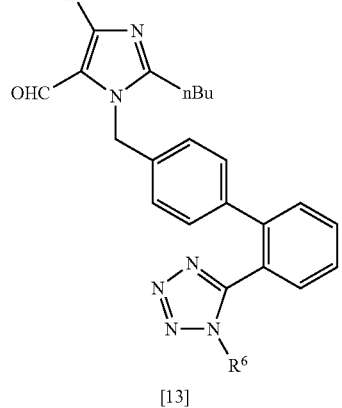

[13]

Compound [13] can be produced by reacting biaryltetrazole derivative [5'] obtained in the aforementioned Production method 2 with compound [12] in the same manner as in the method described in production method 3, step 1.

(step 2-A(1))

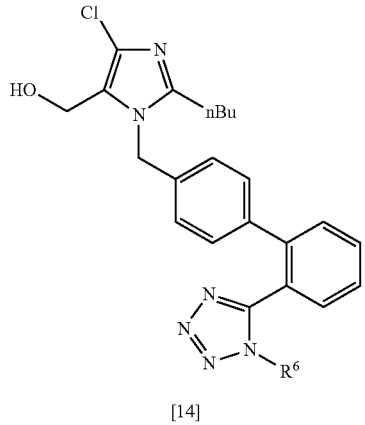

[13]

[14]

Compound [14] can be produced by reducing compound [13] in the presence of a reducing agent. This reaction can also be performed in a solvent.

The reducing agent is not particularly limited, and reducing agents known per se can be applied. For example, sodium borohydride, lithium borohydride, zinc borohydride, sodium triacetoxyborohydride and the like can be mentioned. The amount of the reducing agent to be used is generally 1 equivalent-10 equivalents, preferably, 1 equivalent-5 equivalents, relative to compound [13].

While the solvent is not particularly limited as long as the reaction proceeds, methanol, ethanol, isopropyl alcohol, dimethoxyethane, water and the like can be mentioned. The amount of the solvent to be used is generally 0.01 mL-100 mL, preferably, 0.1 mL-10 mL, per 1 mmol of compound [13].

In this reaction, a base can also be used as necessary. Examples of the base include sodium hydroxide and the like. The amount of the base to be used is generally 0 equivalents-10 equivalents, preferably, 1 equivalent-2 equivalents, relative to compound [13].

The reaction temperature is generally −50° C.-100° C., preferably, 20° C.-50° C.

The reaction time is generally 0.01 hr-48 hr, preferably, 0.1 hr-5 hr.

(Step 2-A(2))

(Step 2-B(1))

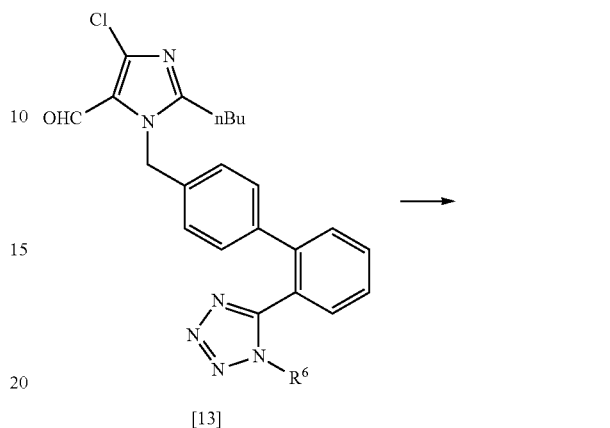

[13]

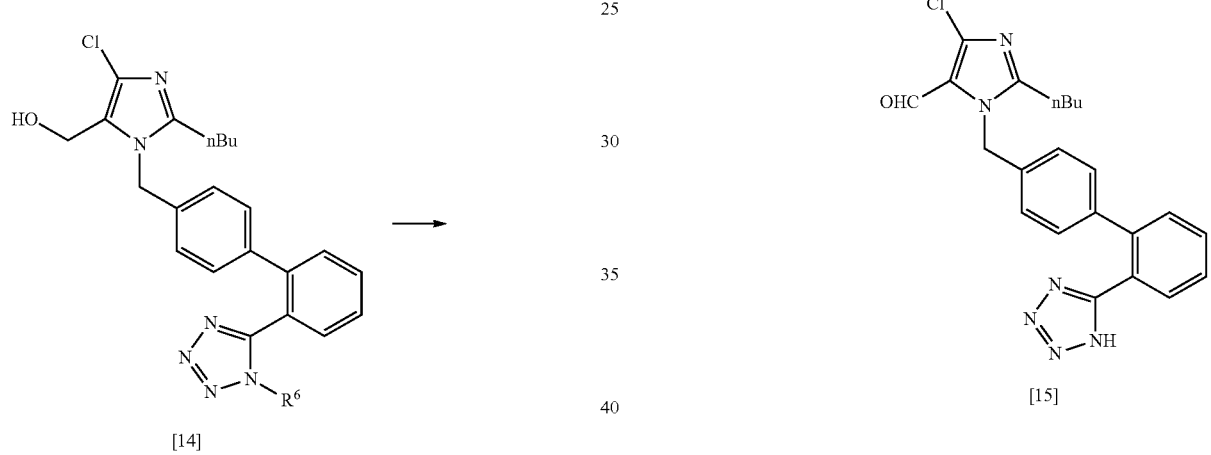

[14]

[15]

Compound [15] can be produced using compound [13] and in the same manner as in the method described in the above-mentioned Production method 3, step 4.

(Step 2-B(2))

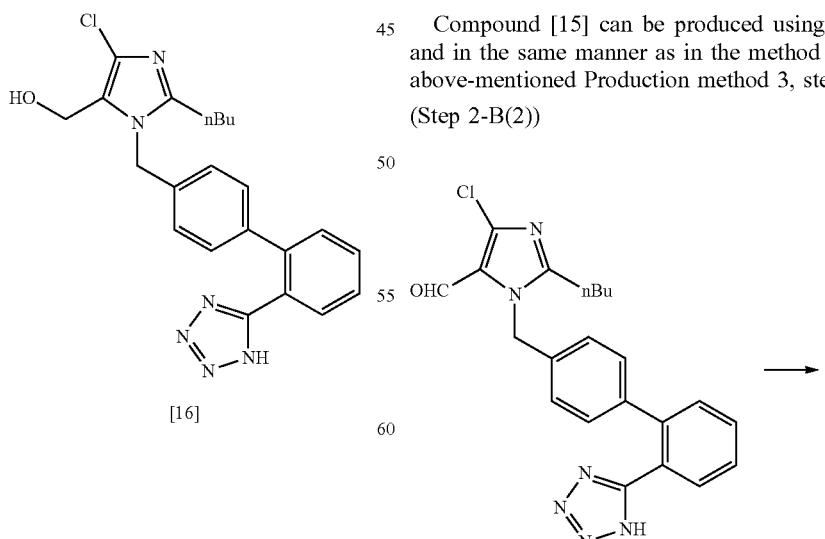

[16]

[15]

Compound [16] can be produced using compound [14] and in the same manner as in the method described in the above-mentioned Production method 3, step 4.

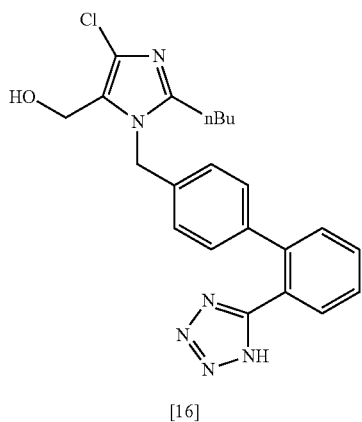

[16]

Compound [16] can be produced by reducing compound [15] in the same manner as in the method described in the above-mentioned step 2-A(1).

[Production Method 5] (Valsartan Production Method)
(Step 1)

triethylamine, pyridine, sodium hydride, potassium t-butoxide and the like can be mentioned. The amount of the base to be used is generally 1 equivalent-10 equivalents, preferably, 1 equivalent-5 equivalents, relative to biaryltetrazole derivative [5'].

In this reaction, a catalyst can also be used as necessary. For example, tetrabutylammonium iodide and the like can be mentioned. The amount of the catalyst to be used is generally 0.01 equivalents-0.5 equivalents, preferably, 0.01 equivalents-0.1 equivalents, relative to biaryltetrazole derivative [5'].

The solvent is not particularly limited as long as the reaction proceeds, and DMF, acetonitrile, toluene, THF, dioxane, chloroform, methylene chloride and the like can be mentioned. The amount of the solvent to be used is generally 0.1 mL-100 mL, preferably, 0.5 mL-5 mL, per 1 mmol of biaryltetrazole derivative [5'].

The reaction temperature is generally −50° C.-150° C., preferably, 5° C.-100° C.

The reaction time is generally 0.1 hr-48 hr, preferably, 0.5 hr-36 hr.

(Step 2-A(1))

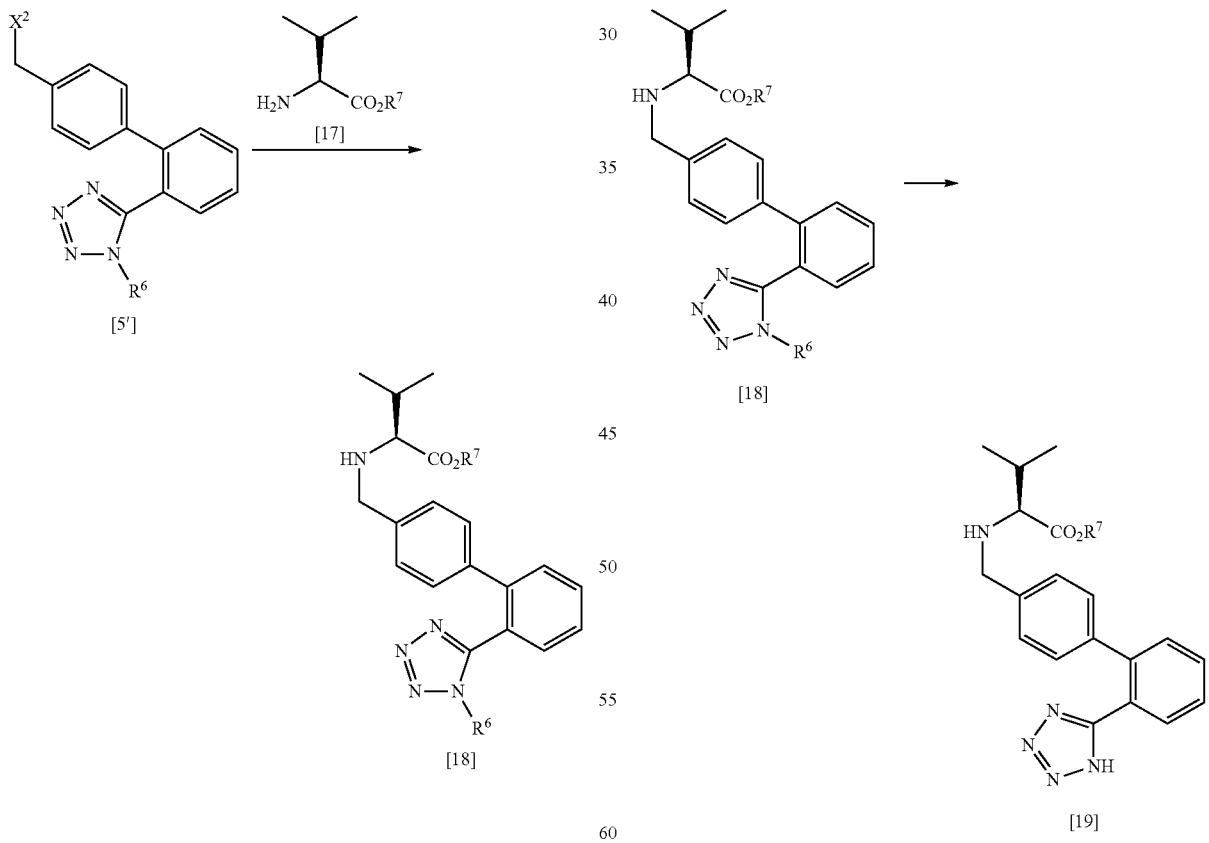

Compound [18] can be produced by reacting biaryltetrazole derivative [5'] obtained in the aforementioned Production method 2 with compound [17] (e.g., p-toluenesulfonate, hydrochloride etc.) in the presence of a base. This reaction can also be performed in a solvent.

The base is not particularly limited, and bases known per se can be applied. For example, diisopropylethylamine, Compound [19] can be produced using compound [18] and in the same manner as in the method described in the above-mentioned Production method 3, step 4.

(Step 2-A(2))

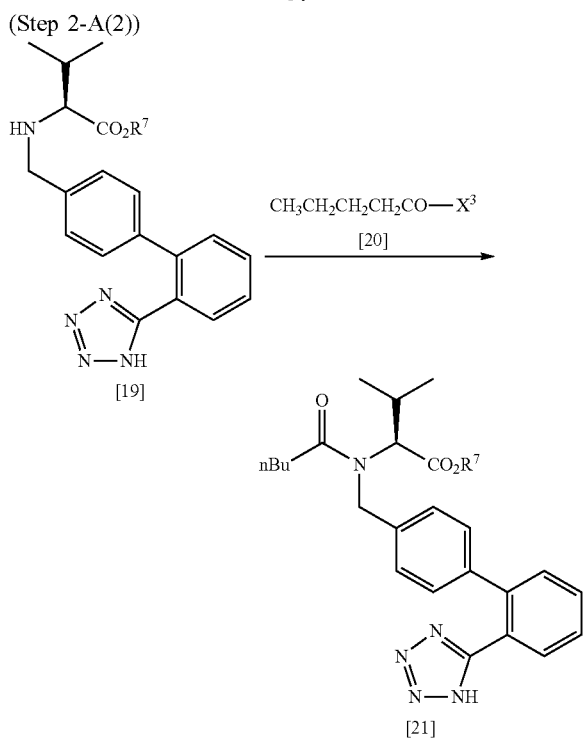

Compound [21] can be produced by reacting compound [19] with compound [20] in the presence of a base. This reaction can also be performed in a solvent.

While the base is not particularly limited, for example, triethylamine, diisopropylethylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP), lutidine, pyridine and the like can be mentioned. The amount of the base to be used is generally 1 equivalent-10 equivalents, preferably, 1 equivalent-3 equivalents, relative to compound [19].

While the solvent is not particularly limited as long as the reaction proceeds, toluene, xylene, methylene chloride, chloroform, acetonitrile, NMP, DMF, DMSO, THF, dimethoxyethane, t-butyl methyl ether (hereinafter to be also referred to as t-BME), 1,4-dioxane and the like can be mentioned. The amount of the solvent to be used is generally 0.001 mL-100 mL, preferably, 0.1 mL-10 mL, per 1 mmol of compound [19].

The reaction temperature is generally −20° C.-150° C., preferably, 0° C.-100° C.

The reaction time is generally 0.1 hr-48 hr, preferably, 0.5 hr-5 hr.

(Step 2-A(3))

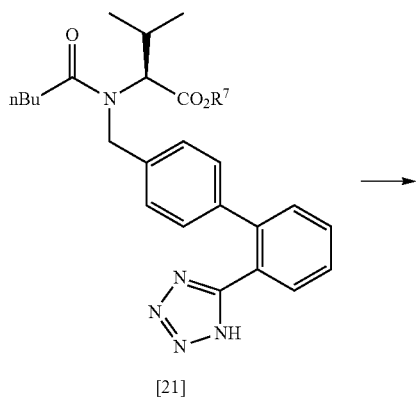

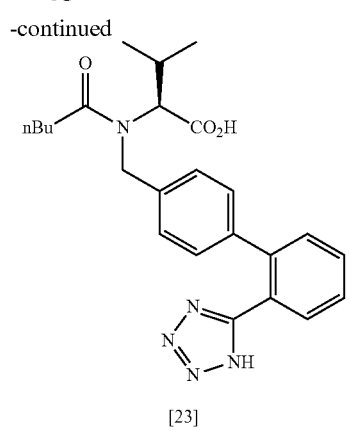

Compound [23] can be produced by removing $R^7$ of compound [21] in the presence of an acid.

The acid is not particularly limited, and an acid known per se can be applied. For example, trifluoroacetic acid, trichloroacetic acid, trifluoromethanesulfonic acid, methanesulfonic acid, sulfuric acid, hydrochloric acid and the like can be mentioned. The amount of the acid to be used is generally 0.1 equivalents-1000 equivalents, preferably, 1 equivalent-500 equivalents, relative to compound [21].

Deprotection by an acid can be preferably performed in the presence of a scavenger. While the scavenger is not particularly limited as long as the reaction proceeds, mercaptans such as anisole, mesitylene and the like, and the like can be mentioned. The amount of the scavenger to be used is generally 0.001 mL-10 mL, preferably, 0.1 mL-5 mL, per 1 mmol of compound [21].

The above-mentioned acid or scavenger may act as a solvent in this step.

The reaction temperature is generally −50° C.-150° C., preferably, 10° C.-100° C.

The reaction time is generally 0.1 hr-48 hr, preferably, 0.5 hr-5 hr.

Alternatively, compound [23] can also be produced by removing $R^7$ of compound [21] in the presence of a base. This reaction can also be performed in a solvent.

As the base, sodium methoxide, sodium ethoxide, dimethylamine, methylamine, ammonia, potassium carbonate, sodium carbonate and the like can be mentioned. The amount of the base to be used is generally 0.001 equivalents-10 equivalents, preferably, 0.01 equivalents-1 equivalent, relative to compound [21].

The solvent is not particularly limited as long as the reaction proceeds, and methanol, ethanol, propanol and the like can be mentioned. The amount of the solvent to be used is generally 0.01 mL-100 mL, preferably, 0.1 mL-10 mL, per 1 mmol of compound [21].

The reaction temperature is generally −50° C.-100° C., preferably, 0° C.-20° C.

The reaction time is generally 0.001 hr-10 hr, preferably, 0.1 hr-5 hr.

Alternatively, compound [23] can also be produced by removing $R^7$ of compound [21] by reduction (e.g., catalytic reduction, formic acid reduction etc.). This reaction can also be performed in a solvent.

Reduction can be performed in the presence of a catalyst. The catalyst is not particularly limited as long as it can be used for catalytic reduction or formic acid reduction. For example, palladium carbon, palladium black, palladium oxide, palladium chloride, palladium acetate and the like can be mentioned. The amount of the catalyst to be used is generally 0.0001 equivalents-10 equivalents, preferably, 0.01 equivalents-0.1 equivalents, relative to compound [21].

In the case of catalytic reduction, the hydrogen pressure is 1 atm-100 atm, preferably, 1 atm-10 atm.

In the case of formic acid reduction, formic acid or formic acid salt (ammonium formate etc.) is added as an additive.

While the solvent is not particularly limited as long as the reaction proceeds, n-propyl alcohol, methanol, ethanol, tetrahydrofuran, methylene chloride, ethyl acetate and the like, and a mixed solvent of the above-mentioned solvent and water can be mentioned. The amount of the solvent to be used is generally 0.1 mL-100 mL, preferably, 0.5 mL-10 mL, per 1 mmol of compound [21].

The reaction temperature is generally 0° C.-150° C., preferably, 10° C.-80° C.

The reaction time is generally 0.1 hr-72 hr, preferably, 0.5 hr-24 hr.

(Step 2-B(1))

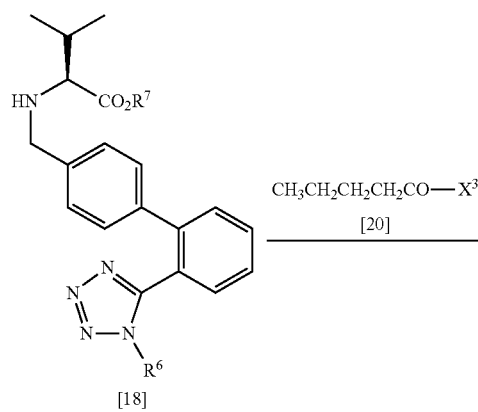

(Step 2-B(2))

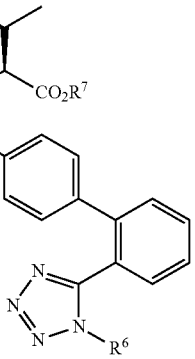

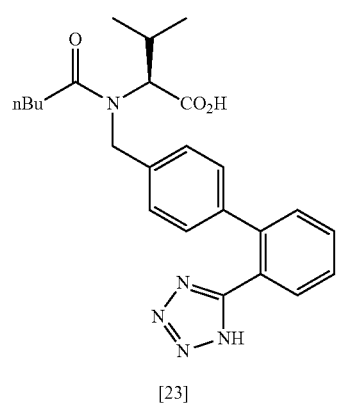

Compound [23] can be produced using compound [22] and in the same manner as in the methods described in the above-mentioned Production method 3, step 4 and the above-mentioned step 2-A(3) (removal of $R^6$ and $R^7$).

[Production Method 6] (Irbesartan Production Method)

(Step 1)

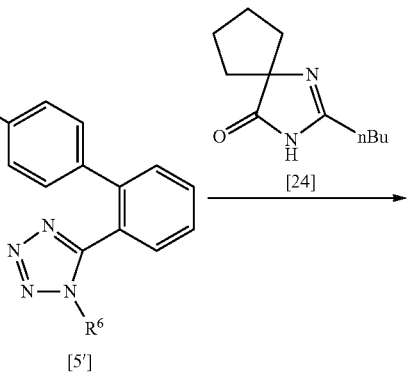

Compound [22] can be produced using compound [18] and in the same manner as in the method described in the above-mentioned step 2-A(2).

-continued

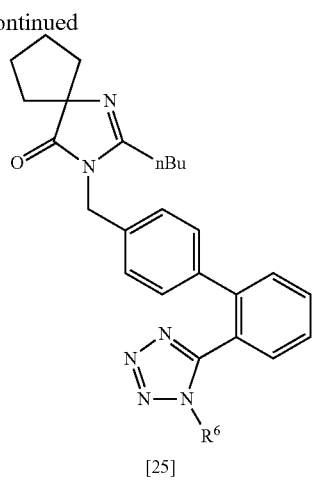

[25]

Compound [25] can be produced by reacting biaryltetrazole derivative [5'] obtained in the aforementioned Production method 2 with compound [24] (e.g., hydrochloride etc.) in the presence of a base or a base and an additive. This reaction can also be performed in a solvent.

While the base is not particularly limited, for example, triethylamine, ethyldiisopropylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP) and lutidine can be mentioned. The amount of the base to be used is generally 1 equivalent-10 equivalents, preferably, 1 equivalent-3 equivalents, relative to biaryltetrazole derivative [5'].

As the additive, tetraalkylammonium halide (e.g., tetrabutylammonium bromide), tetraalkylphosphonium halide and the like can be mentioned. The amount of the additive to be used is generally 0.01 equivalents-10 equivalents, preferably, 0.05 equivalents-1 equivalent, relative to biaryltetrazole derivative [5'].

While the solvent is not particularly limited as long as the reaction proceeds, toluene, xylene, methylene chloride, chloroform, acetonitrile, DMF, DMSO, THF, dimethoxyethane, t-BME, 1,4-dioxane and the like and a mixture of the above-mentioned solvent and water can be mentioned. The amount of the solvent to be used is generally 0.001 mL-100 mL, preferably, 0.1 mL-10 mL, per 1 mmol of biaryltetrazole derivative [5'].

The reaction temperature is generally −20° C.-150° C., preferably, 0° C.-100° C.

The reaction time is generally 0.1 hr-48 hr, preferably, 0.5 hr-10 hr.

(Step 2)

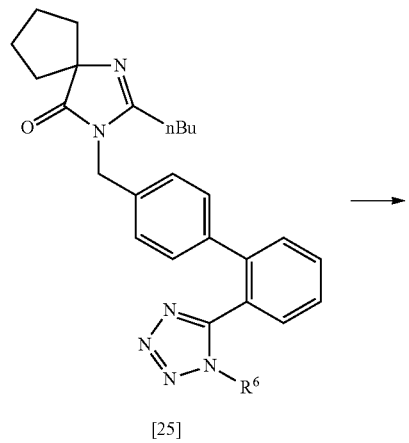

[25]

-continued

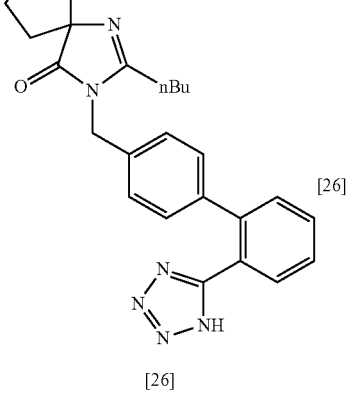

[26]

Compound [26] can be produced using compound [25] and in the same manner as in the methods described in the above-mentioned Production method 3, step 4.

[Production Method 7] and [Production Method 7'] (Candesartan Production Method)

(Step 1)

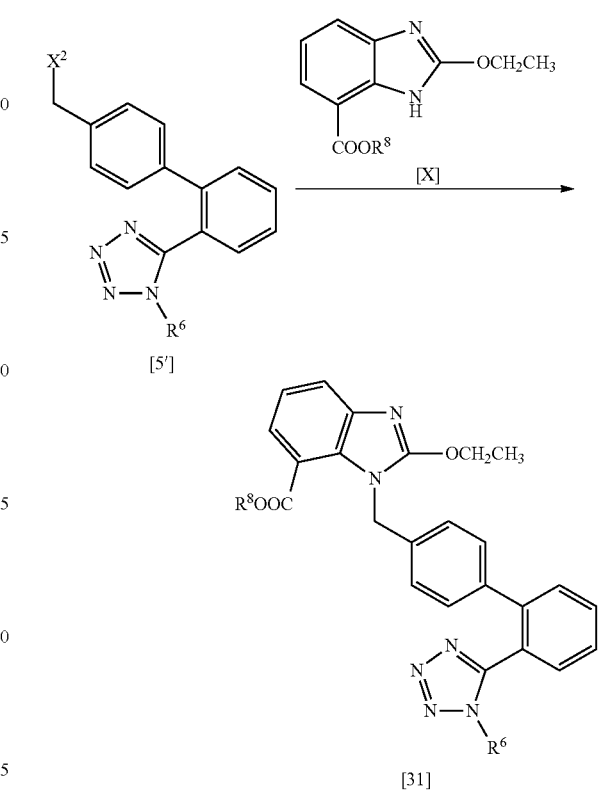

Compound [13] can be produced by reacting biaryltetrazole derivative [5'] obtained in the aforementioned Production method 2 with compound [X] in the presence of a base. This reaction can also be performed in a solvent.

The base is not particularly limited and, for example, potassium carbonate, potassium hydrogen carbonate, potassium phosphate, sodium hydroxide, sodium carbonate, sodium hydrogen carbonate, potassium hydroxide, triethylamine, ethyldiisopropylamine, DBU, 4-dimethylaminopyridine (DMAP), lutidine and the like can be mentioned. The amount of the base to be used is generally 1 equivalent-10 equivalents, preferably, 1 equivalent-3 equivalents, relative to biaryltetrazole derivative [5'].

The solvent is not particularly limited as long as the reaction proceeds, and DMA, methanol, ethanol, propanol, toluene, xylene, methylene chloride, chloroform, acetonitrile, DMF, DMSO, THF, dimethoxyethane, t-BME, 1,4-dioxane and the like, and a mixed solvent of two or more kinds selected therefrom can be mentioned. The amount of the solvent to be used is generally 0.001 mL-100 mL, preferably, 0.1 mL-10 mL, per 1 mmol of biaryltetrazole derivative [5'].

The reaction temperature is generally −20° C.-150° C., preferably, 10° C.-40° C.

The reaction time is generally 0.1 hr-48 hr, preferably, 0.5 hr-36 hr.

Compound [31] can also be produced, as another embodiment, by the method described in the following step 1'-1 to step 1'-4.

(Step 1'-1)

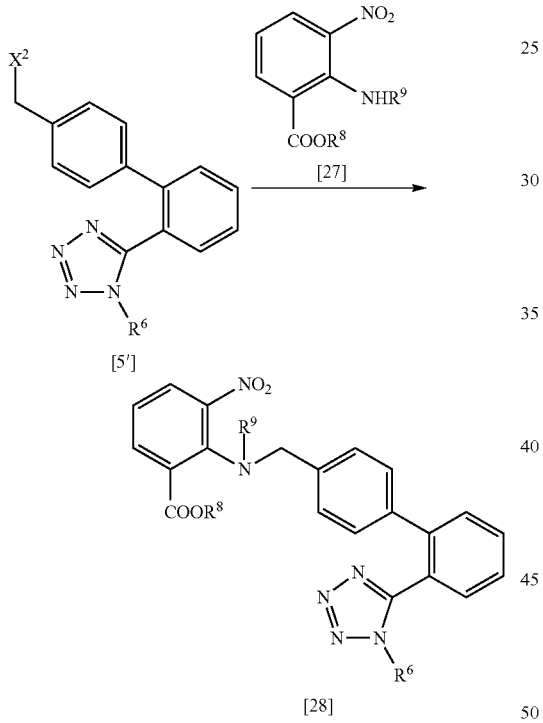

Compound [28] can be produced by reacting biaryltetrazole derivative [5'] obtained in the aforementioned Production method 2 with compound [27] in the presence or absence of a base. This reaction can also be performed in a solvent.

This reaction is preferably performed in the presence of a base. As the base, metal hydrides such as sodium hydride and the like, metal alkoxides such as sodium t-butoxide, potassium t-butoxide and the like, carbonates such as potassium carbonate, potassium hydrogen carbonate, sodium carbonate, sodium hydrogen carbonate and the like, and the like can be mentioned. Of these, carbonate, particularly potassium carbonate, is preferably used. The amount of the base to be used is generally 1 equivalent-5 equivalents relative to biaryltetrazole derivative [5'].

As the solvent, aprotic polar solvents such as dimethylformamide, dimethyl sulfoxide, dimethylacetamide and the like, ketones such as acetone, ethylmethylketone and the like, ethers such as tetrahydrofuran, dioxane and the like, esters such as ethyl acetate and the like, aromatic hydrocarbons such as benzene, toluene, xylene and the like, hydrocarbon halides such as methylene chloride, chloroform, carbon tetrachloride, dichloroethane and the like, acetonitrile and the like can be mentioned. Of these, acetonitrile is preferably used. The amount of the solvent to be used is generally 0.1 mL-10 mL, per 1 mmol of biaryltetrazole derivative [5'].

The reaction temperature is generally 70° C.-90° C. and the reaction time is 3 hr-10 hr.

(Step 1'-2)

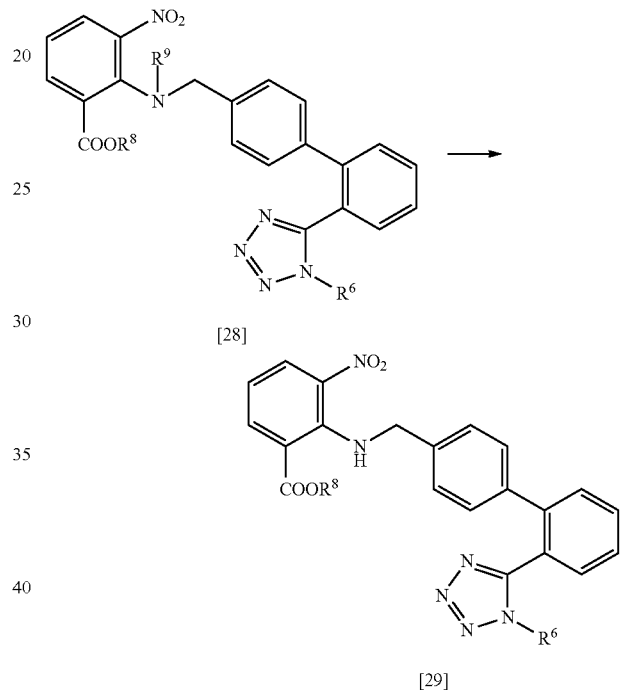

Compound [29] can be produced by removing $R^9$ of compound [28] in the presence of an acid.

The acid is not particularly limited, and acids known per se can be applied. For example, Brønsted acid (e.g., trifluoromethanesulfonic acid, methanesulfonic acid, phosphoric acid, sulfuric acid, hydrochloric acid etc.) and Lewis acid (e.g., aluminum chloride, tin chloride, boron trifluoride diethyl ether etc.) can be mentioned. The amount of the acid to be used is generally 0.1 equivalents-1000 equivalents, preferably, 1 equivalent-500 equivalents, relative to compound [28].

The solvent is not particularly limited as long as the reaction proceeds, and water, methanol, ethanol, isopropyl alcohol, tetrahydrofuran, dimethoxyethane, methyl t-butyl ether and the like can be mentioned. The amount of the solvent to be used is generally 0.01 mL-100 mL, preferably, 0.1 mL-10 mL, per 1 mmol of compound [28].

The reaction temperature is generally −50° C.-150° C., preferably, 10° C.-100° C.

The reaction time is generally 0.1 hr-48 hr, preferably, 0.5 hr-20 hr.

(Step 1'-3)

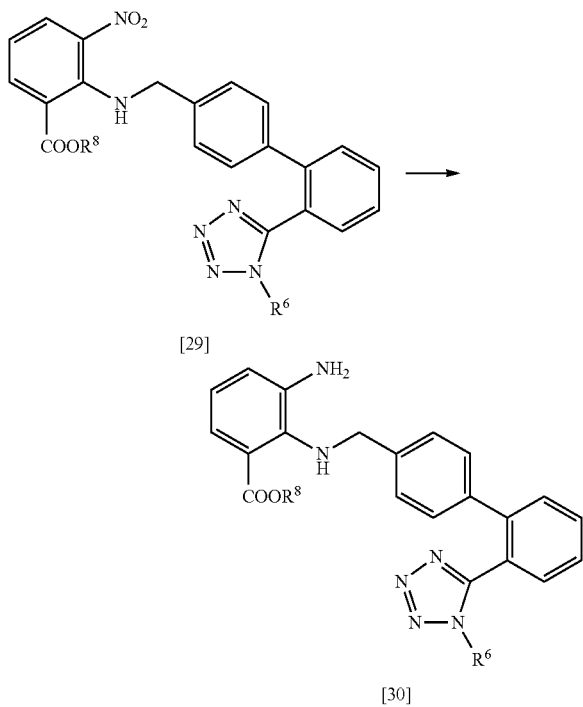

Compound [30] can be produced by reducing compound [29] in the presence of a reducing agent. This reaction can also be performed in a solvent.

The reducing agent is not particularly limited, and reducing agents known per se can be applied. For example, tin chloride, sodium borohydride, lithium borohydride, zinc borohydride, sodium triacetoxyborohydride and the like can be mentioned. The amount of the reducing agent to be used is generally 1 equivalent-10 equivalents, preferably, 1 equivalent-5 equivalents, relative to compound [29].

The solvent is not particularly limited as long as the reaction proceeds, and water, methanol, ethanol, isopropyl alcohol, dimethoxyethane, methyl t-butyl ether and the like can be mentioned. The amount of the solvent to be used is, compound [29] per 1 mmol of, generally 0.01 mL-100 mL, preferably, 0.1 mL-10 mL.

The reaction temperature is generally −50° C.-100° C., preferably, 20° C.-50° C.

The reaction time is generally 0.01 hr-48 hr, preferably, 0.1 hr-5 hr.

(Step 1'-4)

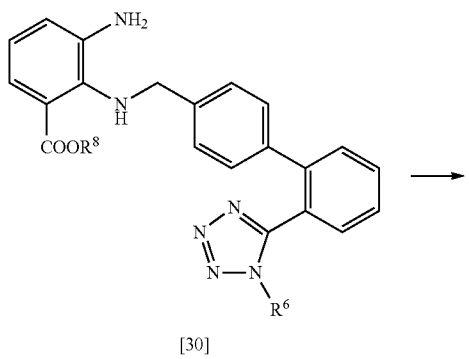

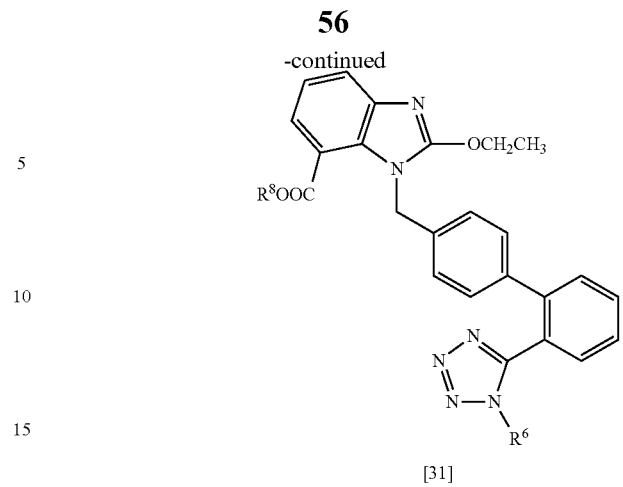

Compound [31] can be produced by reacting compound [30] with tetraethoxymethane in the presence or absence of a solvent.

The solvent is not particularly limited as long as the reaction proceeds, and ethanol, tetrahydrofuran, toluene, ethyl acetate, acetic acid, dimethoxyethane, methyl t-butyl ether and the like can be mentioned.

The reaction temperature is generally 0° C.-120° C., preferably, 50° C.-100° C.

The reaction time is generally 0.01 hr-48 hr, preferably, 0.1 hr-5 hr.

(Step 2)

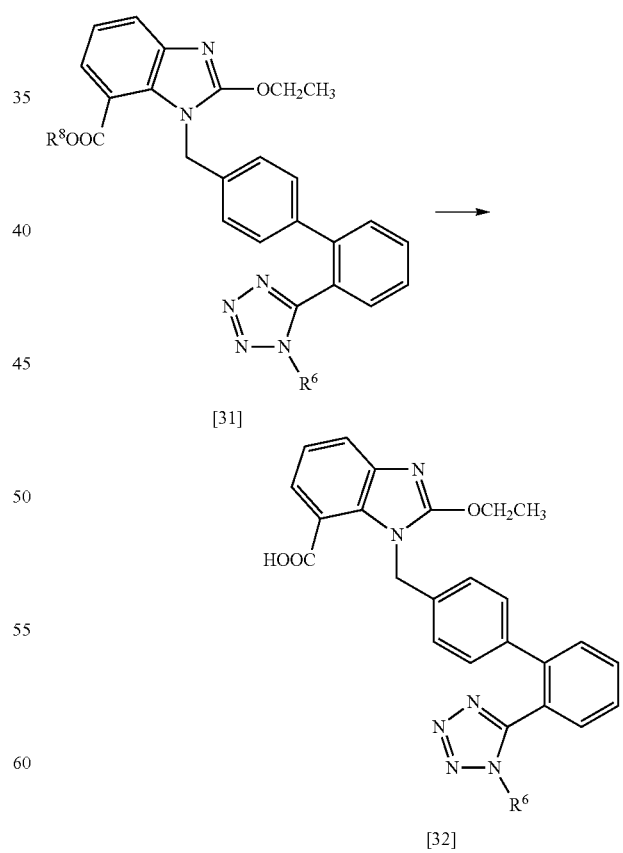

Compound [32] can be produced using compound [31] and in the same manner as in the method described in the above-mentioned Production method 5, step 2-A(3).

(Step 3)

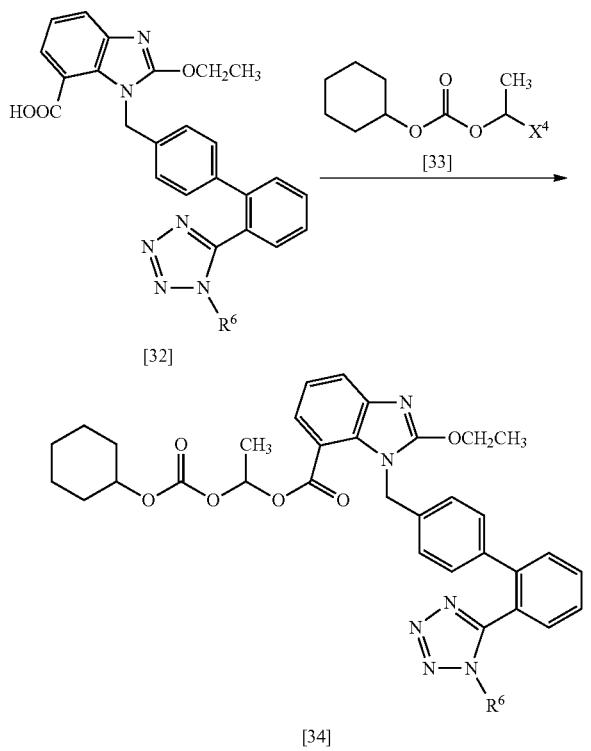

Compound [34] can be produced by reacting compound [32] with compound [33] in the presence of a base. This reaction can also be performed in a solvent.

The base is not particularly limited, and bases known per se can be applied. For example, sodium hydroxide, potassium hydroxide, sodium carbonate, potassium carbonate, sodium hydrogen carbonate, potassium hydrogen carbonate, triethylamine, tributylamine, methylamine, dimethylamine can be mentioned.

The solvent is not particularly limited as long as the reaction proceeds, and methanol, ethanol, isopropyl alcohol, dimethylformamide and the like can be mentioned. The amount of the solvent to be used is generally 0.01 mL-100 mL, preferably, 0.1 mL-10 mL, per 1 mmol of compound [32].

The reaction temperature is generally −50° C.-150° C., preferably, 10° C.-100° C.

The reaction time is generally 0.1 hr-48 hr, preferably, 0.5 hr-20 hr.

(Step 4)

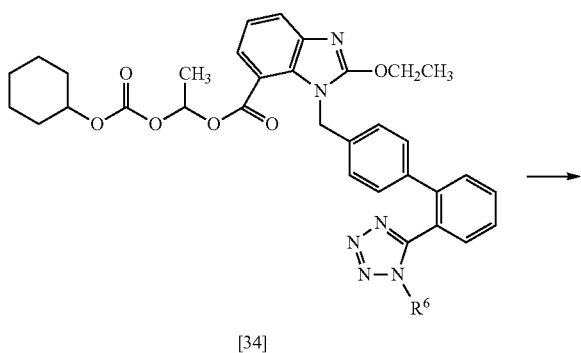

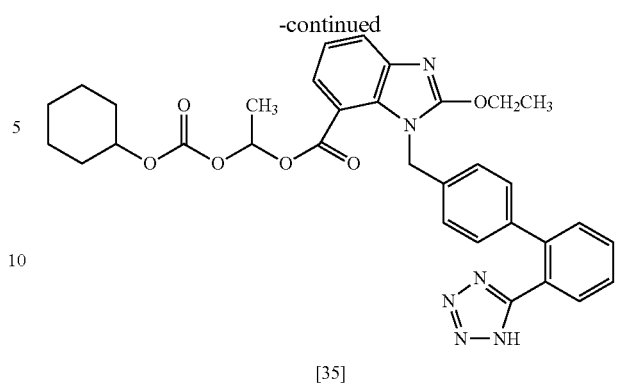

Compound [35] can be produced using compound [34] in the same manner as in the method described in the above-mentioned Production method 3, step 4.

The salt of compound [5] is not particularly limited and, for example, salts with hydrochloric acid, sulfuric acid and the like can be mentioned.

The salt of compound [11], compound [16], compound [23], compound [26] or compound [35] is not particularly limited as long as it is pharmacologically acceptable and, for example, salts with mineral acids such as hydrochloric acid, sulfuric acid, hydrobromic acid, phosphoric acid and the like;

salts with organic acids such as methanesulfonic acid, p-toluenesulfonic acid, acetic acid, oxalic acid, citric acid, malic acid, fumaric acid and the like;

salts with alkali metals such as sodium, potassium and the like;

salts with alkaline earth metals such as magnesium and the like;

salts with amines such as ammonia, ethanolamine, 2-amino-2-methyl-1-propanol and the like can be mentioned.

The salt of compound [23] is not particularly limited as long as it is pharmacologically acceptable and, for example, salts with alkali metals such as sodium, potassium and the like;

salts with alkaline earth metals such as magnesium and the like;

salts with amines such as ammonia, ethanolamine, 2-amino-2-methyl-1-propanol and the like can be mentioned.

Compound [5], compound [11], compound [16], compound [23], compound [26], compound [35], and salts thereof include solvates. Examples of the solvate include hydrate and alcohol solvates (e.g., methanol solvate, ethanol solvate).

EXAMPLES

The present invention is specifically explained in the following by referring to Reference Examples and Examples, which are not to be construed as limitative.

In the following Reference Example and Examples, "room temperature" means 15° C.-30° C.

In the following Reference Examples and Examples, "%" of the concentrations and contents means "wt %" unless particularly indicated.

Abbreviations in the Examples show the following compounds.

HBT: 1-benzyl-5-phenyl-1H-tetrazole
BAC: [2'-(1-benzyl-1H-tetrazol-5-yl)biphenyl-4-yl]methyl acetate
BBA: p-bromobenzyl acetate DBAC: {2'-[2-benzyl-2H-tetrazol-5-yl]-1,1': 3',1"-terphenyl-4,4"-diyl}dimethyl diacetate
BBB: p-bromobenzyl benzoate
BBZ: 1-benzyl-5-[4'-(benzoyloxymethyl)biphenyl-2-yl]-1H-tetrazole
BBR: 1-benzyl-5-[4'-(bromomethyl)biphenyl-2-yl]-1H-tetrazole
IME: ethyl 4-(1-hydroxy-1-methylethyl)-2-propyl-imidazole-5-carboxylate
TBAB: tetra-n-butylammonium bromide
BIA: ethyl 4-(1-hydroxy-1-methylethyl)-2-propyl-1-[[2'-[2-benzyl-2H-tetrazol-5-yl]biphenyl-4-yl]methyl]imidazole-5-carboxylate
BIH: ethyl 4-(1-hydroxy-1-methylethyl)-2-propyl-1-[[2'-[2H-tetrazol-5-yl]biphenyl-4-yl]methyl]imidazole-5-carboxylate
BIT: ethyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate
BIC: potassium 4-(1-hydroxy-1-methylethyl)-2-propyl-1-[[2'-[2-(triphenylmethyl)-2H-tetrazol-5-yl]biphenyl-4-yl]methyl]imidazole-5-carboxylate
TOLM: (5-methyl-2-oxo-1,3-dioxol-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate
OLM MDX: (5-methyl-2-oxo-1,3-dioxol-4-yl)methyl 4-(1-hydroxy-1-methylethyl)-2-propyl-1-[[2'-(2H-tetrazol-5-yl)biphenyl-4-yl]methyl]imidazole-5-carboxylate
BCL: 1-benzyl-5-[4'-(chloromethyl)biphenyl-2-yl]-1H-tetrazole
VM: N-[[2'-benzyl-1H-tetrazol-5-yl][1,1'-biphenyl]-4-yl]methyl]-L-valine methyl ester
BAL: 1-benzyl-5-[4'-(hydroxymethyl)biphenyl-2-yl]-1H-tetrazole
BIM: methyl 2-ethoxy-1H-benzimidazole-7-carboxylate
CBME: ethyl 2-ethoxy-1-[2'-[1-benzyl-1H-tetrazol-5-yl]biphenyl-4-yl]-1H-benzimidazole-7-carboxylate
CBCA: 2-ethoxy-1-[2'-[1-benzyl-1H-tetrazol-5-yl]biphenyl-4-yl]-1H-benzimidazole-7-carboxylic acid

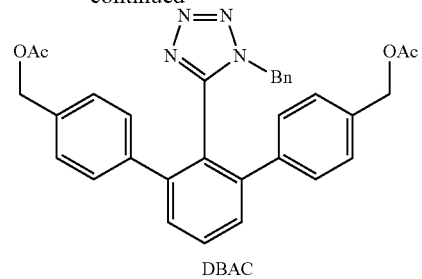

DBAC

A mixture of triphenylphosphine (0.05 g, 0.19 mmol), 1-benzyl-5-phenyl-1H-tetrazole (HBT, 5 g, 21.2 mmol), potassium carbonate (1.76 g, 12.7 mmol), potassium acetate (0.208 g, 2.12 mol), p-bromobenzyl acetate (BBA, 5.34 g, 23.3 mmol) and N-methyl-2-pyrrolidone (25 mL) was heated to 138° C. under a nitrogen atmosphere, dichloro(p-cymene)ruthenium (II) dimer (0.065 g, 0.106 mmol as monomer) was added, and the mixture was m stirred at the same temperature for 6 hr. The reaction mixture was cooled, and mixed with water (10 mL) and t-butyl methyl ether (20 mL). The aqueous layer was extracted with t-butyl methyl ether (20 mL×2), the extracts were combined with the organic layer, and the mixture was washed with water (20 mL×2) and brine (10 mL), dried over sodium sulfate, and concentrated under reduced pressure to give a crude product of BAC (9.4 g, 115.6% of the theoretical yield) as a dark brown oily substance. The conversion yield of this reaction was 96.2% [BAC:DBAC=81:19]. The product was purified by silica gel column (hexane:ethyl acetate=4:1), from which the following properties were obtained.

mp 74.4° C.; IR (neat): 1741 (C=O), 1603 cm$^{-1}$; $^1$H NMR (CDCl$_3$): δ=7.63 (td, J=7.6, 1.4 Hz, 1H), 7.57 (dd, J=7.6, 1.4 Hz, 1H), 7.44 (td, J=7.6, 1.4 Hz, 1H), 7.34 (dd, J=7.6, 1.4 Hz, 1H), 7.27 (d, J=8.6 Hz, 2H), 7.22 (t, J=8.6 Hz, 1H), 7.16 (t, J=8.6 Hz, 2H), 7.13 (d, J=7.2 Hz, 2H), 6.76 (d, J=7.2 Hz, 2H), 5.09 (s, 2H), 4.82 (s, 2H), 2.11 (s, 3H); $^{13}$C NMR (CDCl$_3$): δ=171, 155, 141, 139, 136, 133, 132, 131, 130, 129, 129, 128, 128, 122, 66, 51, 21; MS 385 [M+H]$^+$.

Example 1

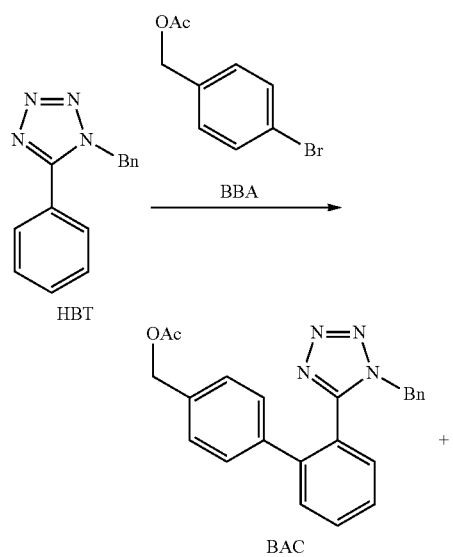

Example 2

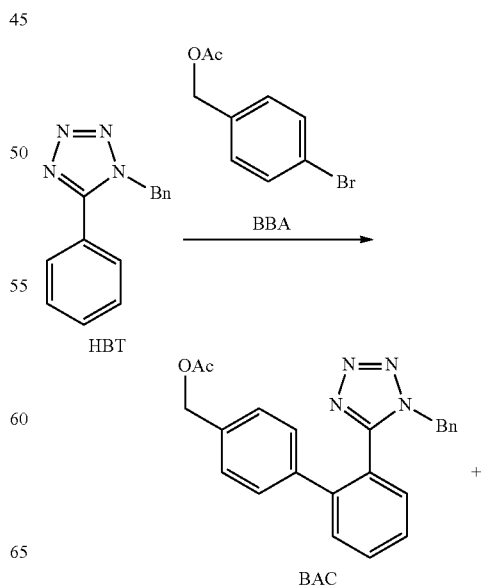

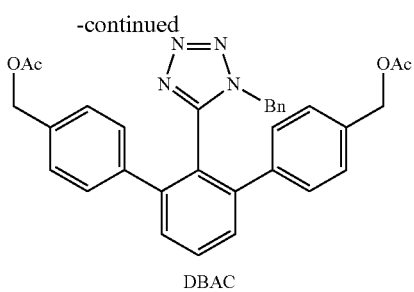

Using triphenylphosphine (0.031 g, 0.118 mmol), 1-benzyl-5-phenyl-1H-tetrazole (HBT, 5 g, 21.2 mmol), potassium carbonate (2.92 g, 12.7 mmol), potassium acetate (0.208 g, 2.12 mmol), p-bromobenzyl acetate (BBA, 5.34 g, 23.3 mmol), N-methyl-2-pyrrolidone (25 mL) and dichloro(p-cymene)ruthenium (II) dimer (0.052 g, 0.084 mmol as monomer), an operation similar to that in Example 1 was performed to give a crude product of BAC (9.2 g, 113.2% of the theoretical yield) as a dark brown oily substance. The conversion yield of this reaction was 96.7% [BAC:DBAC=79:21].

Example 3

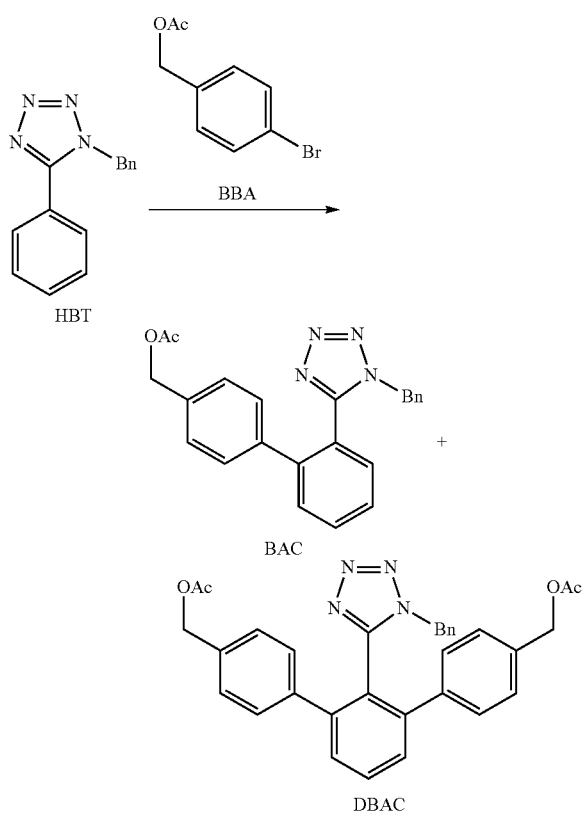

To dichloro(p-cymene)ruthenium (II) dimer (0.026 g, 0.042 mmol as monomer) and potassium pivalate (0.024 g, 0.17 mmol) was added N-methyl-2-pyrrolidone (5 mL), and the mixture was stirred at 25° C. for 1 hr. 1-Benzyl-5-phenyl-1H-tetrazole (HBT, 2 g, 8.46 mmol), p-bromobenzyl acetate (BBA, 2.13 g, 9.31 mmol), potassium carbonate (1.17 g, 8.46 mmol) and N-methyl-2-pyrrolidone (5 mL) were added thereto, and the mixture was stirred at 138° C. for 5.5 hr. After completion of the reaction, a treatment similar to that in Example 1 was performed to give to a crude product of BAC (3.53 g, 109% of the theoretical yield) as a dark brown oily substance. The conversion yield of this reaction was 95.4% [BAC:DBAC=79:21].

Example 4

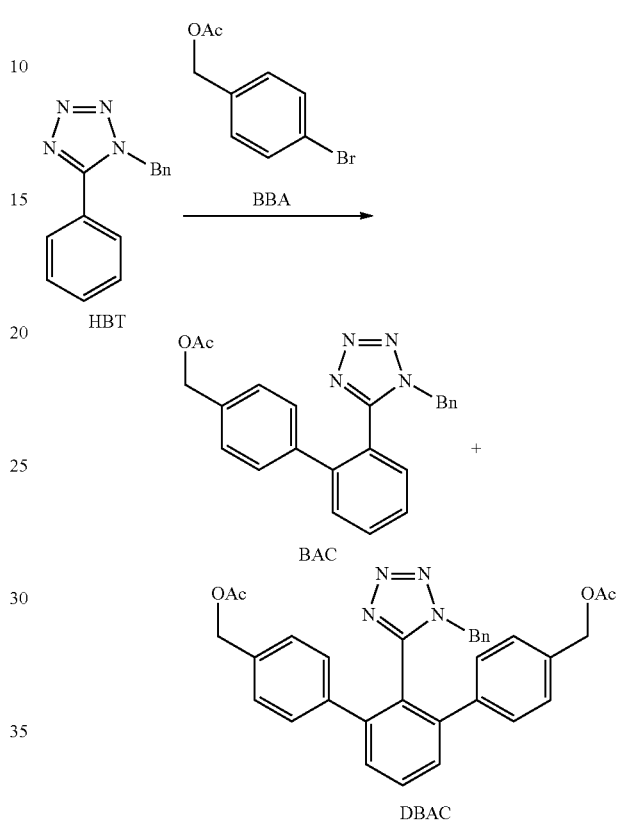

A mixture of 1-benzyl-5-phenyl-1H-tetrazole (HBT, 5 g, 21.2 mmol), potassium carbonate (2.92 g, 21.2 mmol), p-bromobenzyl acetate (BBA, 5.34 g, 23.3 mmol) and N-methyl-2-pyrrolidone (25 mL) was heated to 138° C. under a nitrogen atmosphere, dipivaloyloxy(p-cymene)ruthenium (II) (0.093 g, 0.21 mmol) was added, and the mixture was stirred at the same temperature for 6 hr. A treatment similar to that in Example 1 was performed to give a crude product of BAC (9.34 g, 114.9% of the theoretical yield) as a dark brown oily substance. The conversion yield of this reaction was 96.2% [BAC:DBAC=77:23].

Example 5

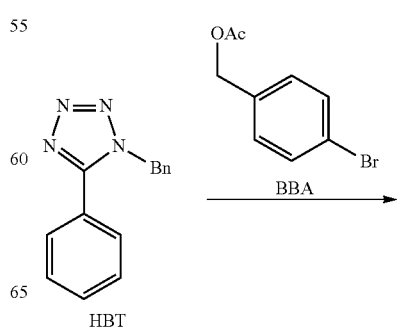

-continued

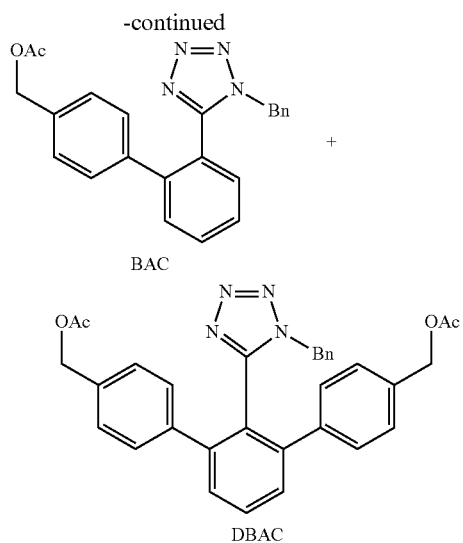

BAC

DBAC

A mixture of 1-benzyl-5-phenyl-1H-tetrazole (HBT, 10 g, 42.3 mmol), potassium carbonate (5.85 g, 42.3 mmol), p-bromobenzyl acetate (BBA, 10.7 g, 46.6 mmol), dipotassium glutarate (0.882 g, 4.23 mmol) and N-methyl-2-pyrrolidone (50 mL) was heated to 138° C. under a nitrogen atmosphere, dichloro(p-cymene)ruthenium (II) dimer (0.13 g, 0.21 mmol) was added, and the mixture was stirred at the same temperature for 6 hr. The reaction mixture was cooled and mixed with water (50 mL) and t-butyl methyl ether (50 mL). The aqueous layer was extracted with t-butyl methyl ether (50 mL×2), the extracts were combined with the organic layer, and the mixture was washed with water (50 mL×2) and brine (50 mL), dried over sodium sulfate, and concentrated under reduced pressure to give a crude product of BAC (18.4 g, 113.3% of the theoretical yield) as a dark brown oily substance. The conversion yield of this reaction was 93.4% [BAC:DBAC=85:15].

Example 6

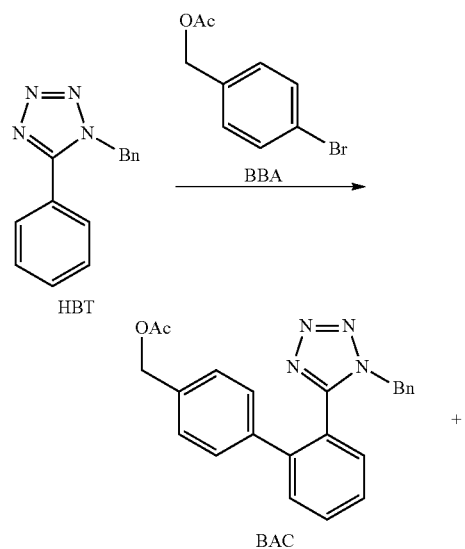

-continued

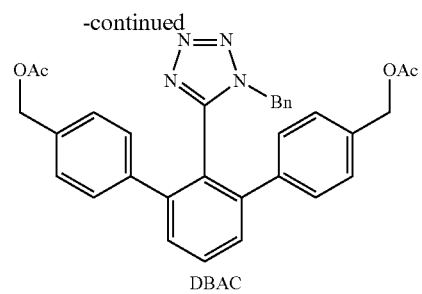

DBAC

A mixture of 1-benzyl-5-phenyl-4H-tetrazole (HET, 2 g, 8.4 mmol), potassium carbonate (1.17 g, 8.4 mmol), p-bromobenzyl acetate (BBA, 2.13 g, 9.3 mmol), triphenylphosphine (0.072 g, 0.275 mmol), potassium 4-dodecylbenzenesulfonate (0.044 g, 0.12 mmol) and N-methyl-2-pyrrolidone (10 mL) was heated to 138° C. under a nitrogen atmosphere, ruthenium chloride(III) hydrate (0.023 g, 0.095 mmol) was added, and the mixture was stirred at the same temperature for 6 hr. The same operation as in Example 1 was performed to give a crude product of BAC (3.4 g, 104.5% of the theoretical yield) as a dark brown oily substance. The conversion yield of this reaction was 83.9% [BAC: DBAC=96:4].

Example 7

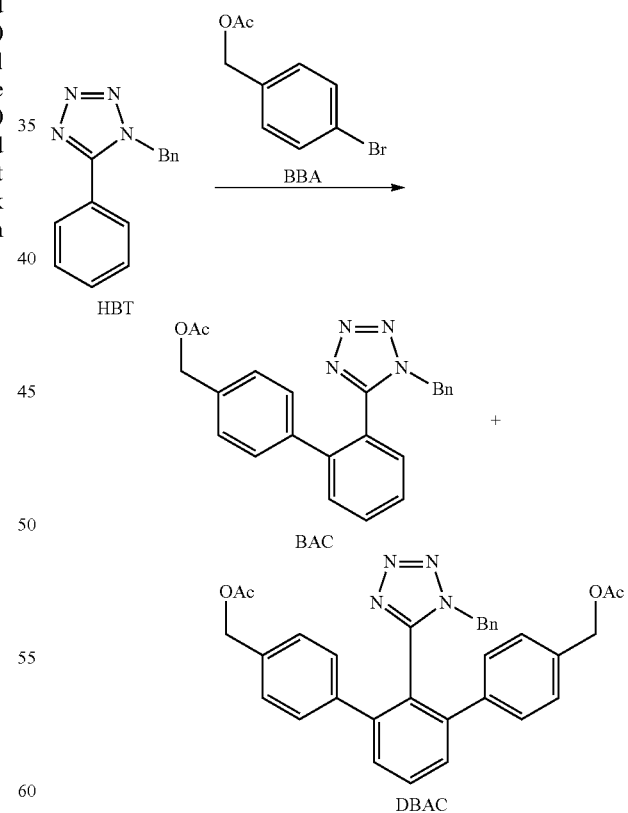

A mixture of 1-benzyl-5-phenyl-1H-tetrazole (HBT, 2 g, 8.4 mmol), potassium carbonate (1.17 g, 8.4 mmol), triphenylphosphine (0.052 g, 0.2 mmol), p-bromobenzyl acetate (BBA, 2.13 g, 9.3 mmol), bis(2-ethylhexyl)potassium phosphate (0.044 g, 0.12 mmol) and N-methyl-2-pyrrolidone (10 mL) was heated to 138° C. under a nitrogen atmosphere, ruthenium chloride (III) hydrate (0.023 g, 0.095 mmol) was added, and the mixture was stirred at the same temperature for 6 hr. The same operation as in Example 1 was performed to give a crude product of BAC (3.57 g, 109.7% of the theoretical yield) as a dark brown oily substance. The conversion yield of this reaction was 91.2% [BAC:DBAC=93:7].

Example 8

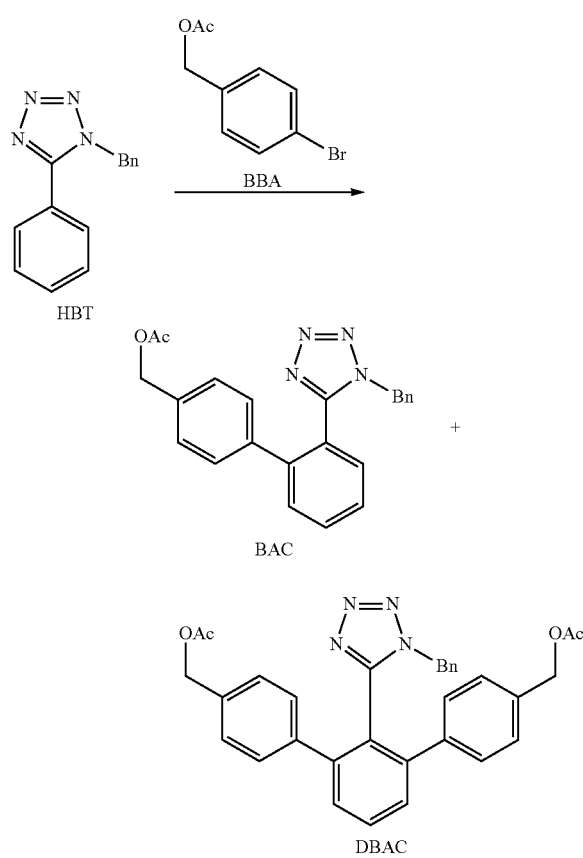

A mixture of 1-benzyl-5-phenyl-1H-tetrazole (HBT, 5 g, 21.2 mmol), potassium carbonate (2.93 g, 21.2 mmol), triphenylphosphine (0.178 g, 0.68 mmol), p-bromobenzyl acetate (BBA, 5.33 g, 23.3 mmol), potassium bis(2-ethylhexyl)phosphate (0.099 g, 0.28 mmol) and N-methyl-2-pyrrolidone (20 mL) was heated to 138° C. under a nitrogen atmosphere, ruthenium chloride(III) hydrate (0.057 g, 0.24 mmol) was added, and the mixture was stirred at the same temperature for 5 min. N-Methyl-2-pyrrolidone (5 mL) solution of bis(2-ethylhexyl)phosphoric acid (1.46 g, 4.52 mmol) was added, and the mixture was stirred for 6 hr. The same operation as in Example 1 was performed to give a crude product of BAC (9.8 g, 120.5% of the theoretical yield) as a dark brown oily substance. The conversion yield of this reaction was 85.7% [BAC:DBAC=94:6].

Comparative Example 1

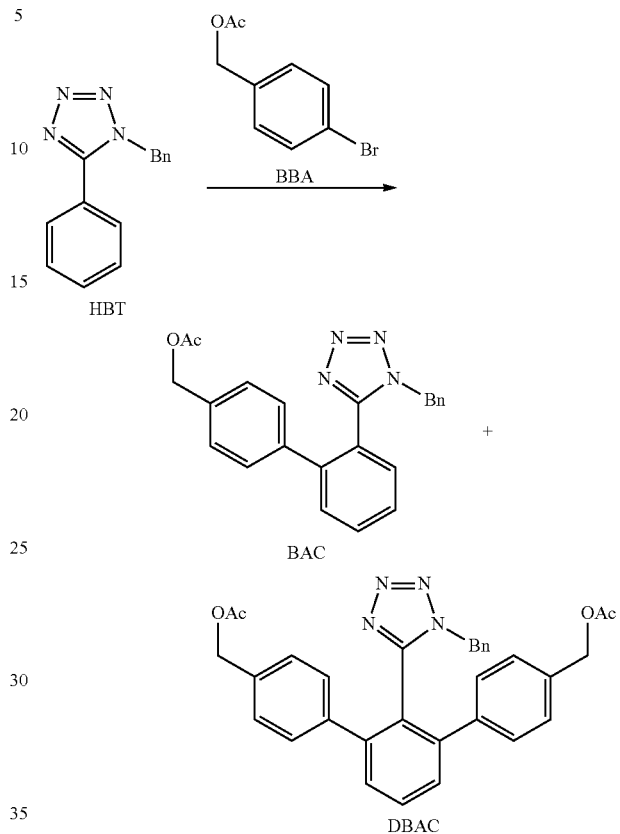

A mixture of 1-benzyl-5-phenyl-1H-tetrazole (HBT, 2 g, 8.4 mmol), potassium carbonate (1.17 g, 8.4 mmol), triphenylphosphine (0.052 g, 0.2 mmol), p-bromobenzyl acetate (BBA, 2.13 g, 9.3 mmol) and N-methyl-2-pyrrolidone (10 mL) was heated to 138° C. under a nitrogen atmosphere, ruthenium chloride hydrate (0.023 g, 0.095 mmol) was added, and the mixture was stirred at the same temperature for 6 hr. The same operation as in Example 1 was performed to give a crude product of BAC (3.5 g, 107.7% of the theoretical yield) as a dark brown oily substance. The conversion yield of this reaction was 66.2%.

Comparative Example 2

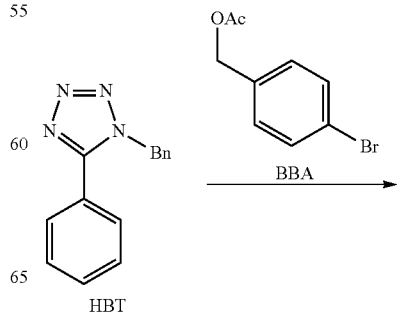

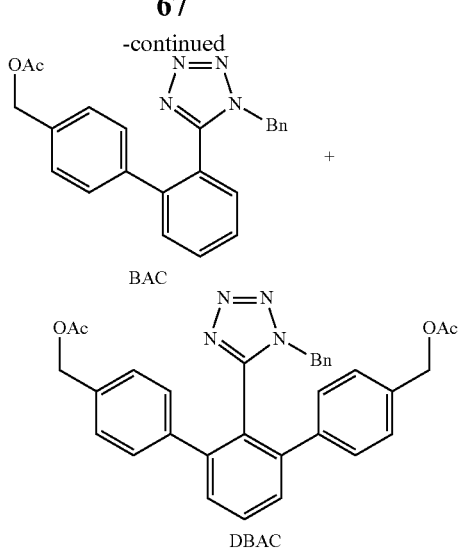

A mixture of 1-benzyl-5-phenyl-1H-tetrazole (HBT, 2 g, 8.4 mmol), potassium carbonate (1.17 g, 8.4 mmol), p-bromobenzyl acetate (BBA, 2.13 g, 9.3 mmol) and N-methyl-2-pyrrolidone (10 mL) was heated to 138° C. under a nitrogen atmosphere, dichloro(p-cymene)ruthenium (II) dimer (0.021 g, 0.034 mmol) was added, and the mixture was stirred at the same temperature for 6 hr. The same operation as in Example 1 was performed to give a crude product of BAC (3.7 g, 113.8% of the theoretical yield) as a dark brown oily substance. The conversion yield of this reaction was 20.3%.

Example 9

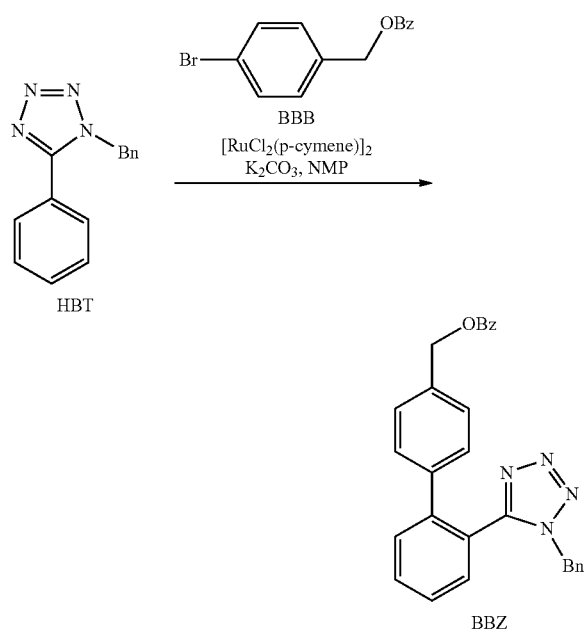

A mixture of 1-benzyl-5-phenyl-1H-tetrazole (HBT, 100 g, 1 eq), p-bromobenzyl benzoate (BBB, 135.5 g, 1.1 eq), potassium carbonate (58.5 g, 1 eq), triphenylphosphine (2.23 g, 2 eq relative to Ru) and N-methyl-2-pyrrolidone (380 mL, 3.8 vol) was stirred for 5 min. A solution (122 mL, 2 eq relative to Ru) of 2.5% potassium bis(2-ethylhexyl)phosphate in N-methyl-2-pyrrolidone was added thereto, and the mixture was stirred for 5 min. Argon gas was blown into the mixture for 10 min to remove oxygen from the mixture. The reaction mixture was heated to 138° C.-140° C., and dichloro(p-cymene)ruthenium (II) dimer (1.3 g, 0.005 eq) was added at 138° C.-140° C. Furthermore, argon gas was blown into the mixture for 10 min to remove oxygen from the reaction mixture. Then, the reaction mixture was stirred at 138° C.-140° C. for 8 hr. The reaction was monitored by TLC: thin layer chromatography (TLC eluent: 30% ethyl acetate/hexane, detection method: UV). HBT was contained in a trace amount.

The reaction mixture was cooled to 25° C.-30° C., t-butyl methyl ether (500 mL, 5 vol) was added thereto, and the mixture was stirred for 5 min and filtered through a filter lined with celite. The celite layer was washed with t-butyl methyl ether (500 mL, 5 vol). The filtrate and washing were combined, desalting water (500 mL, 5 vol) was added thereto, and the mixture was stirred for 10 min and left standing for 5 min. After partitioning, the aqueous layer was extracted with t-butyl methyl ether (2×500 mL, 2×5 vol). The extracts were combined with the organic layer, deionized water (500 mL, 5 vol) was added, and the mixture was stirred for 10 min. The mixture was left standing for 5 min and partitioned. To the t-butyl methyl ether layer was added saturated brine (500 mL, 5 vol), and the mixture was stirred for 10 min. After standing and partitioning, the t-butyl methyl ether layer was dried over sodium sulfate (50 g, 0.5 w/w). The mixture was filtered and the filtrate was concentrated under reduced pressure at 40° C.-45° C. to give a crude product of BBZ (220 g) as a green syrup.

To the obtained crude product was added t-butyl methyl ether (400 mL, 4 vol), and the mixture was stirred at 25° C.-30° C. for 24 hr to result in precipitation of a solid. The solid was collected by filtration and the obtained solid was dried with suction to give BBZ (140 g, 68.5%) as a green solid.

Example 10

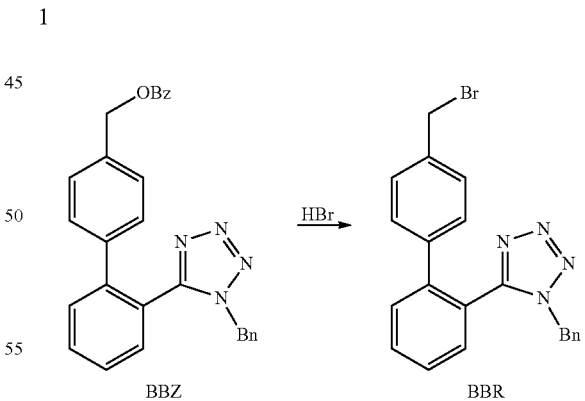

To BBZ (135 g, 1 eq) cooled to 0° C.-5° C. was added 33% hydrogen bromide/acetic acid solution (405 mL, 3 vol) at 0° C.-5° C. over 15 min. The reaction mixture was stirred at 25° C.-30° C. for 18 hr. The reaction was checked by TLC: thin layer chromatography (TLC eluent: 30% ethyl acetate/hexane, detection method: UV), and complete disappearance of BBZ was confirmed.

The reaction mixture was filtered, precipitated BBR was collected by filtration, and the obtained solid was dried with suction for 1 hr and further blast dried for 8 hr. To the obtained solid was added 50% ethyl acetate/hexane (270 mL, 2 vol), and the obtained suspension was stirred at 25° C.-30° C. for 1 hr. The suspension was filtered to give BBR (113 g, 92%) as a pale-yellow solid.

2

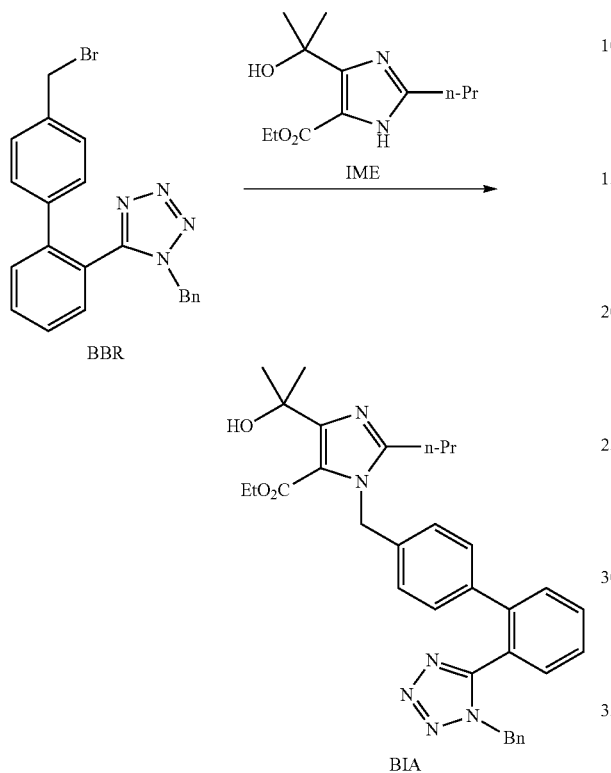

IME (50 g, 1 eq) was charged in a flask, acetone (125 mL, 2.5 vol) was added, and the mixture was dissolved by stirring for 5 min. Potassium carbonate (71.8 g, 3 eq) and TBAB (0.67 g, 0.01 eq) were added thereto. The reaction mixture was cooled to 0° C.-5° C., BBR (96 g, 1.05 eq) dissolved in acetone (125 mL, 2.5 vol) was added thereto over 15 min, and the reaction mixture was stirred at 25° C.-30° C. for 12 hr. The reaction mixture was further stirred at 40° C.-45° C. for 8 hr. Using TLC, complete consumption of BBR was confirmed. The reaction mixture was cooled to 25° C.-30° C., and then concentrated under reduced pressure at 40° C.-45° C. To the concentrated residue were added ethyl acetate (200 mL, 4 vol) and deionized water (400 mL, 8 vol), the mixture was stirred for 15 min and partitioned, and the aqueous layer was extracted with ethyl acetate (200 mL, 4 vol). The organic layers were combined, desalting water (2×200 mL, 2×4 vol) was added, and the mixture was stirred for 10 min and partitioned. To the organic layer was added 0.5% hydrochloric acid (250 mL, 5 vol), and the mixture was stirred for 10 min and further partitioned. Deionized water (2×200 mL, 2×4 vol) was added to the organic layer, and the mixture was stirred for 5 min, left standing and partitioned. To the organic layer was added saturated brine (125 mL, 5 vol), and the mixture was stirred for 5 min, left standing for 5 min, and partitioned. The organic layer was dried over sodium sulfate and filtered, and the filtrate was concentrated under reduced pressure at 40° C.-45° C. to give a crude product of BIA (110 g, 93.5%).

To the obtained crude product of BIA was added ethyl acetate (110 mL, 1 vol relative to the crude product), and the mixture was dissolved by heating to 60° C.-65° C. n-Heptane (550 mL, 5 vol relative to the crude product) was added thereto at 60° C.-65° C. over 5 min, heating was stopped and the mixture was allowed to gradually cool to 25° C.-30° C., whereby a solid was precipitated. The solid was collected by filtration to give BIA. To the obtained BIA (175 g) was added ethyl acetate (175 mL, 1 vol), and the mixture was dissolved by stirring at 60° C.-65° C. for 15 min. n-Heptane (875 mL, 5 vol) was added thereto over 15 min, heating was stopped and the mixture was allowed to gradually cool to 25° C.-30° C., whereby a solid was precipitated. The solid was collected by filtration, dried with suction for 30 min, and further dried at 45° C.-50° C. for 30 min to give BIA (165 g).

3

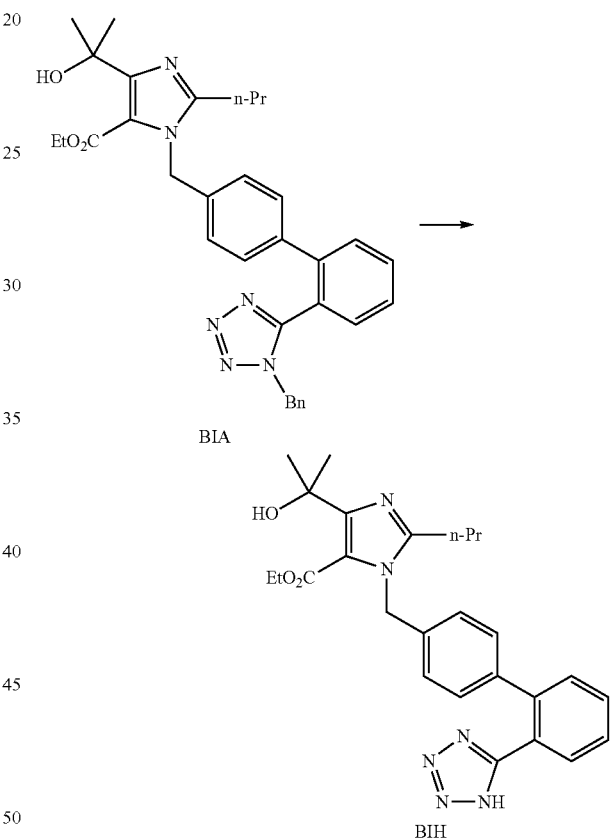

To BIA (160 g, 1 eq) were added isopropyl alcohol (800 mL, 5 vol) and water (480 mL, 3 vol), and ammonium formate (85.76 g, 4.8 eq) and 5% palladium/barium sulfate (17.88 g, 3 mol %) were further added. The reaction mixture was stirred at 55° C.-60° C. for 12 hr. Using TLC (thin layer chromatography) (TLC eluent: 5% methanol/methylene chloride, detection method: UV), complete disappearance of BIA was confirmed.

The reaction mixture cooled to 25° C.-30° C. was filtered through a filter lined with celite, and the celite layer was washed with isopropyl alcohol (2×160 mL, 2×1 vol). The filtrate and washing were combined and concentrated under reduced pressure at 40° C.-45° C. To the concentrated residue were added methylene chloride (720 mL, 4.5 vol) and desalting water (448 mL, 2.8 vol), and the mixture was stirred for 5 min. The mixture was adjusted to pH 3-4 by adding 5% hydrochloric acid, stirred for 5 min, left standing for 5 min, and partitioned. The aqueous layer was extracted with methylene chloride (2×200 mL, 2×1.25 vol), the extracts were combined with the organic layer, and the mixture was washed with deionized water (2×320 mL, 2×2 vol) and partitioned. The organic layer was washed with saturated brine (2×320 mL, 2×2 vol). The organic layer was dried over sodium sulfate and filtered, and the filtrate was concentrated under reduced pressure at 40° C.-45° C. to give BIH (100 g, 74%).

4

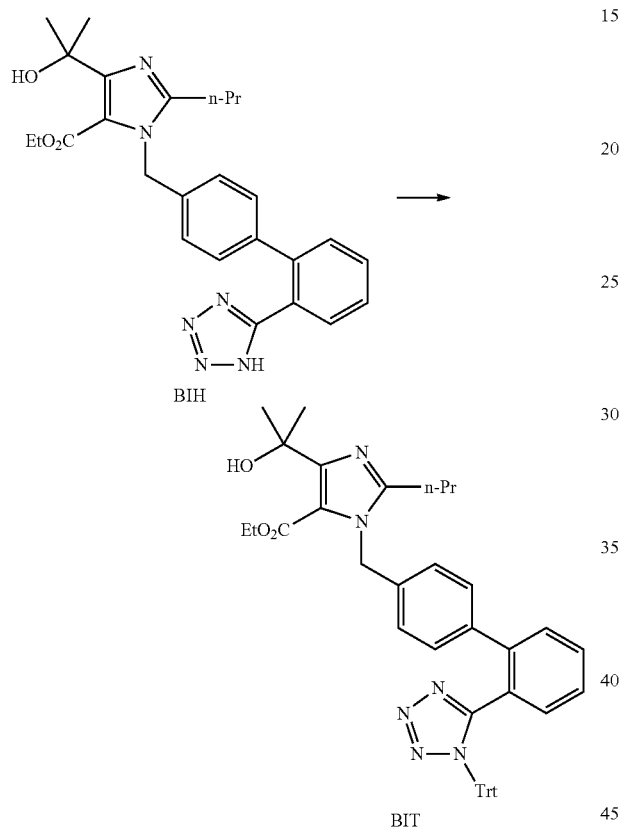

BIH

To BIH (100 g, 1 eq) was added methylene chloride (500 mL, 5 vol), and the mixture was dissolved. Triethylamine (32.3 mL, 1.1 eq) was added thereto, and the reaction mixture was cooled to 0° C.-5° C. A solution of trityl chloride (63.22 g, 1.08 eq) in methylene chloride (300 mL, 3 vol) was slowly added thereto at 0° C.-5° C. over 30 min, and the reaction mixture was stirred at 25° C.-30° C. for 12 hr. Trityl chloride (2.92 g, 0.05 eq) was added, and the reaction mixture was further stirred for 3 hr. Using TLC (thin layer chromatography) (TLC eluent: 10% methanol/methylene chloride, detection method: UV), complete disappearance of BIH was confirmed.

The reaction mixture was cooled to 0° C.-5° C., desalting water (270 mL, 2.7 vol) was added, and the mixture was stirred at 25° C.-30° C. for 15 min. The mixture was left standing and partitioned. The aqueous layer was extracted with methylene chloride (200 mL, 2 vol), the extracts were combined with the organic layer, and the mixture was washed with deionized water (500 mL, 5 vol). The organic layer was dried over sodium sulfate and filtered, and the filtrate was concentrated under reduced pressure at 40° C.-45° C. to give BIT (135 g, 89%).

5

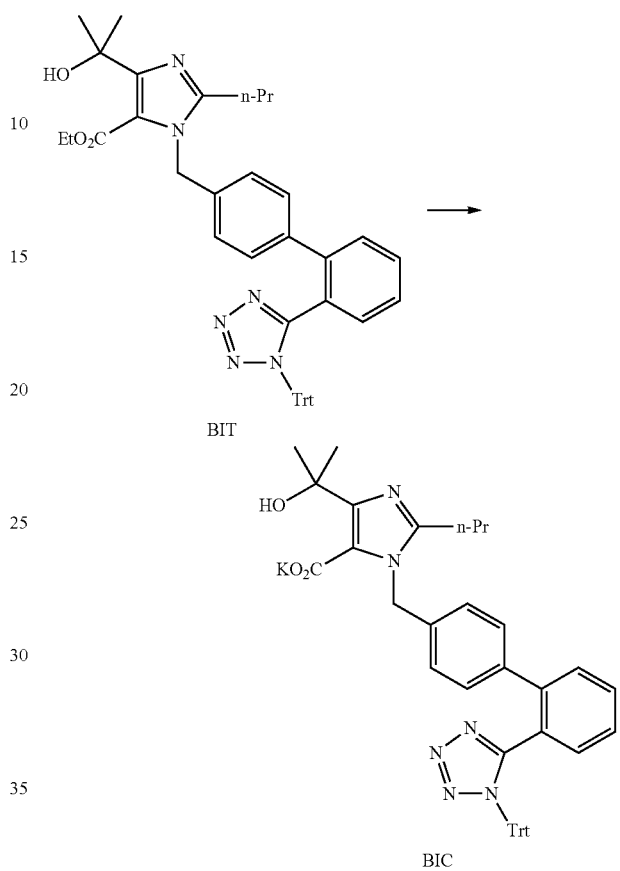

To BIT (130 g, 1 eq) was added acetone (650 mL, 5 vol) at 25° C.-30° C., and the mixture was dissolved. The reaction mixture was cooled to 0° C.-5° C., and a solution of potassium hydroxide (30.5 g, 3 eq) in desalting water (130 mL, 1 vol) was slowly added over 15 min. The reaction temperature was warmed to 40° C.-45° C., and the mixture was stirred at 40° C.-45° C. for 5 hr. Using TLC (thin layer chromatography) (TLC eluent: 10% methanol/methylene chloride, detection method: UV), complete disappearance of BIT was confirmed.

The precipitated solid was filtered, and the filtrate was concentrated under reduced pressure at 40° C.-45° C. To the obtained concentrated residue were added 25% brine (520 mL, 4 vol) and ethyl acetate (780 mL, 6 vol). After stirring for 10 min, the mixture was left standing for 5 min and partitioned. The aqueous layer was extracted with ethyl acetate (2×260 mL, 2×2 vol), and the extracts were combined with the organic layer. To the organic layer was added saturated aqueous sodium hydrogen carbonate (3×390 mL, 3×3 vol), and the mixture was stirred for 5 min, left standing and partitioned. To the organic layer was added saturated brine (650 mL, 5 vol), and the mixture was stirred for 5 min, left standing and partitioned. The organic layer was dried over sodium sulfate and filtered, and the filtrate was concentrated under reduced pressure at 40° C.-45° C. to give crude product of BIC (115 g, 87%) as a white solid. The crude product was directly used for the next step.

6

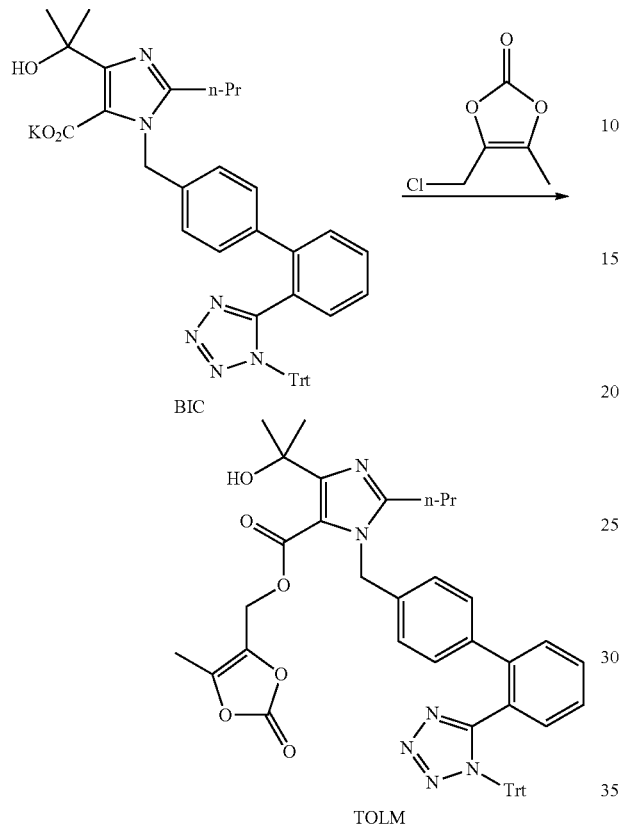

BIC

TOLM

To BIC (110 g, 1 eq) was added acetone (385 mL, 3.5 vol) at 25° C.-30° C., and the mixture was dissolved by stirring for 5 min. Sodium carbonate (20.85 g, 1.3 eq) and potassium iodide (0.25 g, 0.01) were added, and the mixture was stirred for 10 min. A solution of 4-chloromethyl-5-methyl-2-oxo-1,3-dioxolene (31.456 g, 1.4 eq) in acetone (165 mL, 1.5 vol) was added thereto. The reaction mixture was heated to 45° C.-50° C., and stirred at the same temperature for 12 hr. Using TLC (thin layer chromatography) (TLC eluent: 10% methanol/methylene chloride, detection method: UV), complete disappearance of BIC was confirmed. The reaction mixture was cooled to 25° C.-30° C. Then, the solvent contained in the reaction mixture was evaporated under reduced pressure at 40° C.-45° C. To the obtained residue were added 10% brine (550 mL, 5 vol) and toluene (550 mL, 5 vol). Furthermore, the mixture was adjusted to pH 7-8 by adding 5% hydrochloric acid (33 mL), stirred for 10 min, left standing for 5 min and partitioned. The aqueous layer was extracted with toluene (2×330 mL, 2×3 vol). The extracts were combined with the organic layer, 10% brine (550 mL, 5 vol) was added, and the mixture was stirred for 5 min, left standing for 45 min, partitioned, and concentrated under reduced pressure at 40° C.-45° C. to give TOLM (110 g, 90%).

To the obtained TOLM was added acetone (110 mL, 1 vol), and the mixture was stirred at 25° C.-30° C. for 30 min. n-Heptane (440 mL, 4 vol) was added, and the mixture was cooled to 5° C.-10° C. and stirred at 5° C.-10° C. for 30 min, whereby precipitation of a solid was confirmed. The solid (80 g, 66%) was collected by filtration, and blast dried. To the obtained solid was added isopropyl alcohol (400 mL, 5 vol), and the mixture was heated to 50° C.-55° C. and stirred at 50° C.-55° C. for 1 hr. Then, the mixture was cooled to 25° C.-30° C., and stirred at 25° C.-30° C. for 1 hr. The resulting solid was filtered and suction-filtered for 10 min to give TOLM (76 g, 62%).

7

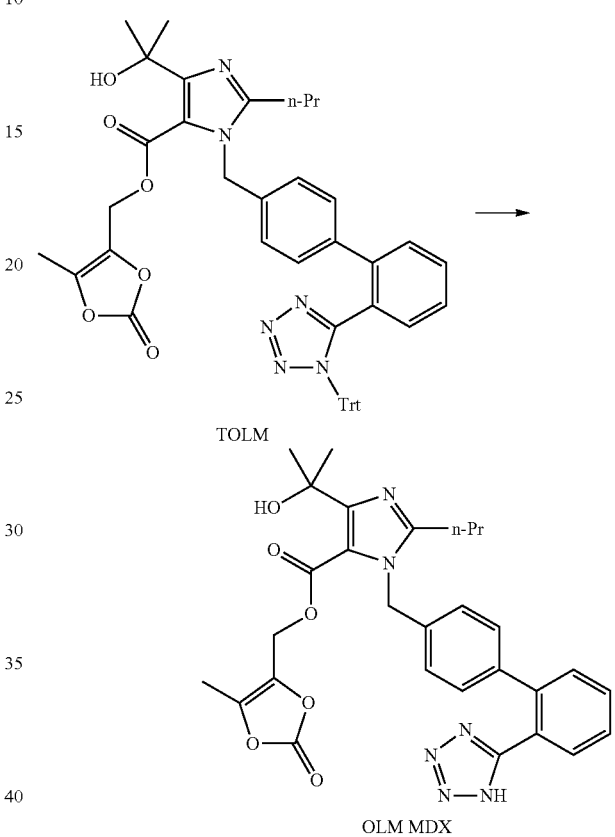

TOLM

OLM MDX

To TOLM (75 g) were successively added acetic acid:water=1:1 (330 mL, 4.4 vol) and concentrated sulfuric acid (5.4 mL, 1.08 eq). The obtained mixture was stirred at 25° C.-30° C. for 1 hr. Using TLC (thin layer chromatography) (TLC eluent: 10% methanol/methylene chloride, detection method: UV), complete disappearance of TOLM was confirmed.

The reaction mixture was filtered and insoluble trityl alcohol was removed. The aqueous layer was adjusted to pH 2-3 by adding 25% aqueous sodium carbonate solution (initial pH of the reaction mixture was 4-4.5). The reaction mixture was stirred for 5 min, methylene chloride (225 mL, 3 vol) was added thereto, and the mixture was stirred for 5 min. Stirring was stopped, and the mixture was stood and partitioned. The aqueous layer was extracted with methylene chloride (2×225 mL, 2×3 vol), the extracts were combined with the organic layer, deionized water (375 mL, 5 vol) was added, and the mixture was stirred for 5 min. Stirring was stopped, and the mixture was stood for 5 min and partitioned. To the organic layer was added saturated brine (375 mL, 5 vol), and the mixture was stirred for 5 min, left standing and partitioned. The organic layer was concentrated under reduced pressure at 40° C.-45° C. to give crude OLM MDX (49 g, 93%) as a pale-yellow solid.

(8) Purification of OLM MDX

To the crude OLM MDX (49 g, 1 eq) obtained in the above-mentioned (7) was added acetone (735 mL, 15 vol), and the mixture was stirred at 55° C.-60° C. for 10 min. Furthermore, the reaction mixture was stirred at the same temperature for 15 min, and acetone was evaporated under normal pressure. Heating was stopped when a solid was precipitated, and the mixture was cooled to 25° C.-30° C. The precipitated solid was collected by filtration and dried with suction for 30 min to give OLM MDX (41 g, 83%).

To the OLM MDX obtained above was added isopropyl alcohol (164 mL, 4 vol), and the mixture was heated to 55° C.-60° C., and stirred at 55° C.-60° C. for 1 hr. Heating was stopped and the mixture was gradually cooled to 25° C.-30° C., and stirred at 25° C.-30° C. for 30 min. The precipitated solid was filtered and dried with suction to give OLM MDX (41 g, 100%).

The OLM MDX (41 g) obtained above and acetone (about 1 L) were heated to 55° C.-60° C., and stirred at 55° C.-60° C. for 25 min. Acetone was evaporated under normal pressure until the mixture became cloudy, and the mixture was gradually cooled to 25° C.-30° C. The precipitated solid was collected by filtration and dried with suction for 30 min to give OLM MDX (34 g, 83%). The HPLC purity of the obtained OLM MDX was 99.66%.

The OLM MDX (44 g) obtained above was dissolved in acetone (about 1.2 L), and the mixture was stirred at 55° C.-60° C. for 10 min. Acetone was evaporated under normal pressure until the solution became cloudy, and the solution was gradually cooled to 25° C.-30° C. The precipitated solid was collected by filtration, dried with suction for 30 min, blast dried for 1 hr, and further blast dried at 40° C.-45° C. for 5 hr to give OLM MDX (36 g) as a white solid. The HPLC purity of the obtained OLM MDX was 99.8%.

Example 11

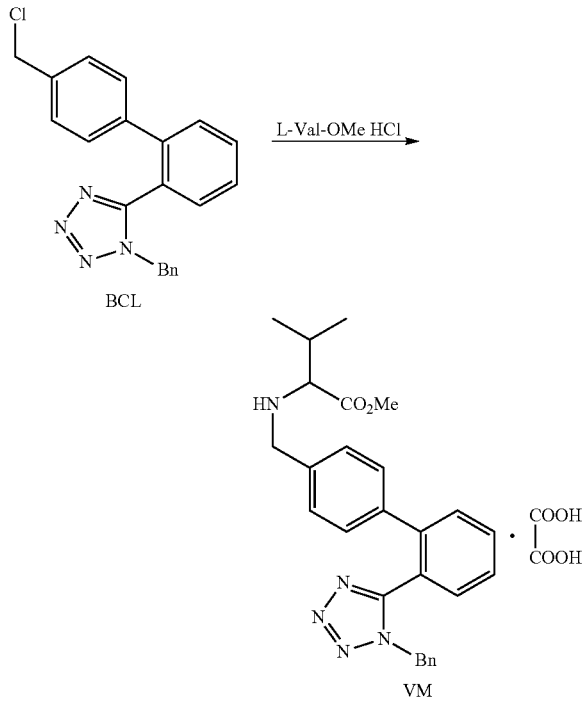

L-valine methyl ester hydrochloride (L-Val-OMe.HCL, 10 g, 1 eq) was dissolved in methylene chloride, and the mixture was adjusted to pH 9-10 by adding 10% aqueous sodium carbonate solution, and extracted with methylene chloride (50 mL, 5 vol). The organic layer was dried over sodium sulfate, filtered, and concentrated under reduced pressure at 40° C.-45° C. 1.46 g to from the obtained L-valine methyl ester was dissolved in dimethylformamide (12 mL, 3 vol). To the obtained solution was added diisopropylethylamine (4.58 mL, 2.5 eq) and the mixture was stirred for 5 min. BCL (4 g, 1 eq) and tetrabutylammonium iodide (0.20 g, 0.05 eq) were added thereto, and the mixture was stirred at 45° C.-50° C. for 24 hr. To the reaction mixture was added water (40 mL, 10 vol) to quench the reaction. Ethyl acetate (20 mL, 5 vol) was added, and the mixture was stirred for 5 min and partitioned. The organic layer was washed with water (20 mL, 5 vol) and then with saturated brine (20 mL, 5 vol), dried over sodium sulfate, filtered, and cooled to 10° C.-15° C. Oxalic acid (1.5 g, 1.1 eq) was added, and the mixture was cooled to 5° C. and stirred at the same temperature for 30 min. The precipitated solid was filtered, washed with n-heptane (20 mL, 5 vol), and dried with suction for 10 min to give an oxalate of VM (4.4 g, 68%).

Using the obtained VM as a starting material compound, VAL can be synthesized by the method described in the present specification.

Example 12

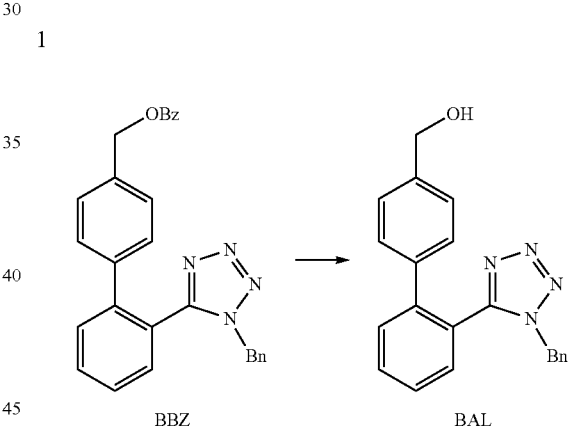

BBZ (140 g, 1 eq) was dissolved in THF (560 mL, 4 vol), 20% aqueous sodium hydroxide solution (280 mL, 2 vol) was added thereto, and the mixture was stirred at 60° C.-65° C. for 6 hr. Using TLC (TLC: 30% ethyl acetate/hexane, detection method: UV), complete consumption of BBZ was confirmed. The reaction mixture was concentrated under reduced pressure at 40° C.-45° C., to the concentrated residue was added t-butyl methyl ether (700 mL, 5 vol), and the mixture was stirred for 5 min and partitioned. The aqueous layer was extracted with t-butyl methyl ether (700 mL, 2×2.5 vol), the extracts were combined with the organic layer, and the mixture was washed with water (700 mL, 2×2.5 vol) and further with saturated brine (350 mL, 2.5 vol). The organic layer was dried over sodium sulfate and concentrated under reduced pressure at 40° C.-45° C. to give crude BAL (111 g, 103%).

To the obtained crude BAL was added diisopropyl ether (700 mL, 5 vol), and the mixture was stirred at 60° C.-65° C. for 1 hr and cooled to 25° C.-30° C. The precipitated solid was filtered, washed with diisopropyl ether (140 mL, 1 vol), and dried with suction for 30 min, after which dried at 50° C.-55° C. for 2 hr to give BAL (92.5 g, 92%).

2

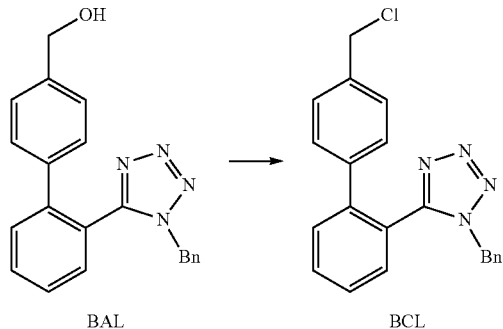 [SMILES: OCc1ccc(-c2ccccc2-c2nnnn2Cc2ccccc2)cc1 ; ClCc1ccc(-c2ccccc2-c2nnnn2Cc2ccccc2)cc1]

BAL (90 g, 1 eq) was dissolved in methylene chloride (900 mL, 10 vol), the mixture was cooled to 0° C.-5° C., and thionyl chloride (37.5 mL, 1.2 eq) was added at 0° C.-5° C. over 10 min. The reaction mixture was stirred at 0° C.-5° C. for 1 hr, warmed to 25° C.-30° C., and further stirred at 25° C.-30° C. for 3 hr. Using TLC (TLC: 50% ethyl acetate/hexane, detection method: UV), complete consumption of BAL was confirmed. To the reaction mixture was added ice water (540 mL, 6 vol), and the mixture was stirred for 10 min and partitioned. The organic layer was successively washed with water (2×540 mL, 2×6 vol), saturated aqueous sodium hydrogen carbonate (540 mL, 6 vol), water (540 mL, 6 vol) and saturated brine (540 mL, 6 vol). The organic layer was dried over sodium sulfate (45 g) and concentrated under reduced pressure at 40° C.-45° C. to give crude BCL (110 g).

To the obtained crude BCL was added ethyl acetate (90 mL, 1 vol), and the mixture was dissolved. Furthermore, n-heptane (360 mL, 4 vol) was added, and the mixture was stirred at 0° C.-5° C. for 2 hr. The precipitated solid was filtered, washed with n-heptane (90 mL, 1 vol), and dried with suction for 20 min and further dried at 50° C.-55° C. for 2 hr to give BCL (89 g, 91%) as a beige solid.

3

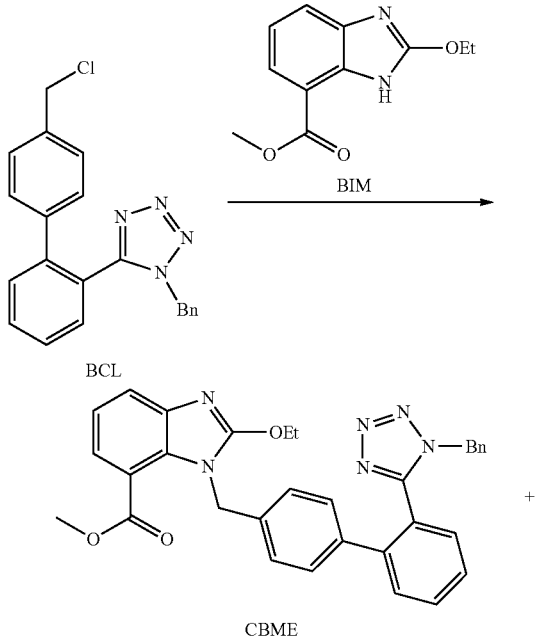

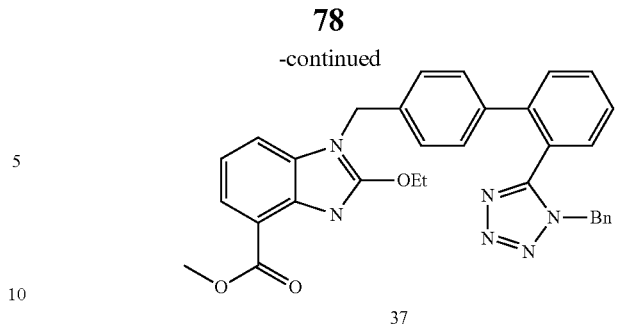

BIM (20 g, 1 eq) was dissolved in dimethylacetamide:methanol [(1:4), (100 mL, 5 vol)], potassium carbonate (18.8 g, 1.5 eq) was added thereto, and the mixture was stirred at 25° C.-30° C. for 15 min. Furthermore, BCL (34.4 g, 1.05 eq) and tetrabutylammonium iodide (1.67 g, 0.05 eq) were added thereto, and the mixture was stirred at the same temperature for 26 hr. Using TLC (TLC: 40% ethyl acetate/hexane, detection method: UV), complete consumption of BIM was confirmed. To the reaction mixture was added water (200 mL, 10 vol), the mixture was stirred for 2 hr, and the precipitated pink solid was filtered. The obtained solid was washed with water (40 mL, 2 vol), dried with suction for 15 min, and blast dried at 50° C.-55° C. for 4 hr to give a mixture of crude CBME and compound 37 (49 g, CBME:compound 37=6:1 (molar ratio)). The crude product was directly used for the next step (4).

4

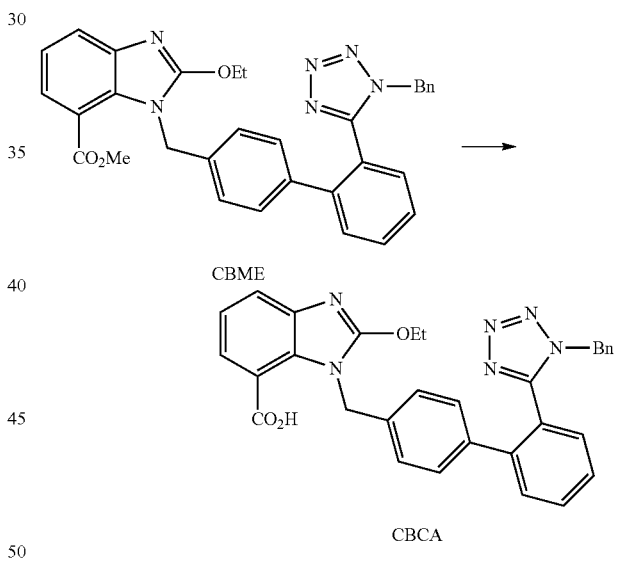

To the crude CBME (20 g, 1 eq) obtained in the above-mentioned (3) were added methanol:water [(1:1) (160 mL)] and sodium hydroxide (4.4 g, 3 eq) at 25° C.-30° C., and the reaction mixture was stirred at 75° C.-80° C. for 4 hr. Using TLC (TLC: 40% ethyl acetate/hexane, detection method: UV), complete consumption of CBME was confirmed. The reaction mixture was cooled to 25° C.-30° C., and the organic solvent was evaporated under reduced pressure at 40° C.-45° C. To the concentrated residue was added water (200 mL, 10 vol), and the aqueous layer was washed with t-butyl methyl ether (100 mL, 2×5 vol). The aqueous layer was adjusted to pH 5.5-6.5 by adding acetic acid (6 mL, 0.3 vol), the obtained slurry was stirred at 25° C.-30° C. for 1 hr, and the precipitated solid was filtered. The solid was washed with water (40 mL, 2 vol), dried with suction for 15 min, and further dried at 50° C.-55° C. for 4 hr to give crude CBCA (16 g).

To the obtained crude CBCA (16 g) were added ethyl acetate (160 mL, 10 vol) and dicyclohexylamine (DCHA) (8.2 g, 1.5 eq), and the mixture was stirred at 25° C.-30° C. for 2 hr. The precipitated solid was filtered, washed with ethyl acetate (80 mL, 5 vol), dried with suction for 15 min, and further blast dried at 50° C.-55° C. for 4 hr to give a DCHA salt (16 g) of CBCA. To the salt was added isopropyl alcohol (192 mL, 12 vol) at 25° C.-30° C., and the salt was dissolved by heating to 75° C.-85° C., and the mixture was stirred for 15 min. Thereafter, the reaction mixture was cooled to 25° C.-30° C., and stirred at the same temperature for 2 hr. The precipitated solid was filtered, washed with isopropyl alcohol (32 mL, 2 vol), dried with suction for 15 min, and further blast dried at 50° C.-55° C. for 4 hr to give a pure DCHA salt (13 g) of CBCA. To this salt was added 25% aqueous sodium hydroxide solution (120 mL, 10 vol) at 25° C.-30° C., and the mixture was stirred for 15 min, adjusted to pH 5.5-6.5 by adding acetic acid (5.8 mL, 0.48 vol), and extracted with methylene chloride (120 mL, 2×5 vol). The extract was combined with the organic layer, and the mixture was washed with water (120 mL, 2×5 vol) and further with saturated brine (60 mL, 5 vol). The organic layer was dried over sodium sulfate, and concentrated under reduced pressure at 40° C.-45° C. to give CBCA (9 g, 47% from BCL).

Starting Material Synthesis Method

Synthesis of HBT (1) N-Benzylbenzamide

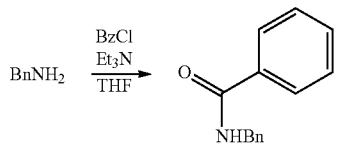

To a mixture of benzylamine (75.0 g, 0.700 mol), THF (300 mL) and triethylamine (70.8 g, 134 g, 0.700 mol) was added benzoyl chloride (98.4 g, 0.700 mol) dropwise at not more than 2° C. The mixture was warmed and stirred at 12° C.-35° C. for 3 hr. The progress of the reaction was confirmed by TLC (eluent: toluene/ethyl acetate (4:1)). To the reaction mixture was added water (165 mL) at not more than 16° C., the mixture was extracted with ethyl acetate (60 mL), and the aqueous layer was further extracted with ethyl acetate (150 mL). The combined extracts were washed twice with 5% aqueous citric acid solution (50 mL), three times with 20% brine (75 mL), and dried by adding magnesium sulfate (20 g). Silica gel (12 g) was added, and the mixture was filtered through silica gel. The filtrate was concentrated (263 g) in a 40° C. bath under reduced pressure until precipitation started. To the concentrate was added ethyl acetate (41.5 g), the solid was dissolved in a 60° C. bath, and cooled to 20° C. over 2 hr, and ethyl acetate (40 mL) was added. The mixture was further cooled to 5° C., and the crystals were collected by filtration, and washed with cold ethyl acetate (75 mL). The crystals were dried under reduced pressure at 40° C. to give N-benzylbenzamide (116 g, 78.5%) as white crystals.

Melting point: 104° C.-105° C.
IR (KBr): 3328 (NH), 1642 (C=O) cm$^{-1}$ $^1$H NMR (CDCl$_3$): δ=7.79 (d, J=8.0 Hz, 2H, o-Bz), 7.50 (t, J =8.0 Hz, 1H, p-Bz), 7.43 (t, J=8.0, 2H, m-Bz), 7.37-7.35 (m, 4H, Ph), 7.32 (m, 1H, Ph), 6.41 (br s, 1H, NH), 4.65 (d, J=5.6 Hz, 2H, CH$_2$)

(2) 1-benzyl-5-phenyl-1H-tetrazole (HBT)

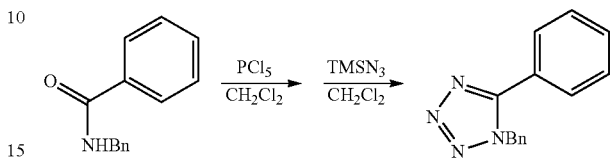

To a mixture of N-benzylbenzamide (62.5 g, 0.296 mol) and methylene chloride (570 mL) was added phosphorus pentachloride (67.9 g, 0.326 mol) in five portions at −15° C. to −8° C. The mixture was warmed to 21° C. over 3 hr, and concentrated to 0.17 L under reduced pressure at not more than 21° C. To the mixture was added methylene chloride (450 mL). Azidotrimethylsilane (50.3 g, 0.436 mol) was added dropwise at not more than −8° C. over 0.5 hr, and the mixture was rinsed with methylene chloride (5 mL). The reaction mixture was warmed to room temperature, and stirred for 4 hr. Using TLC (eluent: toluene/ethyl acetate (4:1)), disappearance of N-benzylbenzamide was confirmed. To the reaction mixture was added saturated aqueous sodium hydrogen carbonate solution (1000 mL) at not more than 17° C. Furthermore, saturated aqueous sodium hydrogen carbonate solution (1300 mL) was added, and the mixture was partitioned. To the aqueous layer was added methylene chloride (450 mL), and the mixture was extracted. The extract was combined with the organic layer, and the mixture was washed with 20% brine (300 g), dried over magnesium sulfate (20 g), and concentrated under reduced pressure at not more than 40° C. to give a crude product (69.8 g, theoretical yield 99.8%) as a cloudy yellow oily substance. To the crude product (69.0 g) was added isopropyl alcohol (75.9 mL), and the mixture was dissolved by heating, hot-filtered, and rinsed with isopropyl alcohol (4.7 mL). The filtrate was cooled to −1° C. over 7 hr, during which seeding was performed at 38° C. The crystals were collected by filtration, washed with cold isopropyl alcohol (20 mL), and dried under reduced pressure to give the title compound (65.4 g, purification yield 94.9%, 94.7% from the main starting to material).

Melting point: 66.0° C.-67.5° C.
IR (KBr):1606 cm$^{-1}$
$^1$H NMR (CDCl$_3$): δ=7.58 (d, J=7.9 Hz, 2H, 5-Ph), 7.57 (t, J =7.9 Hz, 1H, 5-Ph), 7.50 (t, J=7.9 Hz, 2H, 5-Ph), 7.37-7.34 (m, 3H, Ph), 7.17-7.15 (m, 2H, Ph), 5.62 (s, CH$_2$)
MS:237 (MH$^+$)

Synthesis of p-bromobenzyl=acetate (BBA)

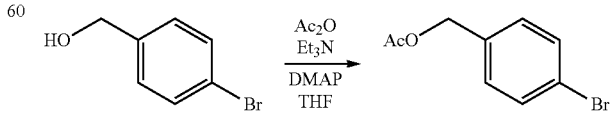

To a solution of p-bromobenzyl alcohol (250 g, 1.34 mol) in THF (1000 mL) were added acetic anhydride (164 g, 1.60 mol) and THF (14 mL) at 8° C.-9° C. To this mixture was added triethylamine (203 g, 2.01 mol) at 5° C.-8° C. over 8 min, and the mixture was rinsed with THF (13 mL). To this reaction mixture were added 4-(dimethylamino)pyridine (8.17 g, 66.9 mmol) and THF (21 mL) at 6° C. (inside temperature raised to 28° C.). The reaction was confirmed by TLC (eluent: hexane/ethyl acetate (1:1 and 2:1)). The reaction mixture was stirred at room temperature for 15 hr, methanol was added at 22° C.-25° C. and the mixture was concentrated under reduced pressure at not more than 45° C. To the concentrate were added ethyl acetate (2000 mL) and cold 1 mol/L hydrochloric acid (1000 mL), and the mixture was partitioned. To the organic layer were added 4% aqueous sodium hydrogen carbonate solution (1000 mL), 5% aqueous sodium hydrogen carbonate solution (100 mL) and aqueous sodium hydrogen carbonate solution (500 mL), and the mixture was partitioned. The organic layer was washed with water (1000 mL), dried over magnesium sulfate (77 g) and concentrated under reduced pressure to give the title compound (308 g, 100%).

$^1$H NMR (CDCl$_3$): δ=7.49 (d, J=8.2 Hz, 2H, Ar), 7.23 (d, J 8.2 Hz, 2H, Ar), 5.05 (s, 2H, CH$_2$), 2.10 (s, 3H, Ac)

The invention claimed is:

1. A method of producing a biaryltetrazole compound represented by the formula [3']:

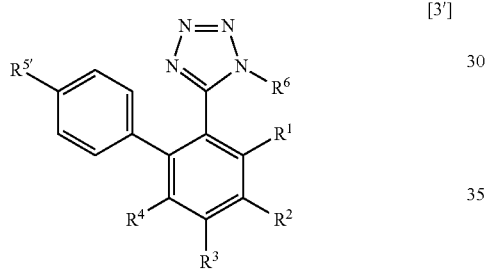

wherein
R$^1$ to R$^4$ are each independently a hydrogen atom, or an alkyl group, an aralkyl group or an aryl group, each of which optionally has 1 to 5 substituents that are the same or different and that are selected from
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated C$_{1-6}$ alkyl, mono- or di-C$_{1-6}$ alkyl-amino, C$_{6-14}$ aryl, mono- or di-C$_{6-14}$ aryl-amino, C$_{3-8}$ cycloalkyl, C$_{1-6}$ alkoxy, C$_{1-6}$ alkoxy-C$_{1-6}$ alkoxy, C$_{1-6}$ alkylsulfanyl, C$_{1-6}$ alkylsulfinyl, C$_{1-6}$ alkylsulfonyl, optionally esterified carboxy, carbamoyl, thiocarbamoyl, mono- or di-C$_{1-6}$ alkyl-carbamoyl, mono- or di-C$_{6-14}$ aryl-carbamoyl, sulfamoyl, mono- or di-C$_{1-6}$ alkyl-sulfamoyl, and mono- or di-C$_{6-14}$ aryl-sulfamoyl;
(7) mono- or di-C$_{1-6}$ alkyl-amino;
(8) mono- or di-C$_{6-14}$ aryl-amino;
(9) mono- or di-C$_{7-14}$ aralkyl-amino;
(10) N-C$_{1-6}$ alkyl-N-C$_{6-14}$ aryl-amino;
(11) N-C$_{1-6}$ alkyl-N-C$_{7-14}$ aralkyl-amino;
(12) C$_{3-8}$ cycloalkyl;
(13) optionally halogenated C$_{1-6}$ alkoxy;
(14) C$_{1-6}$ alkylsulfanyl;
(15) C$_{1-6}$ alkylsulfinyl;
(16) C$_{1-6}$ alkylsulfonyl;
(17) optionally esterified carboxy;
(18) C$_{1-6}$ alkyl-carbonyl;
(19) C$_{3-8}$ cycloalkyl-carbonyl;
(20) C$_{6-14}$ aryl-carbonyl;
(21) carbamoyl;
(22) thiocarbamoyl;
(23) mono- or di-C$_{1-6}$ alkyl-carbamoyl;
(24) mono- or di-C$_{6-14}$ aryl-carbamoyl;
(25) N-C$_{1-6}$ alkyl-N-C$_{6-14}$ aryl-carbamoyl;
(26) mono- or di-5- to 7-membered heterocyclyl-carbamoyl;
(27) C$_{1-6}$ alkyl-carbonylamino optionally substituted by carboxy;
(28) C$_{6-14}$ aryloxy optionally substituted by 1 to 3 substituents selected from halogen atom, hydroxy, amino, nitro, cyano, optionally halogenated C$_{1-6}$ alkyl, mono- or di-C$_{1-6}$ alkyl-amino, C$_{6-14}$ aryl, mono- or di-C$_{6-14}$ aryl-amino, C$_{3-8}$ cycloalkyl, C$_{1-6}$ alkoxy, C$_{1-6}$ alkoxy-C$_{1-6}$ alkoxy, C$_{1-6}$ alkylsulfanyl, C$_{1-6}$ alkylsulfinyl, C$_{1-6}$ alkylsulfonyl, optionally esterified carboxy, carbamoyl, thiocarbamoyl, mono- or di-C$_{1-6}$ alkyl-carbamoyl, mono- or di-C$_{6-14}$ aryl-carbamoyl, sulfamoyl, mono- or di-C$_{1-6}$ alkyl-sulfamoyl and mono- or di-C$_{6-14}$ aryl-sulfamoyl;
(29) C$_{6-14}$ aryl optionally substituted by 1 to 3 substituents selected from halogen atom, hydroxy, amino, nitro, cyano, optionally halogenated C$_{1-6}$ alkyl, mono- or di-C$_{1-6}$ alkyl-amino, C$_{6-14}$ aryl, mono- or di-C$_{6-14}$ aryl-amino, C$_{3-8}$ cycloalkyl, C$_{1-6}$ alkoxy, C$_{1-6}$ alkoxy-C$_{1-6}$ alkoxy, C$_{1-6}$ alkylsulfanyl, C$_{1-6}$ alkylsulfinyl, C$_{1-6}$ alkylsulfonyl, optionally esterified carboxy, carbamoyl, thiocarbamoyl, mono- or di-C$_{1-6}$ alkyl-carbamoyl, mono- or di-C$_{6-14}$ aryl-carbamoyl, sulfamoyl, mono- or di-C$_{1-6}$ alkyl-sulfamoyl and mono- or di-C$_{6-14}$ aryl-sulfamoyl;
(30) heterocyclyl-oxy;
(31) sulfamoyl;
(32) mono- or di-C$_{1-6}$ alkyl-sulfamoyl;
(33) mono- or di-C$_{6-14}$ aryl-sulfamoyl;
(34) C$_{7-14}$ aralkyloxy optionally substituted by 1 to 3 substituents selected from halogen atom, hydroxy, amino, nitro, cyano, optionally halogenated C$_{1-6}$ alkyl, mono- or di-C$_{1-6}$ alkyl-amino, C$_{6-14}$ aryl, mono- or di-C$_{6-14}$ aryl-amino, C$_{3-8}$ cycloalkyl, C$_{1-6}$ alkoxy, C$_{1-6}$ alkoxy-C$_{1-6}$ alkoxy, C$_{1-6}$ alkylsulfanyl, C$_{1-6}$ alkylsulfinyl, C$_{1-6}$ alkylsulfonyl, optionally esterified carboxy, carbamoyl, thiocarbamoyl, mono- or di-C$_{1-6}$ alkyl-carbamoyl, mono- or di-C$_{6-14}$ aryl-carbamoyl, sulfamoyl, mono- or di-C$_{1-6}$ alkyl-sulfamoyl and mono- or di-C$_{6-14}$ aryl-sulfamoyl;
(35) C$_{1-6}$ alkyl-carbonyloxy;
(36) C$_{1-6}$ alkoxy-carbonyl; and
(37) tri-C$_{1-6}$ alkylsilyloxy;
R$^{5'}$ is a methyl group, a methyl group substituted by a protected hydroxyl group, or a lower alkoxycarbonyl group, and
R$^6$ is a tetrazolyl-protecting group,
or a salt thereof,
comprising reacting a 2-phenylazole derivative represented by the formula [1']:

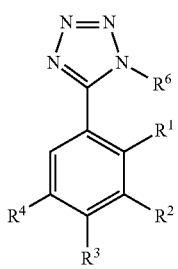

wherein
R[1] to R[4] are each independently a hydrogen atom, or an alkyl group, an aralkyl group or an aryl group, each of which optionally has 1 to 5 substituents that are the same or different and that are selected from
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl, and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N-$C_{1-6}$ alkyl-N-$C_{6-14}$ aryl-amino;
(11) N-$C_{1-6}$ alkyl-N-$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxy;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N-$C_{1-6}$ alkyl-N-$C_{6-14}$ aryl-carbamoyl;
(26) mono- or di-5- to 7-membered heterocyclyl-carbamoyl;
(27) $C_{1-6}$ alkyl-carbonylamino optionally substituted by carboxy;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl; and
(37) tri-$C_{1-6}$ alkylsilyloxy;
and
R[6] is a tetrazolyl-protecting group,
or a salt thereof with a benzene derivative represented by the formula [2']:

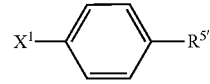

wherein R[5'] is a methyl group, a methyl group substituted by a protected hydroxyl group, or a lower alkoxycarbonyl group, and X' is a leaving group,
in the presence of a metal catalyst, a base and one or more kinds of compounds selected from the group consisting of the following (a)-(c);
(a) a metal salt of glutarate,
(b) a metal salt of 4-dodecylbenzenesulfonate, and
(c) a metal salt of bis(2-ethylhexyl) phosphate.

2. The method according to claim 1, wherein the reaction is performed under conditions comprising further presence of a phosphine compound.

3. A method of producing a biaryltetrazole derivative represented by the formula [5]:

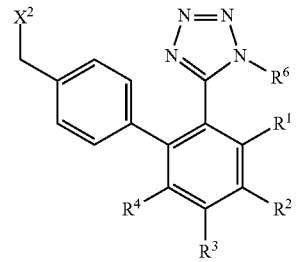

wherein
X² is a halogen atom,
R¹ to R⁴ are each independently a hydrogen atom, or an alkyl group, an aralkyl group or an aryl group, each of which optionally has 1 to 5 substituents that are the same or different and that are selected from
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl, and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N-$C_{1-6}$ alkyl-N-$C_{6-14}$ aryl-amino;
(11) N-$C_{1-6}$ alkyl-N-$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxy;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N-$C_{1-6}$ alkyl-N-$C_{6-14}$ aryl-carbamoyl;
(26) mono- or di-5- to 7-membered heterocyclyl-carbamoyl;
(27) $C_{1-6}$ alkyl-carbonylamino optionally substituted by carboxy;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl; and
(37) tri-$C_{1-6}$ alkylsilyloxy;
and
R⁶ is a tetrazolyl-protecting group,
or a salt thereof, comprising
1) in the biaryltetrazole compound represented by the formula [3']:

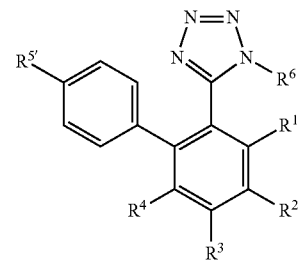

[3']

wherein
R¹ to R⁴ are each independently a hydrogen atom, or an alkyl group, an aralkyl group or an aryl group, each of which optionally has 1 to 5 substituents that are the same or different and that are selected from
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl, and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N-$C_{1-6}$ alkyl-N-$C_{6-14}$ aryl-amino;
(11) N-$C_{1-6}$ alkyl-N-$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;

(15) $C_{1-6}$ alkylsulfinyl;
(16) $C_{1-6}$ alkylsulfonyl;
(17) optionally esterified carboxy;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N-$C_{1-6}$ alkyl-N-$C_{6-14}$ aryl-carbamoyl;
(26) mono- or di-5- to 7-membered heterocyclyl-carbamoyl;
(27) $C_{1-6}$ alkyl-carbonylamino optionally substituted by carboxy;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl; and
(37) tri-$C_{1-6}$ alkylsilyloxy;
$R^{5'}$ is a methyl group, a methyl group substituted by a protected hydroxyl group, or a lower alkoxycarbonyl group, and
$R^6$ is a tetrazolyl-protecting group,
which is obtained by the method according to claim 2, or a salt thereof,
1-A) (a) deprotecting the compound when $R^{5'}$ is a methyl group substituted by a protected hydroxyl group, and
(b) reducing the compound when $R^{5'}$ is a lower alkoxycarbonyl group, to give a compound represented by the formula [4]:

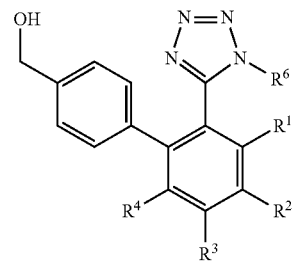

wherein
$R^1$ to $R^4$ are each independently a hydrogen atom, or an alkyl group, an aralkyl group or an aryl group, each of which optionally has 1 to 5 substituents that are the same or different and that are selected from
(1) halogen atom;
(2) hydroxy;
(3) amino;
(4) nitro;
(5) cyano;
(6) a heterocyclic group optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl, and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N-$C_{1-6}$ alkyl-N-$C_{6-14}$ aryl-amino;
(11) N-$C_{1-6}$ alkyl-N-$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxy;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N-$C_{1-6}$ alkyl-N-$C_{6-14}$ aryl-carbamoyl;
(26) mono- or di-5- to 7-membered heterocyclyl-carbamoyl;
(27) $C_{1-6}$ alkyl-carbonylamino optionally substituted by carboxy;
(28) $C_{6-14}$ aryloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
- (30) heterocyclyl-oxy;
- (31) sulfamoyl;
- (32) mono- or di-$C_{1-6}$ alkyl-sulfamoyl;
- (33) mono- or di-$C_{6-14}$ aryl-sulfamoyl;
- (34) $C_{7-14}$ aralkyloxy optionally substituted by 1 to 3 substituents selected from halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxy, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
- (35) $C_{1-6}$ alkyl-carbonyloxy;
- (36) $C_{1-6}$ alkoxy-carbonyl; and
- (37) tri-$C_{1-6}$ alkylsilyloxy;

and
$R^6$ is a tetrazolyl-protecting group,
or a salt thereof, and further halogenating the compound; or
1-B) halogenating a compound represented by the formula [3'] when $R^{5'}$ of the compound represented by the formula [3'] is a methyl group.

4. A method of producing a compound represented by the formula [11]:

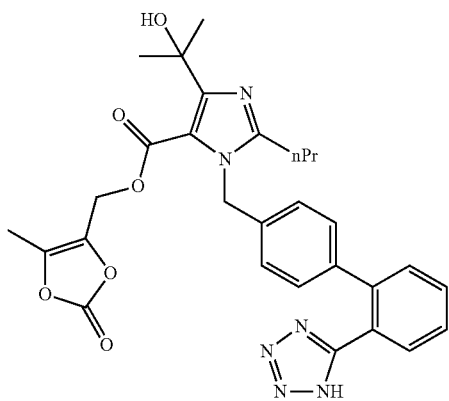

[11]

or a salt thereof, comprising
1) reacting a biaryltetrazole derivative represented by the formula [5']:

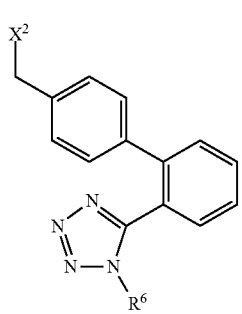

[5']

wherein $X^2$ is a halogen atom and $R^6$ is a tetrazolyl-protecting group,
which is obtained by the method according to claim 3, or a salt thereof
with a compound represented by the formula [6]:

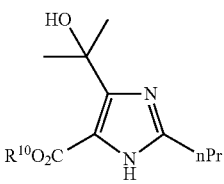

[6]

wherein $R^{10}$ is a carboxy-protecting group, or a salt thereof to give a compound represented by the formula [7]:

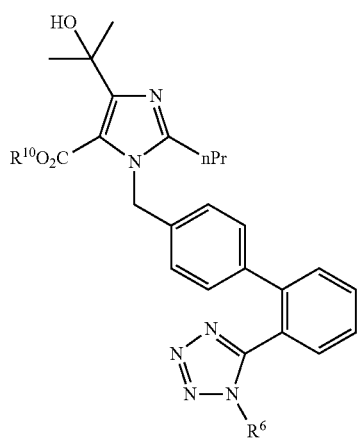

[7]

wherein $R^6$ is a tetrazolyl-protecting group and $R^{10}$ is a carboxy-protecting group, or a salt thereof;
2) removing $R^6$ of a compound represented by the formula [7] or a salt thereof to give a compound represented by the formula [Y1]:

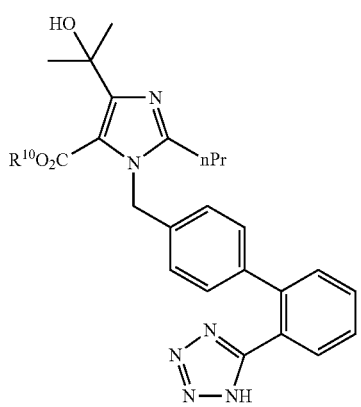

[Y1]

wherein $R^{10}$ is a carboxy-protecting group, or a salt thereof;
3) reacting a compound represented by the formula [Y1] or a salt thereof with a compound represented by the formula [Y3]: $R^{6'}$-$X^5$ (wherein $R^{6'}$ is a trityl group, and $X^5$ is a halogen atom) to give a compound represented by the formula [Y2]:

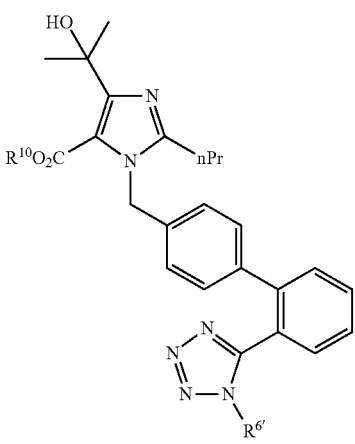

[Y2]

wherein R⁶' is a trityl group and R¹⁰ is a carboxy-protecting group, or a salt thereof;
  4) hydrolyzing a compound represented by the formula [Y2] or a salt thereof to give a compound represented by the formula [8']:

[8']

wherein R⁶' is a trityl group, or a salt thereof;
  5) reacting a compound represented by the formula [8'] or a salt thereof with a compound represented by the formula [9]:

[9]

to give a compound represented by the formula [10']:

[10']

wherein R⁶' is a trityl group, or a salt thereof; and
  6) removing R⁶' of a compound represented by the formula [10']or a salt thereof.

5. A method of producing a compound represented by the formula [16]:

[16]

or a salt thereof, comprising
  1) reacting a biaryltetrazole derivative represented by the formula [5']:

[5']

wherein R⁶ is a tetrazolyl-protecting group and X² is a halogen atom,
  which is obtained by the method according to claim 3, or a salt thereof with a compound represented by the formula [12]:

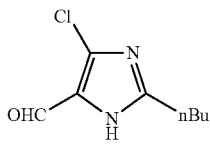
[12]

or a salt thereof
to give a compound represented by the formula [13]:

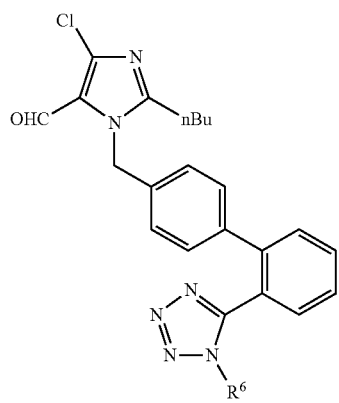
[13]

wherein $R^6$ is a tetrazolyl-protecting group, or a salt thereof; and

2-A) reducing a compound represented by the formula [13] or a salt thereof to give a compound represented by the formula [14]:

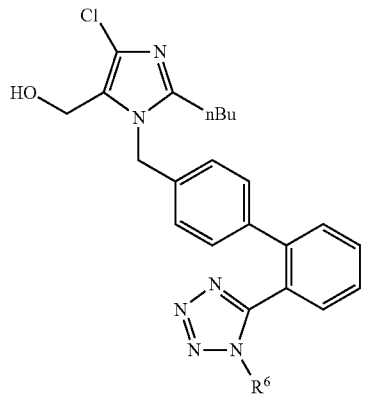
[14]

wherein $R^6$ is a tetrazolyl-protecting group, or a salt thereof, and further removing $R^6$; or 2-B) removing $R^6$ of a compound represented by the formula [13] or a salt thereof to give a compound represented by the formula [15]:

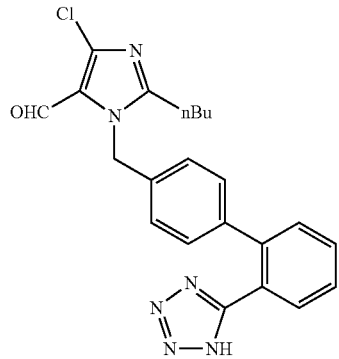
[15]

or a salt thereof, and further reducing the compound.

6. A method of producing a compound represented by the formula [23]:

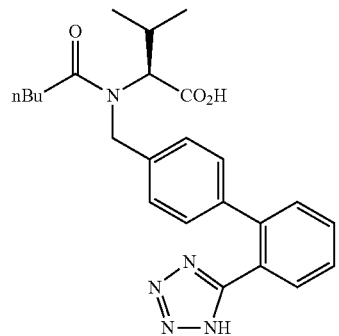
[23]

or a salt thereof, comprising
1) reacting a biaryltetrazole derivative represented by the formula [5']:

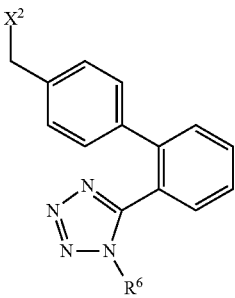
[5']

wherein $R^6$ is a tetrazolyl-protecting group and $R^{7o}$ is a carboxy-protecting group,
which is obtained by the method according to claim 3, or a salt thereof
with a compound represented by the formula [17]:

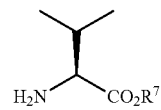
[17]

wherein $R^7$ is a carboxy-protecting group, or a salt thereof
to give a compound represented by the formula [18]:

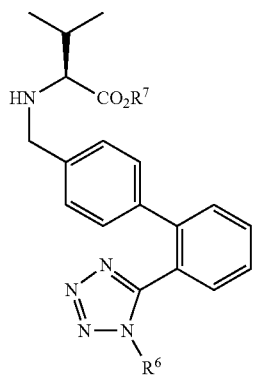
[18]

wherein $R^6$ is a tetrazolyl-protecting group and $R^7$ is a carboxy-protecting group, or a salt thereof;

2-A) removing $R^6$ of a compound represented by the formula [18] or a salt thereof to give a compound represented by the formula [19]:

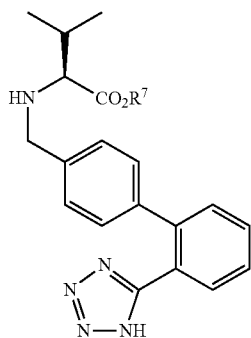

[19]

wherein $R^7$ is a carboxy-protecting group, or a salt thereof;

3-A) reacting a compound represented by the formula [19] or a salt thereof with a compound represented by the formula [20]: $CH_3CH_2CH_2CH_2CO-X^3$ (wherein $X^3$ is a leaving group) to give a compound represented by the formula [21]:

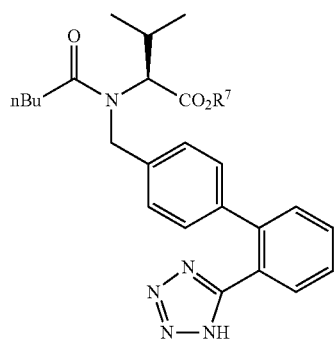

[21]

wherein $R^7$ is a carboxy-protecting group, or a salt thereof;

4-A) removing $R^7$ of a compound represented by the formula [21] or a salt thereof; or 2-B) reacting a compound represented by the formula [18] or a salt thereof with a compound represented by the formula [20] or a salt thereof to give a compound represented by the formula [22]:

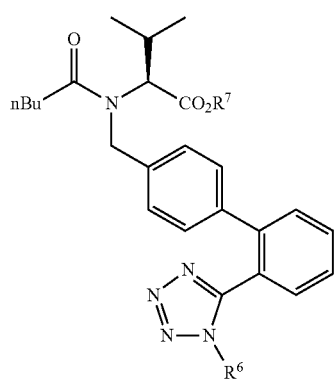

[22]

wherein $R^6$ is a tetrazolyl-protecting group and $R^7$ is a carboxy-protecting group, or a salt thereof; and 3-B) removing $R^6$ and $R^7$ of a compound represented by the formula [22] or a salt thereof.

7. A method of producing a compound represented by the formula [26]:

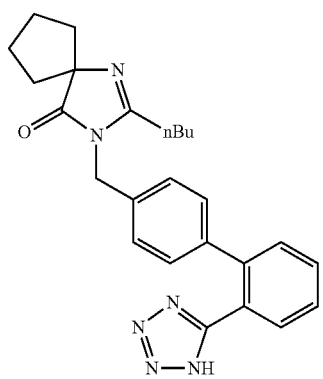

[26]

or a salt thereof, comprising reacting a biaryltetrazole derivative represented by the formula [5']:

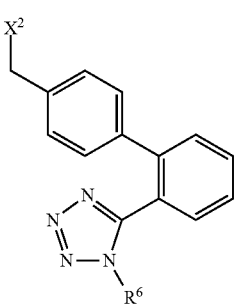

[5']

wherein $X^2$ is a halogen atom and $R^6$ is a tetrazolyl-protecting group, which is obtained by the method according to claim 3, or a salt thereof with a compound represented by the formula [24]:

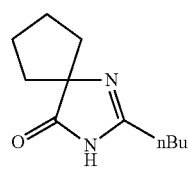

[24]

or a salt thereof to give a compound represented by the formula [25]:

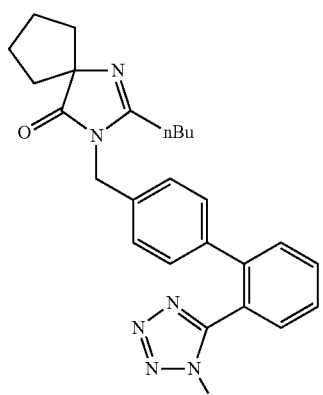

[25]

wherein R⁶ is a tetrazolyl-protecting group, or a salt thereof, and
further removing R⁶.

8. A method of producing a compound represented by the formula [35]:

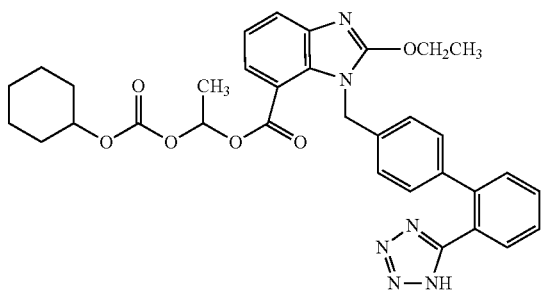

[35]

or a salt thereof, comprising
1) reacting a biaryltetrazole derivative represented by the formula [5']:

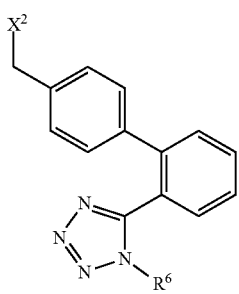

[5']

wherein X² is a halogen atom and R⁶ is a tetrazolyl-protecting group,
which is obtained by the method according to claim 3, or a salt thereof
with a compound represented by the formula [X]:

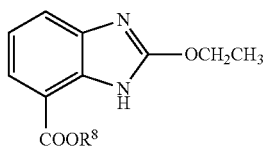

[X]

wherein R⁸ is a carboxy-protecting group, or a salt thereof
to give a compound represented by the formula [31]:

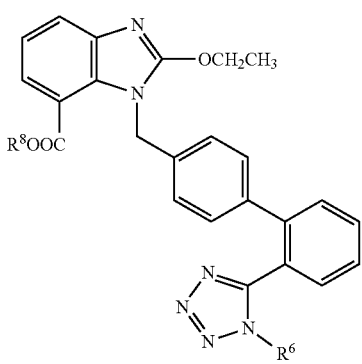

[31]

wherein R⁶ is a tetrazolyl-protecting group and R⁸ is a carboxy-protecting group, or a salt thereof;

2) removing R⁸ of a compound represented by the formula [31] or a salt thereof to give a compound represented by the formula [32]:

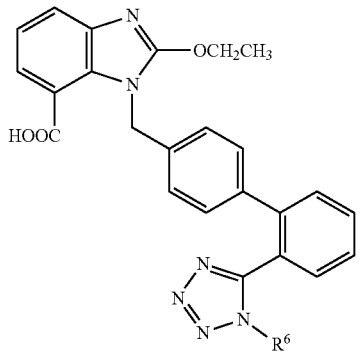

[32]

wherein R⁶ is a tetrazolyl-protecting group, or a salt thereof;
3) reacting a compound represented by the formula [32] or a salt thereof with a compound represented by the formula [33]:

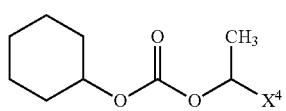

[33]

wherein X⁴ is a leaving group or a hydroxyl group, or a salt thereof
to give a compound represented by the formula [34]:

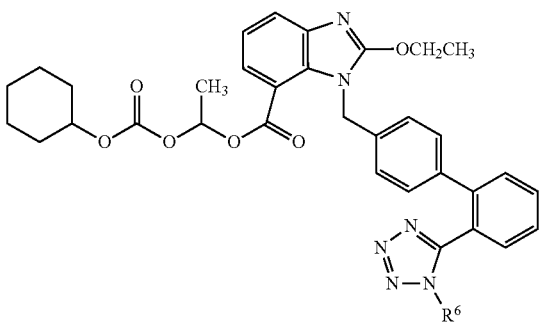

[34]

wherein R⁶ is a tetrazolyl-protecting group, or a salt thereof (compound [34]); and
4) removing R⁶ of a compound represented by the formula [34] or a salt thereof.

9. A method of producing a biaryltetrazole derivative represented by the formula [5]:

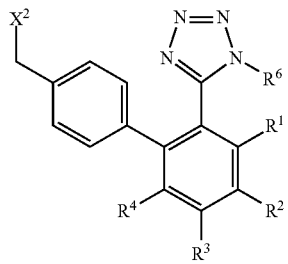

[5]

wherein X² is a halogen atom, and R¹ to R⁴ are each independently a hydrogen atom, or an alkyl group, an aralkyl group or an aryl group, each of which optionally has substituent(s), and R⁶ is a tetrazolyl-protecting group, or a salt thereof, comprising
1) in the biaryltetrazole compound represented by the formula [3']:

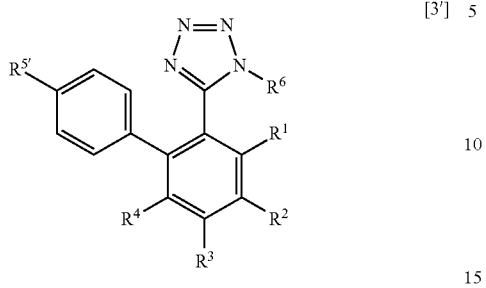

[3']

wherein $R^{5'}$ is a methyl group, a methyl group substituted by a protected hydroxyl group, or a lower alkoxycarbonyl group,
    which is obtained by the method according to claim 1, or a salt thereof,
    1-A) (a) deprotecting the compound when $R^{5'}$ is a methyl group substituted by a protected hydroxyl group, and (b) reducing the compound when $R^{5'}$ is a lower alkoxycarbonyl group, to give a compound represented by the formula [4]:

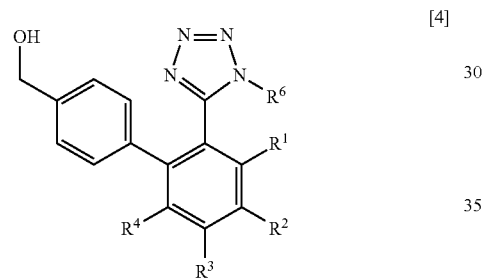

[4]

wherein $R^1$ to $R^4$ are each independently a hydrogen atom, or an alkyl group, an aralkyl group or an aryl group, each of which optionally has substituent(s), and $R^6$ is a tetrazolyl-protecting group, or a salt thereof, and further halogenating the compound; or
    1-B) halogenating a compound represented by the formula [3'] when $R^{5'}$ of the compound represented by the formula [3'] is a methyl group.

10. A method of producing a compound represented by the formula [11]:

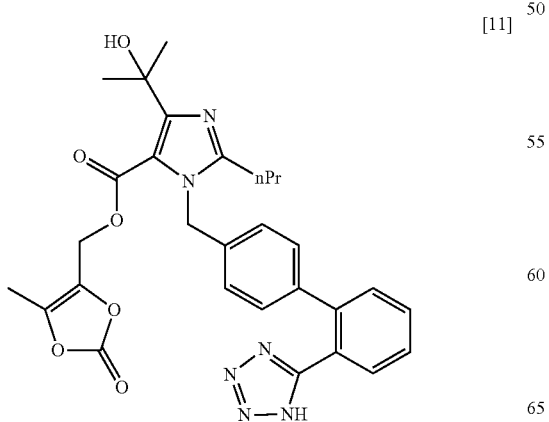

[11]

or a salt thereof, comprising
1) reacting a biaryltetrazole derivative represented by the formula [5']:

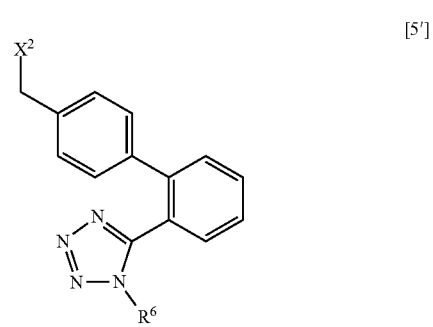

[5']

wherein $X^2$ is a halogen atom and $R^6$ is a tetrazolyl-protecting group,
    which is obtained by the method according to claim 9, or a salt thereof
    with a compound represented by the formula [6]:

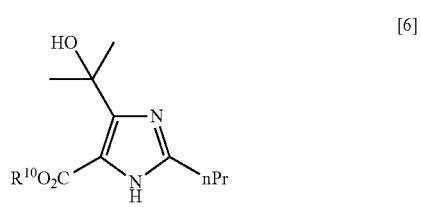

[6]

wherein $R^{10}$ is a carboxy-protecting group, or a salt thereof to give a compound represented by the formula [7]:

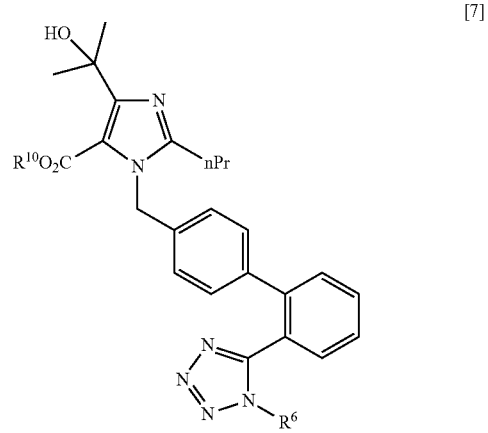

[7]

wherein $R^6$ is a tetrazolyl-protecting group and $R^{10}$ is a carboxy-protecting group, or a salt thereof;

2) removing $R^6$ of a compound represented by the formula [7] or a salt thereof to give a compound represented by the formula [Y1]:

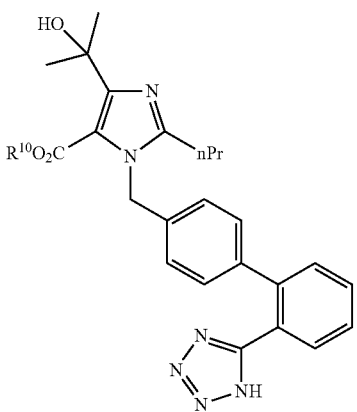

[Y1]

wherein $R^{10}$ is a carboxy-protecting group, or a salt thereof;
3) reacting a compound represented by the formula [Y1] or a salt thereof with a compound represented by the formula [Y3]: $R^{6'}$-$X^5$ (wherein $R^{6'}$ is a trityl group, and $X^5$ is a halogen atom) to give a compound represented by the formula [Y2]:

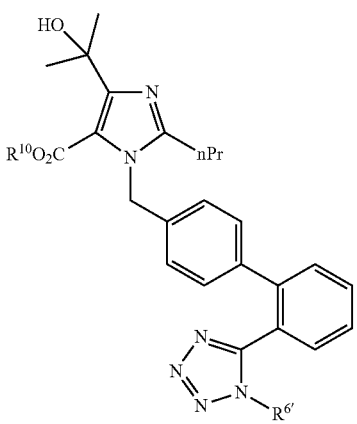

[Y2]

wherein $R^{6'}$ is a trityl group and $R^{10}$ is a carboxy-protecting group, or a salt thereof;
4) hydrolyzing a compound represented by the formula [Y2] or a salt thereof to give a compound represented by the formula [8']:

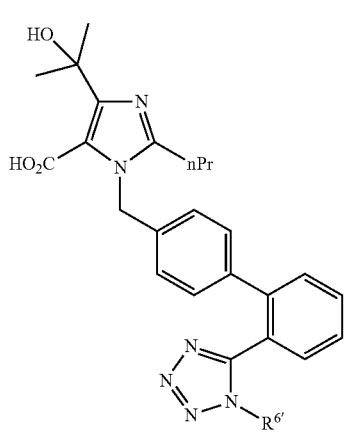

[8']

wherein $R^{6'}$ is a trityl group, or a salt thereof;
5) reacting a compound represented by the formula [8'] or a salt thereof with a compound represented by the formula [9]:

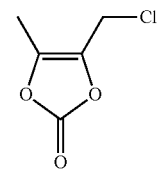

[9]

to give a compound represented by the formula [10']:

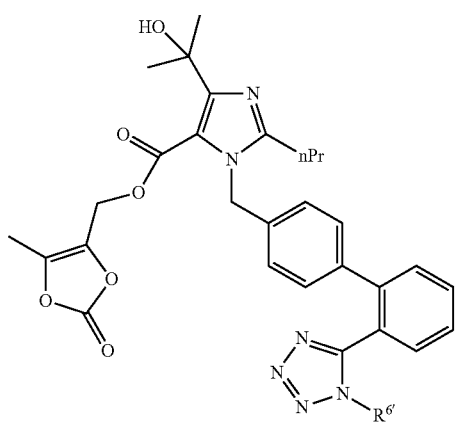

[10']

wherein $R^{6'}$ is a trityl group, or a salt thereof; and
6) removing $R^{6'}$ of a compound represented by the formula [10] or a salt thereof.

11. A method of producing a compound represented by the formula [16]:

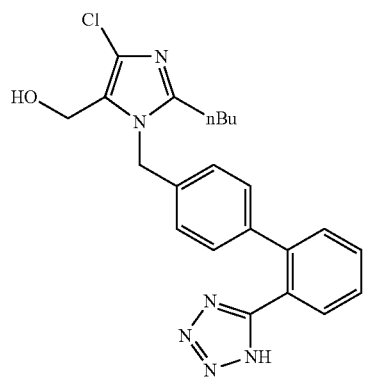

[16]

or a salt thereof, comprising
1) reacting a biaryltetrazole derivative represented by the formula [5']:

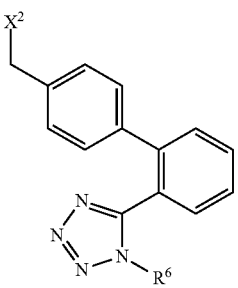

[5']

wherein $X^2$ is a halogen atom and $R^6$ is a tetrazolyl-protecting group,
which is obtained by the method according to claim 9, or a salt thereof
with a compound represented by the formula [12]:

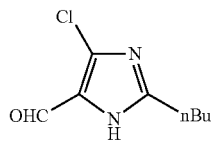
[12]

or a salt thereof
to give a compound represented by the formula [13]:

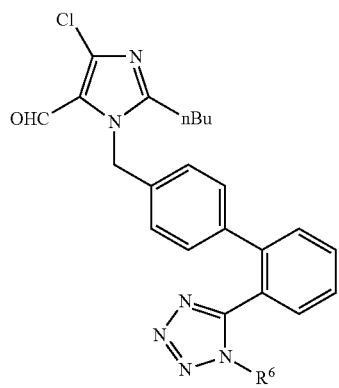
[13]

wherein $R^6$ is a tetrazolyl-protecting group, or a salt thereof; and

2-A) reducing a compound represented by the formula [13] or a salt thereof to give a compound represented by the formula [14]:

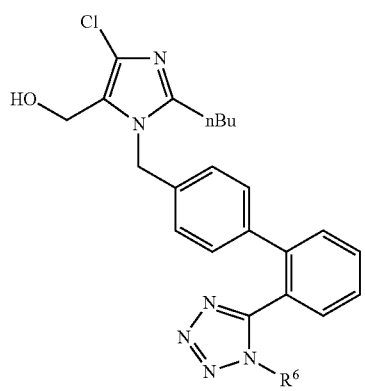
[14]

wherein $R^6$ is a tetrazolyl-protecting group, or a salt thereof, and further removing $R^6$; or 2-B) removing $R^6$ of a compound represented by the formula [13] or a salt thereof to give a compound represented by the formula [15]:

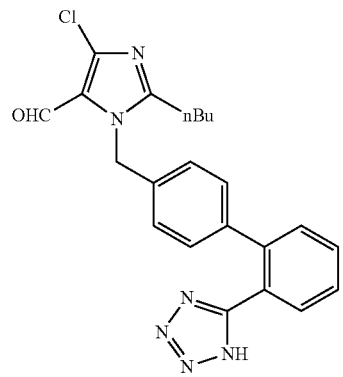
[15]

or a salt thereof, and further reducing the compound.

12. A method of producing a compound represented by the formula [23]:

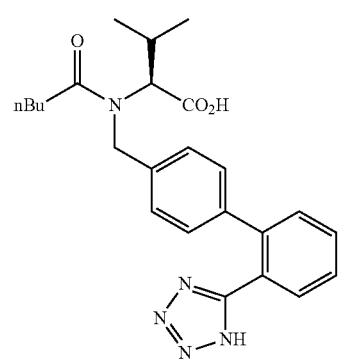
[23]

or a salt thereof, comprising 1) reacting a biaryltetrazole derivative represented by the formula [5′]:

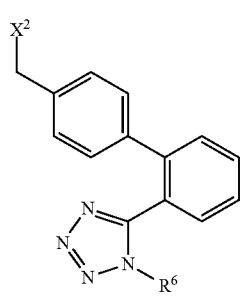
[5′]

wherein $X^2$ is a halogen atom and $R^6$ is a tetrazolyl-protecting group,
which is obtained by the method according to claim 9, or a salt thereof with a compound represented by the formula [17]:

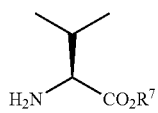

[17]

wherein R⁷ is a carboxy-protecting group, or a salt thereof to give a compound represented by the formula [18]:

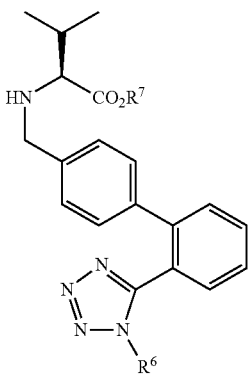

[18]

wherein R⁶ is a tetrazolyl-protecting group and R⁷ is a carboxy-protecting group, or a salt thereof;

2-A) removing R⁶ of a compound represented by the formula [18] or a salt thereof to give a compound represented by the formula [19]:

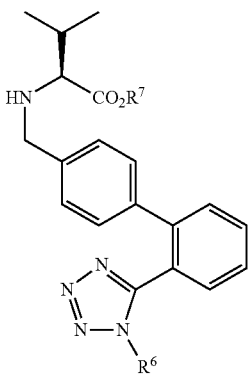

[19]

wherein R⁷ is a carboxy-protecting group, or a salt thereof;

3-A) reacting a compound represented by the formula [19] or a salt thereof with a compound represented by the formula [20]: CH₃CH₂CH₂CH₂CO—X³ (wherein X³ is a leaving group) to give a compound represented by the formula [21]:

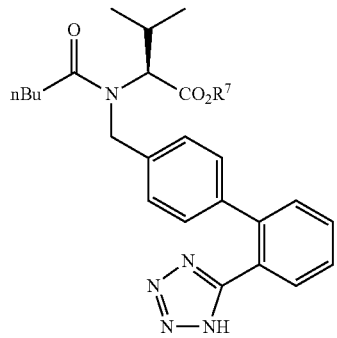

[21]

wherein R⁷ is a carboxy-protecting group, or a salt thereof;

4-A) removing R⁷ of a compound represented by the formula [21] or a salt thereof; or 2-B) reacting a compound represented by the formula [18] or a salt thereof with a compound represented by the formula [20] or a salt thereof to give a compound represented by the formula [22]:

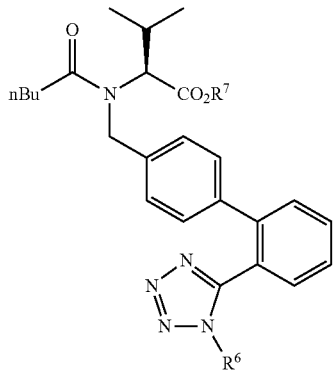

[22]

wherein R⁶ is a tetrazolyl-protecting group and R⁷ is a carboxy-protecting group, or a salt thereof; and 3-B) removing R⁶ and R⁷ of a compound represented by the formula [22] or a salt thereof.

13. A method of producing a compound represented by the formula [26]:

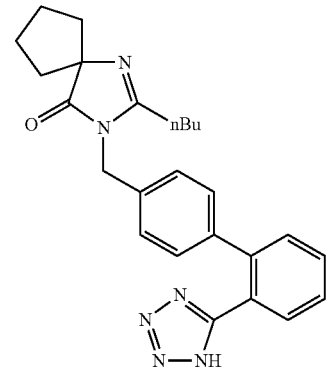

[26]

or a salt thereof, comprising reacting a biaryltetrazole derivative represented by the formula [5']:

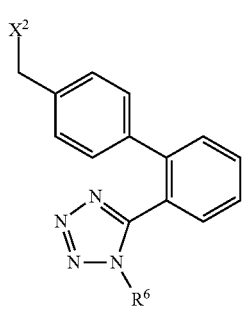

[5']

wherein X² is a halogen atom and R⁶ is a tetrazolyl-protecting group, which is obtained by the method according to claim 9, or a salt thereof with a compound represented by the formula [24]:

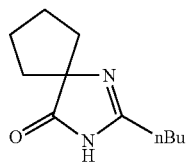

[24]

or a salt thereof
to give a compound represented by the formula [25]:

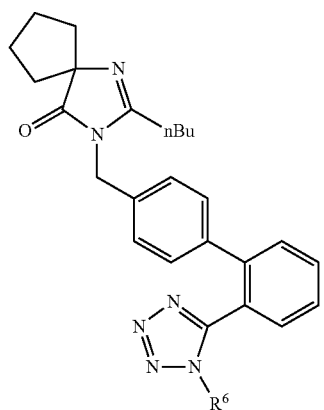

[25]

wherein R⁶ is a tetrazolyl-protecting group, or a salt thereof, and further removing R⁶.

14. A method of producing a compound represented by the formula [35]:

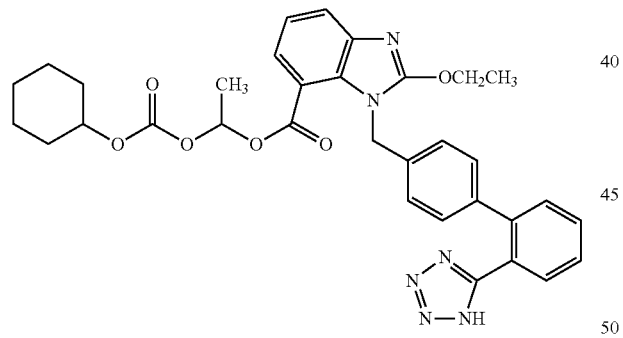

[35]

or a salt thereof, comprising
1) reacting a biaryltetrazole derivative represented by the formula [5']:

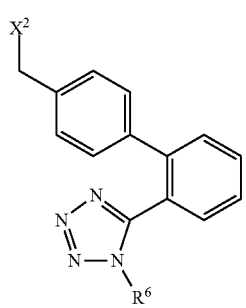

[5']

wherein $X^2$ is a halogen atom and $R^6$ is a tetrazolyl-protecting group,
which is obtained by the method according to claim 9, or a salt thereof
with a compound represented by the formula [X]:

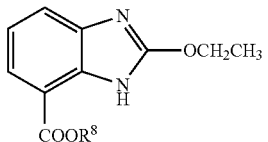

[X]

wherein $R^8$ is a carboxy-protecting group, or a salt thereof to give a compound represented by the formula [31]:

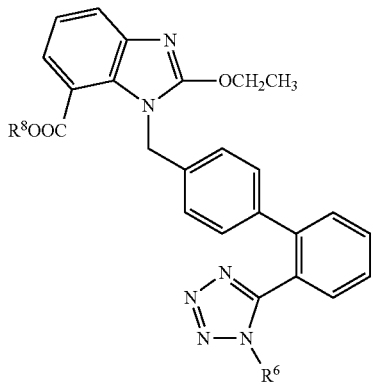

[31]

wherein $R^6$ is a tetrazolyl-protecting group and $R^8$ is a carboxy-protecting group, or a salt thereof;
2) removing $R^8$ of a compound represented by the formula [31] or a salt thereof to give a compound represented by the formula [32]:

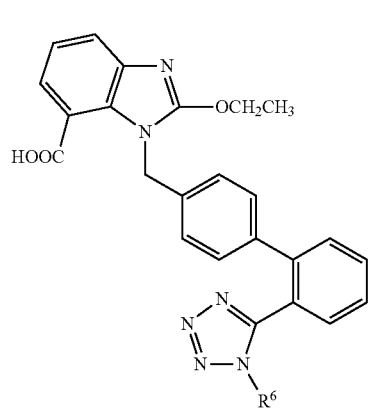

[32]

wherein $R^6$ is a tetrazolyl-protecting, or a salt thereof;
3) reacting a compound represented by the formula [32] or a salt thereof with a compound represented by the formula [33]:

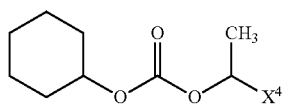

[33]

wherein $X^4$ is a leaving group or a hydroxyl group, or a salt thereof
to give a compound represented by the formula [34]:
[34]
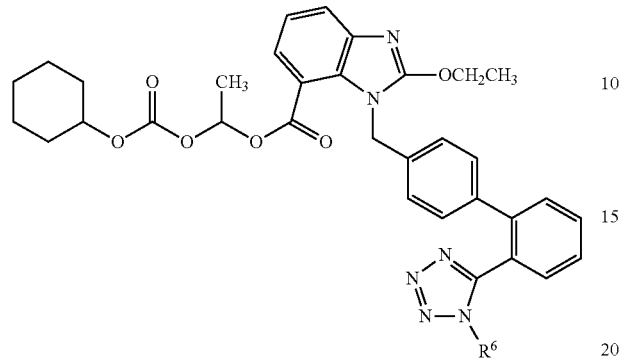
wherein $R^6$ is a tetrazolyl-protecting group, or a salt thereof (compound [34]); and
4) removing $R^6$ of a compound represented by the formula [34] or a salt thereof.
* * * * *